US012760079B2

(12) United States Patent
Wendt et al.

(10) Patent No.: US 12,760,079 B2
(45) Date of Patent: Oct. 13, 2026

(54) CNP VARIANTS AND CONJUGATES THEREOF

(71) Applicant: BIOMARIN PHARMACEUTICAL INC., Novato, CA (US)

(72) Inventors: Daniel J. Wendt, Novato, CA (US); Geoffrey Berguig, Novato, CA (US); Karol Estrada, Novato, CA (US); Jonathan LeBowitz, Novato, CA (US); Jason Alan Moss, Corte Madera, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 794 days.

(21) Appl. No.: 17/642,150

(22) PCT Filed: Sep. 16, 2020

(86) PCT No.: PCT/US2020/051100

§ 371 (c)(1),
(2) Date: Mar. 10, 2022

(87) PCT Pub. No.: WO2021/055497

PCT Pub. Date: Mar. 25, 2021

(65) Prior Publication Data

US 2023/0192799 A1 Jun. 22, 2023

Related U.S. Application Data

(60) Provisional application No. 63/038,667, filed on Jun. 12, 2020, provisional application No. 62/964,852, filed on Jan. 23, 2020, provisional application No. 62/963,350, filed on Jan. 20, 2020, provisional application No. 62/935,050, filed on Nov. 13, 2019, provisional application No. 62/901,093, filed on Sep. 16, 2019.

(51) Int. Cl.
*A61K 47/54* (2017.01)
*A61P 19/08* (2006.01)
*C07K 14/58* (2006.01)
*A61K 38/00* (2006.01)

(52) U.S. Cl.
CPC ............ *C07K 14/58* (2013.01); *A61K 47/542* (2017.08); *A61P 19/08* (2018.01); *A61K 38/00* (2013.01)

(58) Field of Classification Search
None
See application file for complete search history.

(56) References Cited

U.S. PATENT DOCUMENTS 5,352,770 A 10/1994 Matsuo
6,034,231 A 3/2000 Tanaka et al.
8,198,242 B2 6/2012 Wendt et al.
10,646,550 B2 * 5/2020 Bullens ................ A61K 9/0019
11,911,446 B2 * 2/2024 Bullens .................... A61K 9/19
12,214,015 B2 * 2/2025 O'Neill .............. A61K 38/2242
12,233,106 B2 * 2/2025 Day ..................... A61K 9/0019
2011/0213131 A1 * 9/2011 Christensen .............. A61P 3/10 530/399
2017/0035906 A1 * 2/2017 Naito ................. A61K 31/4745
2022/0280647 A1 * 9/2022 Ang ........................ A61P 19/00
2024/0156914 A1 * 5/2024 Bullens .................. A61K 47/10
2025/0032576 A1 * 1/2025 Jeha ................... A61K 38/2242

FOREIGN PATENT DOCUMENTS

CN 108472336 A 8/2018
RU 2573911 C2 1/2016
WO 2010/135541 A2 11/2010
WO WO-2016110577 A1 7/2016
WO WO-2017/020034 A1 2/2017
WO 2017/118698 A1 7/2017

OTHER PUBLICATIONS

Nakao, Kazumasa et al, "THe local cnp/gc-b system in growth plate is responsible for physiological encochondral bone growth." Sci Rep. (2014) 5:10554.*
The NCBI SEER training module, https://training.seer.cancer.gov/anatomy/skeletal/growth.html#:~:text=This%20process%20continues%20throughout%20childhood,no%20longer%20grow%20in%20length, downloaded Mar. 3, 2025.*
Argente, Jesus et al, "Genetics of growth disorders—which patients require genetic testing?" Front. Endocrin. (Sep. 2019) 10 article 602.*
Anderson, Brad, "Twerking girl distracts driver who crashes into motorcycle." CarScoops Apr. 18, 2017, https://www.carscoops.com/2017/04/twerking-girl-distracts-driver-who/.*
Koeberle, Martin, "A user friendly approach to developing an extended release product." Pharm. Technol. (Feb. 2019) 43(2) p. 22-26.*
Mergler, M et al, "The bachem practice of spps." Bachem sales literature (2005).*
Aigner et al., Apoptosis and cellular vitality: issues in osteoarthritic cartilage degeneration, Arth. Rheum., 46(8):1986-1996 (2002).
Alfonzo et al., Characterization of a G protein-coupled guanylyl cyclase-B receptor from bovine tracheal smooth muscle, Recept. Signal. Transduct. Res., 26:269-297 (2006).
Amano et al., Identification and functional characterization of two novel NPR2 mutations in Japanese patients with short stature, J. Clin. Endocrinol. Metab., 99:E713-718 (2014).
Bartels et al., Mutations in the transmembrane natriuretic peptide receptor NPR-B impair skeletal growth and cause acromesomelic dysplasia, type Maroteaux, Am. J. Hum. Genet., 75:27-34 (2004).
Boyle et al., An Expanded View of Complex Traits: From Polygenic to Omnigenic, Cell 169:1177-1186 (2017).
Caliceti et al., Pharmacokinetic and biodistribution properties of poly(ethylene glycol)-protein conjugates, Adv. Drug Deliv. Rev., 55:1261-77 (2003).

(Continued)

*Primary Examiner* — Fred H Reynolds
(74) *Attorney, Agent, or Firm* — MARSHALL, GERSTEIN & BORUN LLP

(57) ABSTRACT

The present disclosure, relates, in general, to stable variants of C-type natriuretic peptide (CNP) and uses thereof to treat bone-related disorders.

2 Claims, 19 Drawing Sheets

Specification includes a Sequence Listing.

(56) References Cited

OTHER PUBLICATIONS

Campbell et al., Structural Basis of Analog Specificity in PKG I and II, ACS Chem. Biol., 12:2388-2398 (2017).
Carmona et al., SHOX interacts with the chondrogenic transcription factors SOX5 and SOX6 to activate the aggrecan enhancer, Hum. Mol. Genet., 20:1547-1559 (2011).
Chen et al., Next-generation sequencing identifies rare variants associated with Noonan syndrome, Proc. Natl. Acad. Sci. U.S.A., 111(31):11473-8 (2014).
Davies, The cyclization of peptides and depsipeptides, J. Peptide Sci., 9:471-501 (2003).
Gardner et al., Molecular biology of the natriuretic peptide system: implications for physiology and hypertension, Hypertension, 49:419-426 (2007).
Griesser et al., Hydrophobic ion pairing: Key to highly payloaded self-emulsifying peptide drug delivery systems, Int. J. Pharmaceutics, 520:267-274 (2017).
Hisado-Oliva et al., Heterozygous NPR2 Mutations Cause Disproportionate Short Stature, Similar to Léri-Weill Dyschondrosteosis, J. Clin. Endocrinol. Metab., 100:E1133-1142 (2015).
Hisado-Oliva et al., Mutations in C-natriuretic peptide (NPPC): a novel cause of autosomal dominant short stature, Genetics Medicine, 20:91-97 (2018).
Hunt et al., Bioactivity and metabolism of C-type natriuretic peptide in normal man, J. Clin. Endocrinol. Metab., 78:1428-35 (1994).
Inoue et al., C-type natriuretic peptide improves growth retardation in a mouse model of cardio-facio-cutaneous syndrome, Hum. Mol. Genet., 28(1):74-83 (2019).
International Application No. PCT/US2020/051100, International Preliminary Report on Patentability, mailed Mar. 31, 2022.
International Application No. PCT/US2020/051100, International Search Report and Written Opinion, mailed Dec. 11, 2020.
Kawashima et al., Familial short stature with IGF-I receptor gene anomaly, Endocrine J., 59:179-185 (2012).
Kelly et al., Age-based reference ranges for annual height velocity in US children, J. Clin. Endocrinol. Metab., 99(6):2104-2112 (2014).
Lau et al., Discovery of the Once-Weekly Glucagon-Like Peptide-1 (GLP-1) Analogue Semaglutide, J. Med. Chem., 58:7370-7380 (2015).
Levin et al., Natriuretic Peptides, N. Engl. J. Med., 339:321-328 (Jul. 30, 1998).
Liu, et al., Trans Effects on Gene Expression Can Drive Omnigenic Inheritance, Cell, 177:1022-1034e6 (2019).
Lu et al., Hydrophobic Ion Pairing of Peptide Antibiotics for Processing into Controlled Release Nanocarrier Formulations, Mol. Pharmaceutics, 15:216-225 (2018), abstract only.
Marchini et al., A Track Record on SHOX: From Basic Research to Complex Models and Therapy, Endocr. Rev., 37:417-448 (2016).
Milosavljevic et al., Two cases of RIT1 associated Noonan syndrome: Further delineation of the clinical phenotype and review of the literature, Am. J. Med. Genet., 170(7):1874-80 (2016).
Musente et al., Spectrum of mutations in PTPN11 and genotype-phenotype correlation in 96 patients with Noonan syndrome and five patients with cardio-facio-cutaneous syndrome, Eur. J. Hum. Genet., 11:201-206 (2003).
Nakao et al., Molecular biology and biochemistry of the natriuretic peptide system. I: Natriuretic peptides, J. Hypertens., 10:907-912 (1992).
Nakao et al., Molecular biology and biochemistry of the natriuretic peptide system. II: Natriuretic peptide receptors, J. Hypertens., 10:1111-1114 (1992).
Olney et al., Heterozygous mutations in natriuretic peptide receptor-B (NPR2) are associated with short stature, J. Clin. Endocrinol. Metab., 91(4):1229-1232 (2006).
Ono et al., The ras-GTPase activity of neurofibromin restrains ERK-dependent FGFR signaling during endochondral bone formation, Hum. Mol. Genet., 22(15):3048-62 (2013).
Perlman et al., Glycosylation of an N-terminal extension prolongs the half-life and increases the in vivo activity of follicle stimulating hormone, J. Clin. Endo. Metab., 88:3227-35 (2003).
Pitkin et al., Charge and lipophilicity govern the pharmacokinetics of glycopeptide antibiotics, Antimicrob. Ag. Cheme., 29:440-444 (1986).
Plachy et al., High Prevalence of Growth Plate Gene Variants in Children With Familial Short Stature Treated With GH, J. Clin. Endocrinol. Metab., 104:4273-4281 (2019).
Pohler et al., Expression, purification, and characterization of the cGMP-dependent protein kinases I beta and II using the baculovirus system, FEBS Lett., 374:419-25 (1995).
Romano et al., Noonan syndrome: clinical features, diagnosis, and management guidelines, Pediatrics, 126(4):746-59 (2010).
Santi et al., Predictable and tunable half-life extension of therapeutic agents by controlled chemical release from macromolecular conjugates, Proc. Natl. Acad. Sci. U.S.A., 109:6211-6216, (2012).
Serra-Nedelec et al., Noonan syndrome-causing SHP2 mutants inhibit insulin-like growth factor 1 release via growth hormone-induced ERK hyperactivation, which contributes to short stature, PNAS, 109:4257-4262 (2012).
Stattin et al., A missense mutation in the aggrecan C-type lectin domain disrupts extracellular matrix interactions and causes dominant familial osteochondritis dissecans, Am. J. Hum. Genet., 86(2):126-37 (2010).
Stenson et al., The Human Gene Mutation Database: towards a comprehensive repository of inherited mutation data for medical research, genetic diagnosis and next-generation sequencing studies, Hum. Genet., 136:665-677 (2017).
Sudoh et al., C-type natriuretic peptide (CNP): a new member of natriuretic peptide family identified in porcine brain, Biochem. Biophys. Res. Commun., 168:863-870 (1990).
Tajan et al., The RASopathy Family: Consequences of Germline Activation of the RAS/MAPK Pathway, Endocr. Rev., 39(5):676-700 (2018).
Tang et al., An innovative method for preparation of hydrophobic ion-pairing colistin entrapped poly(lactic acid) nanoparticles: Loading and release mechanism study, Eur. J. Pharm. Sci., 102:63-70 (2017).
Vaandrager et al., Endogenous type II cGMP-dependent protein kinase exists as a dimer in membranes and can Be functionally distinguished from the type I isoforms, J. Biol. Chem., 272:11816-23 (1997).
Vasques et al., Heterozygous mutations in natriuretic peptide receptor-B (NPR2) gene as a cause of short stature in patients initially classified as idiopathic short stature, J. Clin. Endocrinol. Metab., 98:E1636-1644 (2013).
Vasques et al., IHH Gene Mutations Causing Short Stature With Nonspecific Skeletal Abnormalities and Response to Growth Hormone Therapy, J. Clin. Endocrinol. Metab., 103:604-614 (2018).
Vasques et al., Role of the natriuretic peptide system in normal growth and growth disorders, Horm. Res. Pediat., 82:222-229 (2014).
Vehaskari et al., Glomerular charge and urinary protein excretion: effects of systemic and intrarenal polycation infusion in the rat, Kidney Int'l., 22:127-135 (1982).
Wood et al., Defining the role of common variation in the genomic and biological architecture of adult human height, Nat. Genet., 46:1173-86 (2014).
Wu et al., Furin-mediated processing of Pro-C-type natriuretic peptide, J. Biol. Chem., 278:25847-852 (2003).
Russian Patent Application No. 2022110073, Office Action, mailed Mar. 28, 2024.
Breinholt et al., TransCon CNP, a sustained-release C-Type natriuretic peptide prodrug, a potentially safe and efficacious new therapeutic modality for the treatment of comorbidities associated with fibroblast growth factor receptor 3-related skeletal dysplasias, J. Pharmacol. Exp. Ther., 370: 459-471 (2019).
Breinholt et al., Phase 1 safety, tolerability, pharmacokinetics and pharmacodynamics results of a long-acting C-type natriuretic peptide prodrug, TransCon CNP, Br. J. Clin. Pharmacol. 88 :4763-4772 (2022).

(56) References Cited

OTHER PUBLICATIONS

Savarirayan et al., Once-weekly TransCon CNP (navepegritide) in children with achondroplasia (ACcomplisH): a phase 2, multicentre, randomised, double-blind, placebo-controlled, dose-escalation trial, EClinicalMedicine, 65:102258 (2023).
Filpula et al., Releasable PEGylation of proteins with customized linkers, Adv. Drug Deliv. Rev., 60.1:29-49 (2008).
Savarirayan et al., Once-weekly navepegritide in children with achondroplasia, The APPROACH randomized clinical trial, JAMA Ped., 180(1): 18-25 (Nov. 2025).

* cited by examiner

Figure 1
CNP conjugate with lipid moiety, glutamic acid, spacer, and electronic linker
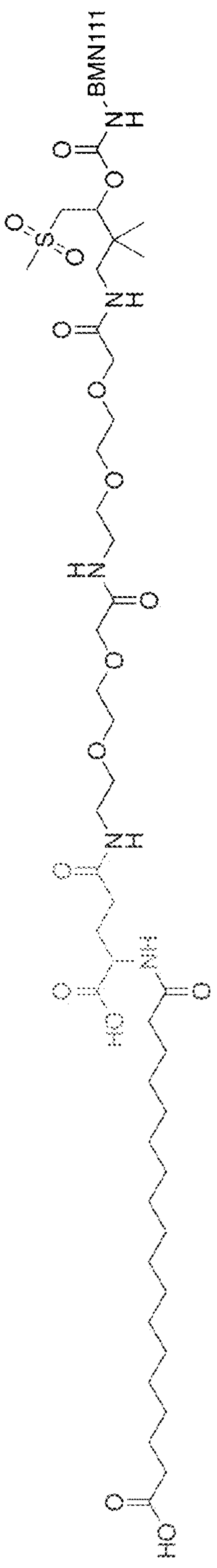
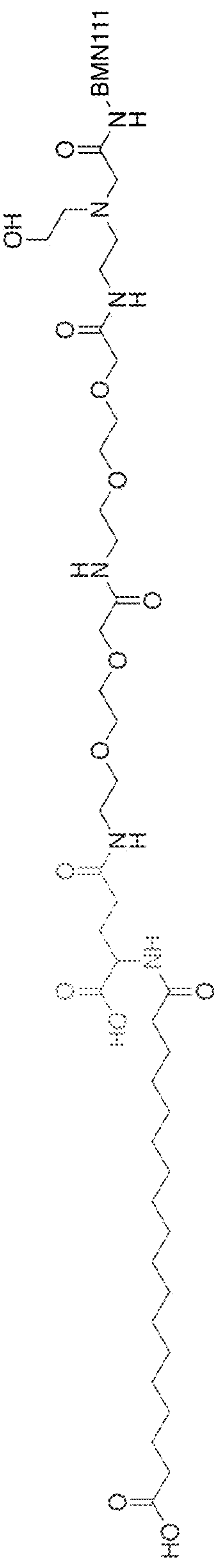
CNP conjugate with lipid moiety, glutamic acid, spacer, and peptoid linker

Figure 5

NPR2 Clone, nucleotide sequence

Clone 47, Allele 1(SEQ ID NO: 57):
ATGGCACTGCCATCCCTGCTACTGGTGGTGGCAGCCCTGGCAGGTGGGGTGCGTCCTCCGGGGGCACG
GAACCTGACGCTGGCGGTGGTGCTGCCAGAACACAACCTGAGCTATGCCTGGGCCTGGCCACGGGTGG
GTCCTGCTGTGGCACTGGCTGTGGAGGCGCTGGGCCGGGCACTGCCCGTGGACCTGCGGTTTGTCAGC
TCCGAACTAGACGGCGCCTGCTCTGAGTACCTGGCACCACTGCGCGCTGTGGATCTCAAGCTGTACCAT
GACCCCGACCTTCTGTTGGGCCCTGGTTGTGTGTACCCTGCTGCCTCTGTGGCTCGCTTTGCCTCGCACTG
GCACCTTCCCCTCCTGACTGCGGGTGCAGTGGCCTCTGGCTTTGCAGCTAAGAATGAGCATTATCGTACC
CTGGTTCGCACTGGCCCCTCTGCGCCCAAGCTGGGTGAGTTCGTAGTGACATTACACGGGCACTTCAATT
GGACTGCTCGGGCTGCTTTGCTGTATCTGGATGCTCGCACAGATGACCGGCCCCACTACTTCACCATCGA
GGGGGTGTTTGAGGCCCTGCAGGGCAGCAACCTCAGTGTGCAACACCAGGTGTATACCCGAGAGCCAG
GTGGCCCTGAGCAAGCCACCCACTTCATCAGAGCCAACGGGCGCA Clone 35, Allele 1(SEQ ID NO: 58):
ATGGCACTGCCATCCCTGCTACTGGTGGTGGCAGCCCTGGCAGGTGGGGTGCGTCCTCCGGGGGCACG
GAACCTGACGCTGGCGGTGGTGCTGCCAGAACACAACCTGAGCTATGCCTGGGCCTGGCCACGGGTGG
GTCCTGCTGTGGCACTGGCTGTGGAGGCGCTGGGCCGGGCACTGCCCGTGGACCTGCGGTTTGTCAGC
TCCGAACTAGACGGCGCCTGCTCTGAGTACCTGGCACCACTGCGCGCTGTGGATCTCAAGCTGTACCAT
GACCCCGACCTTCTGTTGGGCCCTGGTTGTGTGTACCCTGCTGCCTCTGTGGCTCGCTTTGCCTCGCACTG
GCACCTTCCCCTCCTGACTGCGGGTGCAGTGGCCTCTGGCTTTGCAGCTAAGAATGAGCATTATCGTACC
CTGGTTCGCACTGGCCCCTCTGCGCCCAAGCTGGGTGAGTTCGTAGTGACATTACACGGGCACTTCAATT
GGACTGCTCGGGCTGCTTTGCTGTATCTGGATGCTCGCACAGATGACCGGCCCCACTACTTCACCATCGA
GGGGGTGTTTGAGGCCCTGCAGGGCAGCAACCTCAGTGTGCAACACCAGGTGTATACCCGAGAGCCAG
GTGGCCCTGAGCAAGCCACCCACTTCATCAGAGCCAACGGGCGCA Clone 35, Allele 2(SEQ ID NO: 59):
ATGGCACTGCCATCCCTGCTACTGGTGGTGGCAGCCCTGGCAGGTGGGGTGCGTCCTCCGGGGGCACG
GAACCTGACGCTGGCGGTGGTGCTGCCAGAACACAACCTGAGCTATGCCTGGGCCTGGCCACGGGTGG
GTCCTGCTGTGGCACTGGCTGTGGAGGCGCTGGGCCGGGCACTGCCCGTGGACCTGCGGTTTGTCAGC
TCCGAACTAGACGGCGCCTGCTCTGAGTACCTGGCACCACTGCGCGCTGTGGATCTCAAGCTGTACCAT
GACCCCGACCTTCTGTTGGGCCCTGGTTGTGTGTACCCTGCTGCCTCTGTGGCTCGCTTTGCCTCGCACTG
GCACCTTCCCCTCCTGACTGCGGGTGCAGTGGCCTCTGGCTTTGCAGCTAAGAATGAGCATTATCGTACC
CTGGTTCGCACTGGCCCCTCTGCGCCCAAGCTGGGTGAGTTCGTAGTGACATTACACGGGCACTTCACA
ATTGGACTGCTCGGGCTGCTTTGCTGTATCTGGATGCTCGCACAGATGACCGGCCCCACTACTTCACCAT
CGAGGGGGTGTTTGAGGCCCTGCAGGGCAGCAACCTCAGTGTGCAACACCAGGTGTATACCCGAGAGC
CAGGTGGCCCTGAGCAAGCCACCCACTTCATCAGAGCCAACGGGCGCA Clone 47, Allele 1(SEQ ID NO: 60)
ATGGCACTGCCATCCCTGCTACTGGTGGTGGCAGCCCTGGCAGGTGGGGTGCGTCCTCCGGGGGCACG
GAACCTGACGCTGGCGGTGGTGCTGCCAGAACACAACCTGAGCTATGCCTGGGCCTGGCCACGGGTGG

Figure 5 (cont'd)

GTCCTGCTGTGGCACTGGCTGTGGAGGCGCTGGGCCGGGCACTGCCCGTGGACCTGCGGTTTGTCAGC
TCCGAACTAGACGGCGCCTGCTCTGAGTACCTGGCACCACTGCGCGCTGTGGATCTCAAGCTGTACCAT
GACCCCGACCTTCTGTTGGGCCCTGGTTGTGTGTACCCTGCTGCCTCTGTGGCTCGCTTTGCCTCGCACTG
GCACCTTCCCCTCCTGACTGCGGGTGCAGTGGCCTCTGGCTTTGCAGCTAAGAATGAGCATTATCGTACC
CTGGTTCGCACTGGCCCCTCTGCGCCCAAGCTGGGTGAGTTCGTAGTGACATTACACGGGCACTTCAATT
GGACTGCTCGGGCTGCTTTGCTGTATCTGGATGCTCGCACAGATGACCGGCCCCACTACTTCACCATCCG
AGGGGGTGTTTGAGGCCCTGCAGGGCAGCAACCTCAGTGTGCAACACCAGGTGTATACCCGAGAGCCA
GGTGGCCCTGAGCAAGCCACCCACTTCATCAGAGCCAACGGGCGCA

Clone 47, Allele 2(SEQ ID NO: 61):
ATGGCACTGCCATCCCTGCTACTGGTGGTGGCAGCCCTGGCAGGTGGGGTGCGTCCTCCGGGGGCACG
GAACCTGACGCTGGCGGTGGTGCTGCCAGAACACAACCTGAGCTATGCCTGGGCCTGGCCACGGGTGG
GTCCTGCTGTGGCACTGGCTGTGGAGGCGCTGGGCCGGGCACTGCCCGTGGACCTGCGGTTTGTCAGC
TCCGAACTAGACGGCGCCTGCTCTGAGTACCTGGCACCGGGGTGTTTGAGGCCCTGCAGGGCAGCAAC
CTCAGTGTGCAACACCAGGTGTATACCCGAGAGCCAGGTGGCCCTGAGCAAGCCACCCACTTCATCAGA
GCCAACGGGCGCA

NPR2 Clone, predicted protein product sequence

Clone 47, Allele 1(SEQ ID NO: 62):
MALPSLLLVVAALAGGVRPPGARNLTLAVVLPEHNLSYAWAWPRVGPAVALAVEALGRALPVDLRFVSSEL
DGACSEYLAPLRAVDLKLYHDPDLLLGPGCVYPAASVARFASHWHLPLLTAGAVASGFAAKNEHYRTLVRTG
PSAPKLGEFVVTLHGHFNWTARAALLYLDARTDDRPHYFTIEGVFEALQGSNLSVQHQVYTREPGGPEQAT
HFIRANGRIVYICGPLEMLHEILLQAQRENLTNGDYVFFYLDVFGESLRAGPTRATGRPWQDNRTQEQAQAL
REAFQTVLVITYREPPNPEYQEFQNRLLIRAREDFGVELAPSLMNLIAGCFYDGILLYAQVLNETIQEGGTRED
GLRIVEKMQGRRYHGVTGLVVMDKNNDRETDFVLWAMGDLESGDFQPAAHYSGAEKQIWWTGRPIPW
VKGAPPLDNPPCAFDLDDPSCDKTPLSTLAIVALGTGITFIMFGVSSFLIFRKLMLEKELASMLWRIRWEELQF
GNSDRYHKGAGSRLTLSLRGSSYGSLMTAHGKYQIFANTGHFKGNVVAIKHVNKKRIELTRQVLFELKHMRD
VQFNHLTRFIGACIDPPNICIVTEYCPRGSLQDILENDSINLDWMFRYSLINDLVKGMAFLHNSIISSHGSLKSS
NCVVDSRFVLKITDYGLASFRSTAEPDDSHALYAKKLWTAPELLSGNPLPTTGMQKADVYSFAIILQEIALRSG
PFYLEGLDLSPKEIVQKVRNGQRPYFRPSIDRTQLNEELVLLMERCWAQDPTERPDFGQIKGFIRRFNKEGGT
SILDNLLLRMEQYANNLEKLVEERTQAYLEEKRKAEALLYQILPHSVAEQLKRGETVQAEAFDSVTIYFSDIVGF
TALSAESTPMQVVTLLNDLYTCFDAIIDNFDVYKVETIGDAYMVVSGLPGRNGQRHAPEIARMALALLDAVS
SFRIRHRPHDQLRLRIGVHTGPVCAGVVGLKMPRYCLFGDTVNTASRMESNGQALKIHVSSTTKDALDELGC
FQLELRGDVEMKGKGKMRTYWLLGERKGPPGLL*

Clone 35, Allele 1(SEQ ID NO: 63):
MALPSLLLVVAALAGGVRPPGARNLTLAVVLPEHNLSYAWAWPRVGPAVALAVEALGRALPVDLRFVSSEL
DGACSEYLAPLRAVDLKLYHDPDLLLGPGCVYPAASVARFASHWHLPLLTAGAVASGFAAKNEHYRTLVRTG
PSAPKLGEFVVTLHGHFNWTARAALLYLDARTDDRPHYFTIEGVFEALQGSNLSVQHQVYTREPGGPEQAT

Figure 5 (cont'd)

HFIRANGRIVYICGPLEMLHEILLQAQRENLTNGDYVFFYLDVFGESLRAGPTRATGRPWQDNRTQEQAQAL
REAFQTVLVITYREPPNPEYQEFQNRLLIRAREDFGVELAPSLMNLIAGCFYDGILLYAQVLNETIQEGGTRED
GLRIVEKMQGRRYHGVTGLVVMDKNNDRETDFVLWAMGDLESGDFQPAAHYSGAEKQIWWTGRPIPW
VKGAPPLDNPPCAFDLDDPSCDKTPLSTLAIVALGTGITFIMFGVSSFLIFRKLMLEKELASMLWRIRWEELQF
GNSDRYHKGAGSRLTLSLRGSSYGSLMTAHGKYQIFANTGHFKGNVVAIKHVNKKRIELTRQVLFELKHMRD
VQFNHLTRFIGACIDPPNICIVTEYCPRGSLQDILENDSINLDWMFRYSLINDLVKGMAFLHNSIISSHGSLKSS
NCVVDSRFVLKITDYGLASFRSTAEPDDSHALYAKKLWTAPELLSGNPLPTTGMQKADVYSFAIILQEIALRSG
PFYLEGLDLSPKEIVQKVRNGQRPYFRPSIDRTQLNEELVLLMERCWAQDPTERPDFGQIKGFIRRFNKEGGT
SILDNLLLRMEQYANNLEKLVEERTQAYLEEKRKAEALLYQILPHSVAEQLKRGETVQAEAFDSVTIYFSDIVGF
TALSAESTPMQVVTLLNDLYTCFDAIIDNFDVYKVETIGDAYMVVSGLPGRNGQRHAPEIARMALALLDAVS
SFRIRHRPHDQLRLRIGVHTGPVCAGVVGLKMPRYCLFGDTVNTASRMESNGQALKIHVSSTTKDALDELGC
FQLELRGDVEMKGKGKMRTYWLLGERKGPPGLL*

Clone 35, Allele 2(SEQ ID NO: 64):
MALPSLLLVVAALAGGVRPPGARNLTLAVVLPEHNLSYAWAWPRVGPAVALAVEALGRALPVDLRFVSSEL
DGACSEYLAPLRAVDLKLYHDPDLLLGPGCVYPAASVARFASHWHLPLLTAGAVASGFAAKNEHYRTLVRTG
PSAPKLGEFVVTLHGHFTIGLLGLLCCIWMLAQMTGPTTSPSRGCLRPCRAATSVCNTRCIPESQVALSKPPTS
SEPTGALCISAARWRCFMRSCFRPRGRT*

Clone 47, Allele 1(SEQ ID NO: 65):
MALPSLLLVVAALAGGVRPPGARNLTLAVVLPEHNLSYAWAWPRVGPAVALAVEALGRALPVDLRFVSSEL
DGACSEYLAPLRAVDLKLYHDPDLLLGPGCVYPAASVARFASHWHLPLLTAGAVASGFAAKNEHYRTLVRTG
PSAPKLGEFVVTLHGHFNWTARAALLYLDARTDDRPHYFTIRGGV*

Clone 47, Allele 2(SEQ ID NO: 66):
MALPSLLLVVAALAGGVRPPGARNLTLAVVLPEHNLSYAWAWPRVGPAVALAVEALGRALPVDLRFVSSEL
DGACSEYLAPGCLRPCRAATSVCNTRCIPESQVALSKPPTSSEPTGALCISAARWRCFMRSCFRPRGRT*

Figure 6

Genetic Variants Found in NPR2 Genes

| **NPR2 Mutations** | | | |
|---|---|---|---|
| G21R | P301S | Q500X | R745Q |
| A48S | R318Q | H508D | R819C |
| A59T | R358W | G541S | T861I |
| V102A | E359A | A549T | V883M |
| R110G | I364fs | R562Q | T907M |
| A164G | E389D | R601H | G917R |
| I226V | E415K | R601S | R921Q |
| Y250X | K480N | E609K | R957C |
| R263H | A488P | S721R | L1009V |
| T297M | I494S | E727Q | |

Figure 7

Genetic variants found in the 5 Core genes

| chr | position | alleles | AC | variant_q | vep.consequence | vep.impact | vep.symbol | vep.hgvsc | vep.hgvsp | vep.gnom: | vep.cadd_phred |
|---|---|---|---|---|---|---|---|---|---|---|---|
| 2 | 231925451 | ['C', 'G'] | 1 | 1.00 | ['missense_variant'] | MODERATE | NPPC | ENST00000409852.2:c.355G>C | ENSP00000387159.1:p.Gly119Arg | | 33 |
| 2 | 231925486 | ['G', 'GT'] | 1 | 1.00 | ['frameshift_variant' | HIGH | NPPC | ENST00000409852.2:c.319_320insA | ENSP00000387159.1:p.Ser107TyrfsTer37 | | |
| 2 | 231925513 | ['T', 'C'] | 1 | 1.00 | ['missense_variant'] | MODERATE | NPPC | ENST00000409852.2:c.293A>G | ENSP00000387159.1:p.Tyr98Cys | | 23 |
| 2 | 231925514 | ['A', 'C'] | 2 | 1.00 | ['missense_variant'] | MODERATE | NPPC | ENST00000409852.2:c.292T>G | ENSP00000387159.1:p.Tyr98Asp | | 18 |
| 2 | 231925523 | ['C', 'A'] | 2 | 1.00 | ['missense_variant'] | MODERATE | NPPC | ENST00000409852.2:c.283G>T | ENSP00000387159.1:p.Ala95Ser | | 15 |
| 2 | 231925529 | ['G', 'A'] | 1 | 1.00 | ['missense_variant'] | MODERATE | NPPC | ENST00000409852.2:c.277C>T | ENSP00000387159.1:p.Pro93Ser | 4.04E-06 | 26 |
| 2 | 231925540 | ['A', 'T'] | 1 | 1.00 | ['missense_variant'] | MODERATE | NPPC | ENST00000409852.2:c.266T>A | ENSP00000387159.1:p.Leu89Gln | | 23 |
| 2 | 231925550 | ['C', 'G'] | 1 | 1.00 | ['missense_variant'] | MODERATE | NPPC | ENST00000409852.2:c.256G>C | ENSP00000387159.1:p.Ala86Pro | | 23 |
| 2 | 231925553 | ['A', 'G'] | 1 | 1.00 | ['missense_variant'] | MODERATE | NPPC | ENST00000409852.2:c.253T>C | ENSP00000387159.1:p.Trp85Arg | 4.06E-06 | 23 |
| 2 | 231925580 | ['G', 'T'] | 3 | 1.00 | ['missense_variant'] | MODERATE | NPPC | ENST00000409852.2:c.226C>A | ENSP00000387159.1:p.Arg76Ser | 6.96E-05 | 25 |
| 2 | 231925584 | ['G', 'C'] | 1 | 1.00 | ['missense_variant'] | MODERATE | NPPC | ENST00000409852.2:c.222C>G | ENSP00000387159.1:p.Asp74Glu | | 21 |
| 2 | 231925597 | ['C', 'A'] | 1 | 1.00 | ['missense_variant'] | MODERATE | NPPC | ENST00000409852.2:c.209G>T | ENSP00000387159.1:p.Arg70Leu | | 26 |
| 2 | 231925600 | ['G', 'T'] | 1 | 1.00 | ['stop_gained'] | HIGH | NPPC | ENST00000409852.2:c.206C>A | ENSP00000387159.1:p.Ser69Ter | | 38 |
| 2 | 231925639 | ['G', 'A'] | 7 | 1.00 | ['missense_variant'] | MODERATE | NPPC | ENST00000409852.2:c.167C>T | ENSP00000387159.1:p.Ala56Val | 3.95E-05 | 18 |
| 2 | 231925646 | ['C', 'A'] | 1 | 1.00 | ['missense_variant'] | MODERATE | NPPC | ENST00000409852.2:c.160G>T | ENSP00000387159.1:p.Asp54Tyr | | 23 |
| 2 | 231925649 | ['CCTT', 'C' | 3 | 1.00 | ['inframe_deletion'] | MODERATE | NPPC | ENST00000409852.2:c.154_156del | ENSP00000387159.1:p.Lys52del | 4.44E-06 | |
| 2 | 231925649 | ['C', 'T'] | 1 | 1.00 | ['missense_variant'] | MODERATE | NPPC | ENST00000409852.2:c.157G>A | ENSP00000387159.1:p.Gly53Ser | | 21 |
| 2 | 231925657 | ['T', 'C'] | 3 | 1.00 | ['missense_variant'] | MODERATE | NPPC | ENST00000409852.2:c.149A>G | ENSP00000387159.1:p.Gln50Arg | 1.81E-05 | 21 |
| 2 | 231925663 | ['C', 'A'] | 1 | 1.00 | ['missense_variant'] | MODERATE | NPPC | ENST00000409852.2:c.143G>T | ENSP00000387159.1:p.Gly48Val | | 24 |
| 2 | 231925669 | ['G', 'C'] | 1 | 1.00 | ['missense_variant'] | MODERATE | NPPC | ENST00000409852.2:c.137C>G | ENSP00000387159.1:p.Ala46Gly | | 23 |
| 2 | 231925708 | ['C', 'T'] | 1 | 1.00 | ['missense_variant'] | MODERATE | NPPC | ENST00000409852.2:c.98G>A | ENSP00000387159.1:p.Arg33Gln | 5.65E-06 | 24 |
| 2 | 231925711 | ['G', 'A'] | 1 | 1.00 | ['missense_variant'] | MODERATE | NPPC | ENST00000409852.2:c.95C>T | ENSP00000387159.1:p.Pro32Leu | | 13 |
| 2 | 231926189 | ['A', 'G'] | 1 | 1.00 | ['missense_variant'] | MODERATE | NPPC | ENST00000409852.2:c.61T>C | ENSP00000387159.1:p.Ser21Pro | 3.40E-05 | 23 |
| 2 | 231926200 | ['G', 'C'] | 1 | 1.00 | ['missense_variant'] | MODERATE | NPPC | ENST00000409852.2:c.50C>G | ENSP00000387159.1:p.Ser17Cys | | 28 |
| 2 | 231926201 | ['A', 'AGA( | 1 | 1.00 | ['inframe_insertion'] | MODERATE | NPPC | ENST00000409852.2:c.40_48dup | ENSP00000387159.1:p.Thr14_Leu16dup | | |
| 4 | 1793974 | ['G', 'GTG( | 1 | 1.00 | ['inframe_insertion'] | MODERATE | FGFR3 | ENST00000340107.8:c.42_47dup | ENSP00000339824.4:p.Ala15_Ile16insMetAla | | |
| 4 | 1794009 | ['G', 'C'] | 1 | 1.00 | ['missense_variant'] | MODERATE | FGFR3 | ENST00000340107.8:c.75G>C | ENSP00000339824.4:p.Leu25Phe | | 8 |
| 4 | 1794016 | ['G', 'C'] | 2 | 1.00 | ['missense_variant'] | MODERATE | FGFR3 | ENST00000340107.8:c.82G>C | ENSP00000339824.4:p.Glu28Gln | | 22 |
| 4 | 1794043 | ['G', 'A'] | 1 | 1.00 | ['missense_variant', | MODERATE | FGFR3 | ENST00000340107.8:c.109G>A | ENSP00000339824.4:p.Glu37Lys | | 22 |
| 4 | 1799274 | ['G', 'A'] | 4 | 1.00 | ['missense_variant'] | MODERATE | FGFR3 | ENST00000340107.8:c.130G>A | ENSP00000339824.4:p.Gly44Ser | 0.000225 | 0 |
| 4 | 1799289 | ['T', 'G'] | 1 | 1.00 | ['missense_variant'] | MODERATE | FGFR3 | ENST00000340107.8:c.145T>G | ENSP00000339824.4:p.Leu49Val | 4.06E-06 | 5 |
| 4 | 1799292 | ['G', 'T'] | 7 | 1.00 | ['missense_variant'] | MODERATE | FGFR3 | ENST00000340107.8:c.148G>T | ENSP00000339824.4:p.Val50Phe | | 22 |
| 4 | 1799292 | ['G', 'A'] | 1 | 1.00 | ['missense_variant'] | MODERATE | FGFR3 | ENST00000340107.8:c.148G>A | ENSP00000339824.4:p.Val50Ile | | 13 |
| 4 | 1799303 | ['C', 'A'] | 1 | 1.00 | ['missense_variant'] | MODERATE | FGFR3 | ENST00000340107.8:c.159C>A | ENSP00000339824.4:p.Ser53Arg | | 11 |
| 4 | 1799304 | ['G', 'A'] | 1 | 1.00 | ['missense_variant'] | MODERATE | FGFR3 | ENST00000340107.8:c.160G>A | ENSP00000339824.4:p.Gly54Arg | 4.06E-05 | 23 |
| 4 | 1799310 | ['G', 'A'] | 1 | 1.00 | ['missense_variant'] | MODERATE | FGFR3 | ENST00000340107.8:c.166G>A | ENSP00000339824.4:p.Ala56Thr | | 0 |
| 4 | 1799316 | ['G', 'A'] | 3 | 1.00 | ['missense_variant'] | MODERATE | FGFR3 | ENST00000340107.8:c.172G>A | ENSP00000339824.4:p.Glu58Lys | 8.13E-06 | 15 |
| 4 | 1799328 | ['C', 'A'] | 1 | 1.00 | ['missense_variant'] | MODERATE | FGFR3 | ENST00000340107.8:c.184C>A | ENSP00000339824.4:p.Pro62Thr | | 1 |
| 4 | 1799332 | ['C', 'G'] | 5 | 1.00 | ['missense_variant'] | MODERATE | FGFR3 | ENST00000340107.8:c.188C>G | ENSP00000339824.4:p.Pro63Arg | 3.27E-05 | 3 |
| 4 | 1799337 | ['G', 'A'] | 3 | 1.00 | ['missense_variant'] | MODERATE | FGFR3 | ENST00000340107.8:c.193G>A | ENSP00000339824.4:p.Gly65Arg | 0.001076 | 11 |
| 4 | 1799389 | ['T', 'C'] | 2 | 1.00 | ['missense_variant'] | MODERATE | FGFR3 | ENST00000340107.8:c.245T>C | ENSP00000339824.4:p.Val82Ala | | 2 |
| 4 | 1799416 | ['C', 'T'] | 1 | 1.00 | ['missense_variant'] | MODERATE | FGFR3 | ENST00000340107.8:c.272C>T | ENSP00000339824.4:p.Pro91Leu | 0.000176 | 8 |
| 4 | 1799422 | ['G', 'A'] | 1 | 1.00 | ['missense_variant'] | MODERATE | FGFR3 | ENST00000340107.8:c.278G>A | ENSP00000339824.4:p.Arg93Gln | 1.69E-05 | 12 |
| 4 | 1799457 | ['G', 'A'] | 2 | 1.00 | ['missense_variant'] | MODERATE | FGFR3 | ENST00000340107.8:c.313G>A | ENSP00000339824.4:p.Gly105Arg | 9.26E-06 | 24 |
| 4 | 1799472 | ['C', 'T'] | 1 | 1.00 | ['missense_variant'] | MODERATE | FGFR3 | ENST00000340107.8:c.328C>T | ENSP00000339824.4:p.Arg110Trp | 1.50E-05 | 22 |
| 4 | 1799473 | ['G', 'A'] | 2 | 1.00 | ['missense_variant'] | MODERATE | FGFR3 | ENST00000340107.8:c.329G>A | ENSP00000339824.4:p.Arg110Gln | 7.05E-05 | 17 |
| 4 | 1799479 | ['G', 'A'] | 3 | 1.00 | ['missense_variant'] | MODERATE | FGFR3 | ENST00000340107.8:c.335G>A | ENSP00000339824.4:p.Arg112Gln | 0.000229 | 9 |
| 4 | 1799491 | ['G', 'A'] | 5 | 1.00 | ['missense_variant'] | MODERATE | FGFR3 | ENST00000340107.8:c.347G>A | ENSP00000339824.4:p.Arg116His | 4.18E-05 | 3 |
| 4 | 1799493 | ['G', 'A'] | 3 | 1.00 | ['missense_variant'] | MODERATE | FGFR3 | ENST00000340107.8:c.349G>A | ENSP00000339824.4:p.Val117Ile | 7.21E-05 | 0 |
| 4 | 1799496 | ['C', 'G'] | 1 | 1.00 | ['missense_variant'] | MODERATE | FGFR3 | ENST00000340107.8:c.352C>G | ENSP00000339824.4:p.Leu118Val | 1.22E-05 | 12 |
| 4 | 1799756 | ['C', 'A'] | 3 | 1.00 | ['missense_variant'] | MODERATE | FGFR3 | ENST00000340107.8:c.389C>A | ENSP00000339824.4:p.Ser130Tyr | | 19 |
| 4 | 1799756 | ['C', 'T'] | 1 | 1.00 | ['missense_variant'] | MODERATE | FGFR3 | ENST00000340107.8:c.389C>T | ENSP00000339824.4:p.Ser130Phe | 1.20E-05 | 17 |
| 4 | 1799758 | ['T', 'C'] | 1 | 1.00 | ['missense_variant'] | MODERATE | FGFR3 | ENST00000340107.8:c.391T>C | ENSP00000339824.4:p.Ser131Pro | 8.01E-06 | 22 |
| 4 | 1799770 | ['G', 'A'] | 6 | 1.00 | ['missense_variant'] | MODERATE | FGFR3 | ENST00000340107.8:c.403G>A | ENSP00000339824.4:p.Glu135Lys | 1.20E-05 | 21 |
| 4 | 1799776 | ['G', 'A'] | 1 | 1.00 | ['missense_variant'] | MODERATE | FGFR3 | ENST00000340107.8:c.409G>A | ENSP00000339824.4:p.Gly137Arg | 1.60E-05 | 15 |
| 4 | 1799792 | ['AGGACA | 1 | 1.00 | ['inframe_deletion'] | MODERATE | FGFR3 | ENST00000340107.8:c.436_445+2del | | 1.20E-05 | |
| 4 | 1801373 | ['C', 'T'] | 1 | 1.00 | ['missense_variant'] | MODERATE | FGFR3 | ENST00000340107.8:c.452C>T | ENSP00000339824.4:p.Pro151Leu | | 27 |
| 4 | 1801384 | ['C', 'T'] | 1 | 1.00 | ['missense_variant'] | MODERATE | FGFR3 | ENST00000340107.8:c.463C>T | ENSP00000339824.4:p.Arg155Trp | 6.53E-06 | 24 |
| 4 | 1801393 | ['C', 'T'] | 1 | 1.00 | ['missense_variant'] | MODERATE | FGFR3 | ENST00000340107.8:c.472C>T | ENSP00000339824.4:p.Arg158Trp | 6.50E-06 | 23 |
| 4 | 1801394 | ['G', 'A'] | 5 | 1.00 | ['missense_variant'] | MODERATE | FGFR3 | ENST00000340107.8:c.473G>A | ENSP00000339824.4:p.Arg158Gln | 5.85E-05 | 27 |
| 4 | 1801402 | ['A', 'G'] | 1 | 1.00 | ['missense_variant'] | MODERATE | FGFR3 | ENST00000340107.8:c.481A>G | ENSP00000339824.4:p.Lys161Glu | | 31 |
| 4 | 1801435 | ['G', 'A'] | 3 | 1.00 | ['missense_variant'] | MODERATE | FGFR3 | ENST00000340107.8:c.514G>A | ENSP00000339824.4:p.Val172Ile | 6.67E-05 | 24 |

Figure 7 cont'd

Genetic variants found in the 5 Core genes

| chr | position | alleles | AC | variant_q | vep.consequence | vep.impact | vep.symbol | vep.hgvsc | vep.hgvsp | vep.gnom: | vep.cadd_phred |
|---|---|---|---|---|---|---|---|---|---|---|---|
| 4 | 1801439 | ['G', 'A'] | 1 | 1.00 | ['missense_variant'] | MODERATE | FGFR3 | ENST00000340107.8:c.518G>A | ENSP00000339824.4:p.Arg173His | 4.00E-05 | 28 |
| 4 | 1801445 | ['G', 'A'] | 2 | 1.00 | ['missense_variant'] | MODERATE | FGFR3 | ENST00000340107.8:c.524G>A | ENSP00000339824.4:p.Arg175His | 3.98E-05 | 27 |
| 4 | 1801456 | ['G', 'A'] | 2 | 1.00 | ['missense_variant'] | MODERATE | FGFR3 | ENST00000340107.8:c.535G>A | ENSP00000339824.4:p.Ala179Thr | | 14 |
| 4 | 1801477 | ['A', 'G'] | 1 | 1.00 | ['missense_variant'] | MODERATE | FGFR3 | ENST00000340107.8:c.556A>G | ENSP00000339824.4:p.Ile186Val | | 23 |
| 4 | 1801478 | ['T', 'A'] | 1 | 1.00 | ['missense_variant'] | MODERATE | FGFR3 | ENST00000340107.8:c.557T>A | ENSP00000339824.4:p.Ile186Asn | | 25 |
| 4 | 1801481 | ['C', 'A'] | 4 | 1.00 | ['missense_variant'] | MODERATE | FGFR3 | ENST00000340107.8:c.560C>A | ENSP00000339824.4:p.Ser187Tyr | 2.52E-05 | 19 |
| 4 | 1801495 | ['G', 'A'] | 1 | 1.00 | ['missense_variant'] | MODERATE | FGFR3 | ENST00000340107.8:c.574G>A | ENSP00000339824.4:p.Gly192Ser | | 26 |
| 4 | 1801506 | ['C', 'G'] | 4 | 1.00 | ['missense_variant'] | MODERATE | FGFR3 | ENST00000340107.8:c.585C>G | ENSP00000339824.4:p.Phe195Leu | 1.84E-05 | 23 |
| 4 | 1801510 | ['G', 'A'] | 2 | 1.00 | ['missense_variant'] | MODERATE | FGFR3 | ENST00000340107.8:c.589G>A | ENSP00000339824.4:p.Gly197Ser | 6.04E-06 | 24 |
| 4 | 1801634 | ['G', 'T'] | 1 | 1.00 | ['missense_variant'] | MODERATE | FGFR3 | ENST00000340107.8:c.630G>T | ENSP00000339824.4:p.Gln210His | | 16 |
| 4 | 1801689 | ['G', 'A'] | 1 | 1.00 | ['missense_variant'] | MODERATE | FGFR3 | ENST00000340107.8:c.685G>A | ENSP00000339824.4:p.Val229Ile | | 12 |
| 4 | 1801717 | ['G', 'A'] | 7 | 1.00 | ['missense_variant'] | MODERATE | FGFR3 | ENST00000340107.8:c.713G>A | ENSP00000339824.4:p.Arg238Gln | 0.0005 | 9 |
| 4 | 1801743 | ['G', 'A'] | 1 | 1.00 | ['missense_variant', | MODERATE | FGFR3 | ENST00000340107.8:c.739G>A | ENSP00000339824.4:p.Glu247Lys | 1.34E-05 | 34 |
| 4 | 1801841 | ['C', 'T'] | 1 | 1.00 | ['missense_variant'] | MODERATE | FGFR3 | ENST00000340107.8:c.746C>T | ENSP00000339824.4:p.Ser249Phe | 1.26E-05 | 25 |
| 4 | 1801849 | ['C', 'T'] | 1 | 1.00 | ['missense_variant'] | MODERATE | FGFR3 | ENST00000340107.8:c.754C>T | ENSP00000339824.4:p.Arg252Trp | | 25 |
| 4 | 1801874 | ['C', 'T'] | 8 | 1.00 | ['missense_variant'] | MODERATE | FGFR3 | ENST00000340107.8:c.779C>T | ENSP00000339824.4:p.Pro260Leu | 2.51E-05 | 28 |
| 4 | 1801903 | ['G', 'A'] | 1 | 1.00 | ['missense_variant'] | MODERATE | FGFR3 | ENST00000340107.8:c.808G>A | ENSP00000339824.4:p.Asp270Asn | 9.32E-05 | 22 |
| 4 | 1801948 | ['A', 'G'] | 4 | 1.00 | ['missense_variant'] | MODERATE | FGFR3 | ENST00000340107.8:c.853A>G | ENSP00000339824.4:p.Ile285Val | 2.41E-05 | 26 |
| 4 | 1802005 | ['C', 'T'] | 1 | 1.00 | ['missense_variant'] | MODERATE | FGFR3 | ENST00000340107.8:c.910C>T | ENSP00000339824.4:p.Pro304Ser | | 26 |
| 4 | 1802941 | ['G', 'A'] | 1 | 1.00 | ['missense_variant'] | MODERATE | FGFR3 | ENST00000340107.8:c.958G>A | ENSP00000339824.4:p.Asp320Asn | 4.33E-06 | 23 |
| 4 | 1802944 | ['G', 'A'] | 1 | 1.00 | ['missense_variant'] | MODERATE | FGFR3 | ENST00000340107.8:c.961G>A | ENSP00000339824.4:p.Val321Met | 2.60E-05 | 20 |
| 4 | 1802948 | ['G', 'A'] | 3 | 1.00 | ['missense_variant'] | MODERATE | FGFR3 | ENST00000340107.8:c.965G>A | ENSP00000339824.4:p.Arg322His | 8.68E-06 | 23 |
| 4 | 1802953 | ['C', 'T'] | 1 | 1.00 | ['missense_variant'] | MODERATE | FGFR3 | ENST00000340107.8:c.970C>T | ENSP00000339824.4:p.Arg324Cys | 1.30E-05 | 22 |
| 4 | 1802954 | ['G', 'A'] | 1 | 1.00 | ['missense_variant'] | MODERATE | FGFR3 | ENST00000340107.8:c.971G>A | ENSP00000339824.4:p.Arg324His | 1.73E-05 | 18 |
| 4 | 1802969 | ['C', 'T'] | 1 | 1.00 | ['missense_variant'] | MODERATE | FGFR3 | ENST00000340107.8:c.986C>T | ENSP00000339824.4:p.Ser329Leu | 3.07E-05 | 24 |
| 4 | 1802975 | ['G', 'A'] | 3 | 1.00 | ['missense_variant'] | MODERATE | FGFR3 | ENST00000340107.8:c.992G>A | ENSP00000339824.4:p.Arg331Gln | 2.19E-05 | 18 |
| 4 | 1802986 | ['G', 'A'] | 1 | 1.00 | ['missense_variant'] | MODERATE | FGFR3 | ENST00000340107.8:c.1003G>A | ENSP00000339824.4:p.Glu335Lys | 4.89E-05 | 20 |
| 4 | 1803005 | ['C', 'T'] | 1 | 1.00 | ['missense_variant'] | MODERATE | FGFR3 | ENST00000340107.8:c.1022C>T | ENSP00000339824.4:p.Thr341Ile | | 22 |
| 4 | 1803019 | ['G', 'A'] | 1 | 1.00 | ['missense_variant'] | MODERATE | FGFR3 | ENST00000340107.8:c.1036G>A | ENSP00000339824.4:p.Val346Met | 1.74E-05 | 22 |
| 4 | 1803046 | ['G', 'A'] | 3 | 1.00 | ['missense_variant'] | MODERATE | FGFR3 | ENST00000340107.8:c.1063G>A | ENSP00000339824.4:p.Val355Ile | 1.34E-05 | 24 |
| 4 | 1803052 | ['G', 'A'] | 1 | 1.00 | ['missense_variant'] | MODERATE | FGFR3 | ENST00000340107.8:c.1069G>A | ENSP00000339824.4:p.Gly357Arg | 2.25E-05 | 17 |
| 4 | 1803054 | ['G', 'GC'] | 3 | 1.00 | ['frameshift_variant' | HIGH | FGFR3 | ENST00000340107.8:c.1075dup | ENSP00000339824.4:p.Arg359ProfsTer11 | | |
| 4 | 1803058 | ['C', 'T'] | 1 | 1.00 | ['stop_gained'] | HIGH | FGFR3 | ENST00000340107.8:c.1075C>T | ENSP00000339824.4:p.Arg359Ter | 1.82E-05 | 39 |
| 4 | 1803059 | ['G', 'A'] | 5 | 1.00 | ['missense_variant'] | MODERATE | FGFR3 | ENST00000340107.8:c.1076G>A | ENSP00000339824.4:p.Arg359Gln | 3.64E-05 | 9 |
| 4 | 1803061 | ['G', 'A'] | 1 | 1.00 | ['missense_variant'] | MODERATE | FGFR3 | ENST00000340107.8:c.1078G>A | ENSP00000339824.4:p.Ala360Thr | | 18 |
| 4 | 1804332 | ['G', 'C'] | 5 | 1.00 | ['missense_variant', | MODERATE | FGFR3 | ENST00000340107.8:c.1084G>C | ENSP00000339824.4:p.Glu362Gln | 1.24E-05 | 15 |
| 4 | 1804353 | ['G', 'T'] | 1 | 1.00 | ['missense_variant'] | MODERATE | FGFR3 | ENST00000340107.8:c.1105G>T | ENSP00000339824.4:p.Asp369Tyr | | 20 |
| 4 | 1804360 | ['C', 'T'] | 4 | 1.00 | ['missense_variant'] | MODERATE | FGFR3 | ENST00000340107.8:c.1112C>T | ENSP00000339824.4:p.Ala371Val | 2.81E-05 | 18 |
| 4 | 1804375 | ['C', 'G'] | 1 | 1.00 | ['missense_variant'] | MODERATE | FGFR3 | ENST00000340107.8:c.1127C>G | ENSP00000339824.4:p.Ala376Gly | | 19 |
| 4 | 1804381 | ['T', 'G'] | 1 | 1.00 | ['missense_variant'] | MODERATE | FGFR3 | ENST00000340107.8:c.1133T>G | ENSP00000339824.4:p.Ile378Ser | | 26 |
| 4 | 1804383 | ['C', 'A'] | 1 | 1.00 | ['missense_variant'] | MODERATE | FGFR3 | ENST00000340107.8:c.1135C>A | ENSP00000339824.4:p.Leu379Ile | | 9 |
| 4 | 1804388 | ['C', 'A'] | 1 | 1.00 | ['missense_variant'] | MODERATE | FGFR3 | ENST00000340107.8:c.1140C>A | ENSP00000339824.4:p.Ser380Arg | | 20 |
| 4 | 1804401 | ['T', 'C'] | 2 | 1.00 | ['missense_variant'] | MODERATE | FGFR3 | ENST00000340107.8:c.1153T>C | ENSP00000339824.4:p.Phe385Leu | 7.99E-06 | 19 |
| 4 | 1804404 | ['T', 'A'] | 2 | 0.99 | ['missense_variant'] | MODERATE | FGFR3 | ENST00000340107.8:c.1156T>A | ENSP00000339824.4:p.Phe386Ile | 7.99E-06 | 18 |
| 4 | 1804413 | ['A', 'T'] | 1 | 1.00 | ['missense_variant'] | MODERATE | FGFR3 | ENST00000340107.8:c.1165A>T | ENSP00000339824.4:p.Ile389Phe | | 18 |
| 4 | 1804414 | ['T', 'A'] | 1 | 1.00 | ['missense_variant'] | MODERATE | FGFR3 | ENST00000340107.8:c.1166T>A | ENSP00000339824.4:p.Ile389Asn | | 24 |
| 4 | 1804423 | ['T', 'TGG( | 1 | 1.00 | ['inframe_insertion'] | MODERATE | FGFR3 | ENST00000340107.8:c.1179_1181dup | ENSP00000339824.4:p.Ala394dup | | |
| 4 | 1804443 | ['C', 'T'] | 1 | 1.00 | ['missense_variant'] | MODERATE | FGFR3 | ENST00000340107.8:c.1195C>T | ENSP00000339824.4:p.Arg399Cys | 3.21E-05 | 25 |
| 4 | 1804449 | ['C', 'T'] | 5 | 1.00 | ['missense_variant'] | MODERATE | FGFR3 | ENST00000340107.8:c.1201C>T | ENSP00000339824.4:p.Arg401Cys | 1.60E-05 | 23 |
| 4 | 1804455 | ['C', 'G'] | 4 | 1.00 | ['missense_variant'] | MODERATE | FGFR3 | ENST00000340107.8:c.1207C>G | ENSP00000339824.4:p.Pro403Ala | 2.40E-05 | 9 |
| 4 | 1804464 | ['A', 'G'] | 1 | 1.00 | ['missense_variant'] | MODERATE | FGFR3 | ENST00000340107.8:c.1216A>G | ENSP00000339824.4:p.Lys406Glu | 4.00E-06 | 23 |
| 4 | 1804486 | ['T', 'G'] | 2 | 1.00 | ['missense_variant'] | MODERATE | FGFR3 | ENST00000340107.8:c.1238T>G | ENSP00000339824.4:p.Val413Gly | | 31 |
| 4 | 1804492 | ['A', 'G'] | 1 | 1.00 | ['missense_variant'] | MODERATE | FGFR3 | ENST00000340107.8:c.1244A>G | ENSP00000339824.4:p.Lys415Arg | 8.01E-06 | 25 |
| 4 | 1804493 | ['G', 'C'] | 1 | 1.00 | ['missense_variant'] | MODERATE | FGFR3 | ENST00000340107.8:c.1245G>C | ENSP00000339824.4:p.Lys415Asn | 1.20E-05 | 26 |
| 4 | 1804496 | ['C', 'G'] | 7 | 1.00 | ['missense_variant'] | MODERATE | FGFR3 | ENST00000340107.8:c.1248C>G | ENSP00000339824.4:p.Ile416Met | | 20 |
| 4 | 1804516 | ['G', 'A'] | 3 | 1.00 | ['missense_variant'] | MODERATE | FGFR3 | ENST00000340107.8:c.1268G>A | ENSP00000339824.4:p.Arg423Gln | 2.41E-05 | 29 |
| 4 | 1804824 | ['G', 'C'] | 1 | 1.00 | ['missense_variant', | MODERATE | FGFR3 | ENST00000340107.8:c.1273G>C | ENSP00000339824.4:p.Val425Leu | 6.41E-06 | 28 |
| 4 | 1804828 | ['C', 'T'] | 2 | 1.00 | ['missense_variant'] | MODERATE | FGFR3 | ENST00000340107.8:c.1277C>T | ENSP00000339824.4:p.Ser426Phe | 1.28E-05 | 25 |
| 4 | 1804846 | ['C', 'T'] | 1 | 1.00 | ['missense_variant'] | MODERATE | FGFR3 | ENST00000340107.8:c.1295C>T | ENSP00000339824.4:p.Ser432Phe | | 29 |
| 4 | 1804872 | ['C', 'G'] | 6 | 1.00 | ['missense_variant'] | MODERATE | FGFR3 | ENST00000340107.8:c.1321C>G | ENSP00000339824.4:p.Arg441Gly | | 18 |
| 4 | 1804872 | ['C', 'T'] | 1 | 1.00 | ['missense_variant'] | MODERATE | FGFR3 | ENST00000340107.8:c.1321C>T | ENSP00000339824.4:p.Arg441Cys | 2.56E-05 | 23 |
| 4 | 1804873 | ['G', 'A'] | 3 | 1.00 | ['missense_variant'] | MODERATE | FGFR3 | ENST00000340107.8:c.1322G>A | ENSP00000339824.4:p.Arg441His | 3.84E-05 | 27 |

Figure 7 cont'd

Genetic variants found in the 5 Core genes

| chr | position | alleles | AC | variant_q | vep.consequence | vep.impact | vep.symbol | vep.hgvsc | vep.hgvsp | vep.gnom | vep.cadd_phred |
|---|---|---|---|---|---|---|---|---|---|---|---|
| 4 | 1804878 | ['G', 'A'] | 3 | 1.00 | ['missense_variant'] | MODERATE | FGFR3 | ENST00000340107.8:c.1327G>A | ENSP00000339824.4:p.Ala443Thr | 1.78E-05 | 11 |
| 4 | 1804888 | ['C', 'T'] | 1 | 1.00 | ['missense_variant'] | MODERATE | FGFR3 | ENST00000340107.8:c.1337C>T | ENSP00000339824.4:p.Ser446Phe | 2.56E-05 | 24 |
| 4 | 1804902 | ['C', 'G'] | 1 | 0.99 | ['missense_variant'] | MODERATE | FGFR3 | ENST00000340107.8:c.1351C>G | ENSP00000339824.4:p.Pro451Ala | | 20 |
| 4 | 1804906 | ['C', 'T'] | 4 | 1.00 | ['missense_variant'] | MODERATE | FGFR3 | ENST00000340107.8:c.1355C>T | ENSP00000339824.4:p.Thr452Met | 0.001288 | 6 |
| 4 | 1804911 | ['G', 'T'] | 2 | 1.00 | ['missense_variant'] | MODERATE | FGFR3 | ENST00000340107.8:c.1360G>T | ENSP00000339824.4:p.Ala454Ser | 2.56E-05 | 20 |
| 4 | 1804929 | ['G', 'C'] | 5 | 1.00 | ['missense_variant'] | MODERATE | FGFR3 | ENST00000340107.8:c.1378G>C | ENSP00000339824.4:p.Glu460Gln | 6.39E-06 | 26 |
| 4 | 1804941 | ['G', 'A'] | 1 | 1.00 | ['missense_variant'] | MODERATE | FGFR3 | ENST00000340107.8:c.1390G>A | ENSP00000339824.4:p.Asp464Asn | | 26 |
| 4 | 1804968 | ['C', 'G'] | 2 | 1.00 | ['missense_variant', | MODERATE | FGFR3 | ENST00000340107.8:c.1417C>G | ENSP00000339824.4:p.Arg473Gly | | 23 |
| 4 | 1805405 | ['T', 'C'] | 1 | 1.00 | ['missense_variant'] | MODERATE | FGFR3 | ENST00000340107.8:c.1469T>C | ENSP00000339824.4:p.Met490Thr | | 25 |
| 4 | 1805416 | ['A', 'G'] | 1 | 1.00 | ['missense_variant'] | MODERATE | FGFR3 | ENST00000340107.8:c.1480A>G | ENSP00000339824.4:p.Ile494Val | 4.03E-06 | 13 |
| 4 | 1805428 | ['A', 'G'] | 1 | 1.00 | ['missense_variant'] | MODERATE | FGFR3 | ENST00000340107.8:c.1492A>G | ENSP00000339824.4:p.Lys498Glu | 8.07E-06 | 29 |
| 4 | 1805434 | ['C', 'T'] | 1 | 1.00 | ['missense_variant'] | MODERATE | FGFR3 | ENST00000340107.8:c.1498C>T | ENSP00000339824.4:p.Arg500Trp | 8.09E-05 | 24 |
| 4 | 1805435 | ['G', 'A'] | 2 | 1.00 | ['missense_variant'] | MODERATE | FGFR3 | ENST00000340107.8:c.1499G>A | ENSP00000339824.4:p.Arg500Gln | 8.08E-06 | 23 |
| 4 | 1805440 | ['G', 'A'] | 4 | 1.00 | ['missense_variant'] | MODERATE | FGFR3 | ENST00000340107.8:c.1504G>A | ENSP00000339824.4:p.Ala502Thr | 5.66E-05 | 21 |
| 4 | 1805561 | ['G', 'A'] | 1 | 1.00 | ['missense_variant', | MODERATE | FGFR3 | ENST00000340107.8:c.1543G>A | ENSP00000339824.4:p.Asp515Asn | 4.79E-05 | 23 |
| 4 | 1805571 | ['A', 'C'] | 1 | 1.00 | ['missense_variant'] | MODERATE | FGFR3 | ENST00000340107.8:c.1553A>C | ENSP00000339824.4:p.Asp518Ala | 3.99E-06 | 27 |
| 4 | 1805571 | ['A', 'T'] | 1 | 1.00 | ['missense_variant'] | MODERATE | FGFR3 | ENST00000340107.8:c.1553A>T | ENSP00000339824.4:p.Asp518Val | | 27 |
| 4 | 1805573 | ['A', 'C'] | 1 | 1.00 | ['missense_variant'] | MODERATE | FGFR3 | ENST00000340107.8:c.1555A>C | ENSP00000339824.4:p.Lys519Gln | 1.20E-05 | 25 |
| 4 | 1805573 | ['A', 'G'] | 1 | 1.00 | ['missense_variant'] | MODERATE | FGFR3 | ENST00000340107.8:c.1555A>G | ENSP00000339824.4:p.Lys519Glu | 3.99E-06 | 23 |
| 4 | 1805574 | ['A', 'G'] | 3 | 1.00 | ['missense_variant'] | MODERATE | FGFR3 | ENST00000340107.8:c.1556A>G | ENSP00000339824.4:p.Lys519Arg | 5.58E-05 | 24 |
| 4 | 1805583 | ['C', 'T'] | 3 | 1.00 | ['missense_variant'] | MODERATE | FGFR3 | ENST00000340107.8:c.1565C>T | ENSP00000339824.4:p.Ser522Leu | 7.98E-06 | 25 |
| 4 | 1805636 | ['A', 'G'] | 3 | 1.00 | ['missense_variant'] | MODERATE | FGFR3 | ENST00000340107.8:c.1618A>G | ENSP00000339824.4:p.Ile540Val | 1.20E-05 | 22 |
| 4 | 1805642 | ['A', 'G'] | 1 | 1.00 | ['missense_variant'] | MODERATE | FGFR3 | ENST00000340107.8:c.1624A>G | ENSP00000339824.4:p.Asn542Asp | 3.99E-06 | 28 |
| 4 | 1805643 | ['A', 'G'] | 2 | 1.00 | ['missense_variant'] | MODERATE | FGFR3 | ENST00000340107.8:c.1625A>G | ENSP00000339824.4:p.Asn542Ser | 3.99E-06 | 26 |
| 4 | 1805649 | ['T', 'G'] | 2 | 1.00 | ['missense_variant'] | MODERATE | FGFR3 | ENST00000340107.8:c.1631T>G | ENSP00000339824.4:p.Leu544Arg | | 32 |
| 4 | 1805661 | ['C', 'T'] | 1 | 1.00 | ['missense_variant'] | MODERATE | FGFR3 | ENST00000340107.8:c.1643C>T | ENSP00000339824.4:p.Thr548Met | | 25 |
| 4 | 1805666 | ['G', 'A'] | 1 | 1.00 | ['missense_variant'] | MODERATE | FGFR3 | ENST00000340107.8:c.1648G>A | ENSP00000339824.4:p.Gly550Ser | | 25 |
| 4 | 1805761 | ['G', 'A'] | 2 | 1.00 | ['missense_variant'] | MODERATE | FGFR3 | ENST00000340107.8:c.1663G>A | ENSP00000339824.4:p.Val555Met | 0.000146 | 25 |
| 4 | 1805761 | ['G', 'C'] | 1 | 1.00 | ['missense_variant'] | MODERATE | FGFR3 | ENST00000340107.8:c.1663G>C | ENSP00000339824.4:p.Val555Leu | 4.05E-06 | 24 |
| 4 | 1805774 | ['A', 'G'] | 1 | 1.00 | ['missense_variant'] | MODERATE | FGFR3 | ENST00000340107.8:c.1676A>G | ENSP00000339824.4:p.Tyr559Cys | | 21 |
| 4 | 1805779 | ['G', 'C'] | 4 | 1.00 | ['missense_variant'] | MODERATE | FGFR3 | ENST00000340107.8:c.1681G>C | ENSP00000339824.4:p.Ala561Pro | 2.02E-05 | 23 |
| 4 | 1805807 | ['G', 'A'] | 1 | 1.00 | ['missense_variant'] | MODERATE | FGFR3 | ENST00000340107.8:c.1709G>A | ENSP00000339824.4:p.Arg570Gln | | 24 |
| 4 | 1805810 | ['C', 'T'] | 7 | 1.00 | ['missense_variant'] | MODERATE | FGFR3 | ENST00000340107.8:c.1712C>T | ENSP00000339824.4:p.Ala571Val | 0.00015 | 26 |
| 4 | 1805819 | ['C', 'T'] | 3 | 1.00 | ['missense_variant'] | MODERATE | FGFR3 | ENST00000340107.8:c.1721C>T | ENSP00000339824.4:p.Pro574Leu | 2.03E-05 | 25 |
| 4 | 1805822 | ['C', 'T'] | 6 | 1.00 | ['missense_variant'] | MODERATE | FGFR3 | ENST00000340107.8:c.1724C>T | ENSP00000339824.4:p.Pro575Leu | | 26 |
| 4 | 1805837 | ['C', 'T'] | 1 | 1.00 | ['missense_variant'] | MODERATE | FGFR3 | ENST00000340107.8:c.1739C>T | ENSP00000339824.4:p.Ser580Phe | 9.69E-05 | 24 |
| 4 | 1805860 | ['G', 'A'] | 3 | 1.00 | ['missense_variant'] | MODERATE | FGFR3 | ENST00000340107.8:c.1762G>A | ENSP00000339824.4:p.Glu588Lys | 6.83E-05 | 23 |
| 4 | 1805911 | ['C', 'T'] | 1 | 1.00 | ['missense_variant'] | MODERATE | FGFR3 | ENST00000340107.8:c.1813C>T | ENSP00000339824.4:p.Arg605Trp | 4.01E-06 | 25 |
| 4 | 1805920 | ['G', 'C'] | 1 | 1.00 | ['missense_variant'] | MODERATE | FGFR3 | ENST00000340107.8:c.1822G>C | ENSP00000339824.4:p.Glu608Gln | | 27 |
| 4 | 1805921 | ['A', 'G'] | 2 | 1.00 | ['missense_variant'] | MODERATE | FGFR3 | ENST00000340107.8:c.1823A>G | ENSP00000339824.4:p.Glu608Gly | 4.02E-06 | 33 |
| 4 | 1805929 | ['G', 'A'] | 1 | 1.00 | ['missense_variant'] | MODERATE | FGFR3 | ENST00000340107.8:c.1831G>A | ENSP00000339824.4:p.Ala611Thr | 4.03E-06 | 33 |
| 4 | 1805930 | ['C', 'T'] | 3 | 1.00 | ['missense_variant'] | MODERATE | FGFR3 | ENST00000340107.8:c.1832C>T | ENSP00000339824.4:p.Ala611Val | 2.42E-05 | 25 |
| 4 | 1805933 | ['C', 'A'] | 5 | 1.00 | ['missense_variant'] | MODERATE | FGFR3 | ENST00000340107.8:c.1835C>A | ENSP00000339824.4:p.Ser612Tyr | 1.21E-05 | 27 |
| 4 | 1806093 | ['G', 'A'] | 6 | 1.00 | ['missense_variant'] | MODERATE | FGFR3 | ENST00000340107.8:c.1885G>A | ENSP00000339824.4:p.Glu629Lys | 0.00018 | 33 |
| 4 | 1806169 | ['C', 'G'] | 4 | 1.00 | ['missense_variant'] | MODERATE | FGFR3 | ENST00000340107.8:c.1961C>G | ENSP00000339824.4:p.Thr654Ser | 8.04E-06 | 20 |
| 4 | 1806281 | ['G', 'C'] | 1 | 1.00 | ['missense_variant'] | MODERATE | FGFR3 | ENST00000340107.8:c.1990G>C | ENSP00000339824.4:p.Ala664Pro | 4.04E-06 | 33 |
| 4 | 1806290 | ['G', 'T'] | 1 | 1.00 | ['missense_variant'] | MODERATE | FGFR3 | ENST00000340107.8:c.1999G>T | ENSP00000339824.4:p.Ala667Ser | 1.21E-05 | 25 |
| 4 | 1806300 | ['ACC', 'A'] | 1 | 1.00 | ['frameshift_variant' | HIGH | FGFR3 | ENST00000340107.8:c.2010_2011del | ENSP00000339824.4:p.Asp670GlufsTer8 | | |
| 4 | 1806315 | ['A', 'G'] | 1 | 1.00 | ['missense_variant'] | MODERATE | FGFR3 | ENST00000340107.8:c.2024A>G | ENSP00000339824.4:p.His675Arg | | 25 |
| 4 | 1806326 | ['G', 'A'] | 1 | 1.00 | ['missense_variant', | MODERATE | FGFR3 | ENST00000340107.8:c.2035G>A | ENSP00000339824.4:p.Val679Ile | 4.02E-06 | 27 |
| 4 | 1806548 | ['G', 'T'] | 1 | 1.00 | ['missense_variant', | MODERATE | FGFR3 | ENST00000340107.8:c.2039G>T | ENSP00000339824.4:p.Trp680Leu | | 34 |
| 4 | 1806581 | ['C', 'T'] | 2 | 1.00 | ['missense_variant'] | MODERATE | FGFR3 | ENST00000340107.8:c.2072C>T | ENSP00000339824.4:p.Thr691Met | 4.00E-06 | 26 |
| 4 | 1806593 | ['C', 'T'] | 6 | 1.00 | ['missense_variant'] | MODERATE | FGFR3 | ENST00000340107.8:c.2084C>T | ENSP00000339824.4:p.Ser695Phe | 1.20E-05 | 25 |
| 4 | 1806619 | ['G', 'A'] | 1 | 1.00 | ['missense_variant'] | MODERATE | FGFR3 | ENST00000340107.8:c.2110G>A | ENSP00000339824.4:p.Glu704Lys | 4.00E-06 | 27 |
| 4 | 1806668 | ['A', 'G'] | 5 | 1.00 | ['missense_variant'] | MODERATE | FGFR3 | ENST00000340107.8:c.2159A>G | ENSP00000339824.4:p.Asn720Ser | 6.81E-05 | 23 |
| 4 | 1806669 | ['C', 'G'] | 1 | 1.00 | ['missense_variant'] | MODERATE | FGFR3 | ENST00000340107.8:c.2160C>G | ENSP00000339824.4:p.Asn720Lys | | 24 |
| 4 | 1806842 | ['C', 'T'] | 1 | 1.00 | ['missense_variant'] | MODERATE | FGFR3 | ENST00000340107.8:c.2188C>T | ENSP00000339824.4:p.Arg730Trp | 4.20E-06 | 23 |
| 4 | 1806843 | ['G', 'A'] | 5 | 1.00 | ['missense_variant'] | MODERATE | FGFR3 | ENST00000340107.8:c.2189G>A | ENSP00000339824.4:p.Arg730Gln | 3.35E-05 | 26 |
| 4 | 1806855 | ['A', 'G'] | 2 | 1.00 | ['missense_variant'] | MODERATE | FGFR3 | ENST00000340107.8:c.2201A>G | ENSP00000339824.4:p.His734Arg | 4.12E-06 | 21 |
| 4 | 1806860 | ['G', 'A'] | 1 | 1.00 | ['missense_variant'] | MODERATE | FGFR3 | ENST00000340107.8:c.2206G>A | ENSP00000339824.4:p.Ala736Thr | 4.93E-05 | 22 |
| 4 | 1806861 | ['C', 'T'] | 1 | 1.00 | ['missense_variant'] | MODERATE | FGFR3 | ENST00000340107.8:c.2207C>T | ENSP00000339824.4:p.Ala736Val | 3.29E-05 | 3 |
| 4 | 1806876 | ['C', 'T'] | 1 | 1.00 | ['missense_variant'] | MODERATE | FGFR3 | ENST00000340107.8:c.2222C>T | ENSP00000339824.4:p.Pro741Leu | | 26 |

Figure 7 cont'd

Genetic variants found in the 5 Core genes

| chr | position | alleles | AC | variant_q | vep.consequence | vep.impact | vep.symbol | vep.hgvsc | vep.hgvsp | vep.gnom | vep.cadd_phred |
|---|---|---|---|---|---|---|---|---|---|---|---|
| 4 | 1806935 | ['G', 'A'] | 2 | 1.00 | ['splice_donor_variar | HIGH | FGFR3 | ENST00000340107.8:c.2280+1G>A | | 4.58E-06 | 25 |
| 4 | 1807132 | ['C', 'T'] | 7 | 1.00 | ['missense_variant'] | MODERATE | FGFR3 | ENST00000340107.8:c.2297C>T | ENSP00000339824.4:p.Ser766Leu | 5.47E-05 | 27 |
| 4 | 1807135 | ['C', 'T'] | 5 | 1.00 | ['missense_variant'] | MODERATE | FGFR3 | ENST00000340107.8:c.2300C>T | ENSP00000339824.4:p.Ala767Val | 6.36E-05 | 13 |
| 4 | 1807156 | ['C', 'T'] | 2 | 1.00 | ['missense_variant'] | MODERATE | FGFR3 | ENST00000340107.8:c.2321C>T | ENSP00000339824.4:p.Pro774Leu | 1.84E-05 | 24 |
| 4 | 1807159 | ['G', 'A'] | 3 | 1.00 | ['missense_variant'] | MODERATE | FGFR3 | ENST00000340107.8:c.2324G>A | ENSP00000339824.4:p.Gly775Asp | 3.19E-05 | 22 |
| 4 | 1807165 | ['A', 'G'] | 1 | 1.00 | ['missense_variant'] | MODERATE | FGFR3 | ENST00000340107.8:c.2330A>G | ENSP00000339824.4:p.Gln777Arg | 4.50E-06 | 20 |
| 4 | 1807191 | ['G', 'C'] | 2 | 1.00 | ['missense_variant'] | MODERATE | FGFR3 | ENST00000340107.8:c.2356G>C | ENSP00000339824.4:p.Gly786Arg | | 24 |
| 4 | 1807194 | ['G', 'GA'] | 1 | 1.00 | ['frameshift_variant' | HIGH | FGFR3 | ENST00000340107.8:c.2360dup | ENSP00000339824.4:p.Asp787GlufsTer32 | | |
| 4 | 1807197 | ['G', 'A'] | 1 | 1.00 | ['missense_variant'] | MODERATE | FGFR3 | ENST00000340107.8:c.2362G>A | ENSP00000339824.4:p.Asp788Asn | 8.61E-06 | 27 |
| 4 | 1807201 | ['CCGT', 'C | 1 | 1.00 | ['inframe_deletion'] | MODERATE | FGFR3 | ENST00000340107.8:c.2367_2369del | ENSP00000339824.4:p.Val790del | | |
| 4 | 1807204 | ['T', 'C'] | 2 | 1.00 | ['missense_variant'] | MODERATE | FGFR3 | ENST00000340107.8:c.2369T>C | ENSP00000339824.4:p.Val790Ala | | 27 |
| 4 | 1807230 | ['G', 'A'] | 1 | 1.00 | ['missense_variant'] | MODERATE | FGFR3 | ENST00000340107.8:c.2395G>A | ENSP00000339824.4:p.Ala799Thr | | 17 |
| 4 | 1807237 | ['C', 'T'] | 1 | 1.00 | ['missense_variant'] | MODERATE | FGFR3 | ENST00000340107.8:c.2402C>T | ENSP00000339824.4:p.Pro801Leu | 8.24E-05 | 22 |
| 4 | 1807254 | ['C', 'T'] | 5 | 1.00 | ['missense_variant'] | MODERATE | FGFR3 | ENST00000340107.8:c.2419C>T | ENSP00000339824.4:p.Arg807Trp | 1.83E-05 | 14 |
| 4 | 1807255 | ['G', 'A'] | 2 | 1.00 | ['missense_variant'] | MODERATE | FGFR3 | ENST00000340107.8:c.2420G>A | ENSP00000339824.4:p.Arg807Gln | 2.79E-05 | 15 |
| 4 | 1807258 | ['C', 'A'] | 2 | 1.00 | ['missense_variant'] | MODERATE | FGFR3 | ENST00000340107.8:c.2423C>A | ENSP00000339824.4:p.Thr808Lys | 4.67E-06 | 24 |
| 9 | 35792461 | ['G', 'A'] | 2 | 1.00 | ['missense_variant'] | MODERATE | NPR2 | ENST00000342694.6:c.53G>A | ENSP00000341083.2:p.Arg18His | | 23 |
| 9 | 35792469 | ['G', 'C'] | 1 | 1.00 | ['missense_variant'] | MODERATE | NPR2 | ENST00000342694.6:c.61G>C | ENSP00000341083.2:p.Gly21Arg | | 19 |
| 9 | 35792475 | ['C', 'T'] | 1 | 1.00 | ['missense_variant'] | MODERATE | NPR2 | ENST00000342694.6:c.67C>T | ENSP00000341083.2:p.Arg23Trp | | 24 |
| 9 | 35792580 | ['C', 'T'] | 1 | 1.00 | ['missense_variant'] | MODERATE | NPR2 | ENST00000342694.6:c.172C>T | ENSP00000341083.2:p.Arg58Trp | 3.99E-06 | 25 |
| 9 | 35792581 | ['G', 'T'] | 1 | 1.00 | ['missense_variant'] | MODERATE | NPR2 | ENST00000342694.6:c.173G>T | ENSP00000341083.2:p.Arg58Leu | 1.20E-05 | 23 |
| 9 | 35792583 | ['G', 'A'] | 2 | 1.00 | ['missense_variant'] | MODERATE | NPR2 | ENST00000342694.6:c.175G>A | ENSP00000341083.2:p.Ala59Thr | | 21 |
| 9 | 35792601 | ['C', 'T'] | 1 | 1.00 | ['missense_variant'] | MODERATE | NPR2 | ENST00000342694.6:c.193C>T | ENSP00000341083.2:p.Arg65Trp | 7.97E-06 | 23 |
| 9 | 35792652 | ['C', 'A'] | 1 | 1.00 | ['missense_variant'] | MODERATE | NPR2 | ENST00000342694.6:c.244C>A | ENSP00000341083.2:p.Leu82Met | 2.39E-05 | 23 |
| 9 | 35792688 | ['G', 'A'] | 1 | 1.00 | ['missense_variant'] | MODERATE | NPR2 | ENST00000342694.6:c.280G>A | ENSP00000341083.2:p.Asp94Asn | 7.96E-06 | 19 |
| 9 | 35792709 | ['T', 'G'] | 1 | 1.00 | ['missense_variant'] | MODERATE | NPR2 | ENST00000342694.6:c.301T>G | ENSP00000341083.2:p.Cys101Gly | | 27 |
| 9 | 35792713 | ['T', 'C'] | 1 | 1.00 | ['missense_variant'] | MODERATE | NPR2 | ENST00000342694.6:c.305T>C | ENSP00000341083.2:p.Val102Ala | | 20 |
| 9 | 35792736 | ['C', 'G'] | 1 | 1.00 | ['missense_variant'] | MODERATE | NPR2 | ENST00000342694.6:c.328C>G | ENSP00000341083.2:p.Arg110Gly | | 27 |
| 9 | 35792818 | ['G', 'A'] | 1 | 1.00 | ['missense_variant'] | MODERATE | NPR2 | ENST00000342694.6:c.410G>A | ENSP00000341083.2:p.Arg137His | | 21 |
| 9 | 35792833 | ['C', 'T'] | 1 | 1.00 | ['missense_variant'] | MODERATE | NPR2 | ENST00000342694.6:c.425C>T | ENSP00000341083.2:p.Thr142Ile | | 21 |
| 9 | 35792839 | ['C', 'T'] | 1 | 1.00 | ['missense_variant'] | MODERATE | NPR2 | ENST00000342694.6:c.431C>T | ENSP00000341083.2:p.Pro144Leu | | 24 |
| 9 | 35792883 | ['C', 'T'] | 1 | 1.00 | ['missense_variant'] | MODERATE | NPR2 | ENST00000342694.6:c.475C>T | ENSP00000341083.2:p.His159Tyr | | 22 |
| 9 | 35792885 | ['C', 'G'] | 2 | 1.00 | ['missense_variant'] | MODERATE | NPR2 | ENST00000342694.6:c.477C>G | ENSP00000341083.2:p.His159Gln | | 19 |
| 9 | 35792890 | ['A', 'G'] | 5 | 1.00 | ['missense_variant'] | MODERATE | NPR2 | ENST00000342694.6:c.482A>G | ENSP00000341083.2:p.Asn161Ser | 1.59E-05 | 23 |
| 9 | 35792899 | ['C', 'T'] | 1 | 1.00 | ['missense_variant'] | MODERATE | NPR2 | ENST00000342694.6:c.491C>T | ENSP00000341083.2:p.Ala164Val | | 17 |
| 9 | 35792901 | ['C', 'T'] | 2 | 1.00 | ['missense_variant'] | MODERATE | NPR2 | ENST00000342694.6:c.493C>T | ENSP00000341083.2:p.Arg165Cys | 3.98E-06 | 26 |
| 9 | 35792928 | ['C', 'T'] | 1 | 1.00 | ['missense_variant'] | MODERATE | NPR2 | ENST00000342694.6:c.520C>T | ENSP00000341083.2:p.Arg174Cys | 3.98E-06 | 27 |
| 9 | 35792992 | ['A', 'G'] | 1 | 1.00 | ['missense_variant'] | MODERATE | NPR2 | ENST00000342694.6:c.584A>G | ENSP00000341083.2:p.Asn195Ser | 7.99E-06 | 23 |
| 9 | 35793021 | ['C', 'T'] | 1 | 1.00 | ['stop_gained'] | HIGH | NPR2 | ENST00000342694.6:c.613C>T | ENSP00000341083.2:p.Arg205Ter | | 35 |
| 9 | 35793022 | ['G', 'A'] | 1 | 1.00 | ['missense_variant'] | MODERATE | NPR2 | ENST00000342694.6:c.614G>A | ENSP00000341083.2:p.Arg205Gln | | 20 |
| 9 | 35793033 | ['G', 'A'] | 2 | 1.00 | ['missense_variant'] | MODERATE | NPR2 | ENST00000342694.6:c.625G>A | ENSP00000341083.2:p.Gly209Ser | 4.09E-06 | 21 |
| 9 | 35793039 | ['G', 'A'] | 3 | 1.00 | ['missense_variant'] | MODERATE | NPR2 | ENST00000342694.6:c.631G>A | ENSP00000341083.2:p.Glu211Lys | 4.13E-06 | 21 |
| 9 | 35793904 | ['A', 'C'] | 1 | 1.00 | ['missense_variant'] | MODERATE | NPR2 | ENST00000342694.6:c.674A>C | ENSP00000341083.2:p.Tyr225Ser | | 24 |
| 9 | 35793906 | ['A', 'G'] | 1 | 1.00 | ['missense_variant'] | MODERATE | NPR2 | ENST00000342694.6:c.676A>G | ENSP00000341083.2:p.Ile226Val | 1.19E-05 | 21 |
| 9 | 35793952 | ['A', 'T'] | 1 | 1.00 | ['missense_variant'] | MODERATE | NPR2 | ENST00000342694.6:c.722A>T | ENSP00000341083.2:p.Gln241Leu | | 21 |
| 9 | 35793955 | ['G', 'A'] | 6 | 1.00 | ['missense_variant'] | MODERATE | NPR2 | ENST00000342694.6:c.725G>A | ENSP00000341083.2:p.Arg242Lys | 2.78E-05 | 21 |
| 9 | 35793980 | ['T', 'A'] | 1 | 1.00 | ['stop_gained'] | HIGH | NPR2 | ENST00000342694.6:c.750T>A | ENSP00000341083.2:p.Tyr250Ter | | 35 |
| 9 | 35794018 | ['G', 'A'] | 2 | 1.00 | ['missense_variant'] | MODERATE | NPR2 | ENST00000342694.6:c.788G>A | ENSP00000341083.2:p.Arg263His | 3.58E-05 | 24 |
| 9 | 35794024 | ['G', 'A'] | 1 | 1.00 | ['missense_variant'] | MODERATE | NPR2 | ENST00000342694.6:c.794G>A | ENSP00000341083.2:p.Gly265Asp | | 20 |
| 9 | 35794029 | ['A', 'G'] | 1 | 1.00 | ['missense_variant'] | MODERATE | NPR2 | ENST00000342694.6:c.799A>G | ENSP00000341083.2:p.Thr267Ala | 2.39E-05 | 21 |
| 9 | 35794044 | ['C', 'T'] | 2 | 1.00 | ['missense_variant'] | MODERATE | NPR2 | ENST00000342694.6:c.814C>T | ENSP00000341083.2:p.Arg272Trp | 2.78E-05 | 24 |
| 9 | 35794045 | ['G', 'A'] | 1 | 1.00 | ['missense_variant'] | MODERATE | NPR2 | ENST00000342694.6:c.815G>A | ENSP00000341083.2:p.Arg272Gln | 1.19E-05 | 20 |
| 9 | 35794056 | ['G', 'C'] | 1 | 1.00 | ['missense_variant'] | MODERATE | NPR2 | ENST00000342694.6:c.826G>C | ENSP00000341083.2:p.Asp276His | 3.98E-06 | 24 |
| 9 | 35794060 | ['A', 'G'] | 2 | 1.00 | ['missense_variant'] | MODERATE | NPR2 | ENST00000342694.6:c.830A>G | ENSP00000341083.2:p.Asn277Ser | 4.38E-05 | 21 |
| 9 | 35794063 | ['G', 'A'] | 1 | 1.00 | ['missense_variant'] | MODERATE | NPR2 | ENST00000342694.6:c.833G>A | ENSP00000341083.2:p.Arg278His | 2.79E-05 | 22 |
| 9 | 35794068 | ['C', 'T'] | 3 | 1.00 | ['missense_variant'] | MODERATE | NPR2 | ENST00000342694.6:c.838C>T | ENSP00000341083.2:p.Arg280Trp | 1.20E-05 | 24 |
| 9 | 35794093 | ['A', 'G'] | 1 | 1.00 | ['missense_variant'] | MODERATE | NPR2 | ENST00000342694.6:c.863A>G | ENSP00000341083.2:p.Glu288Gly | 1.20E-05 | 25 |
| 9 | 35799630 | ['A', 'G'] | 1 | 1.00 | ['missense_variant'] | MODERATE | NPR2 | ENST00000342694.6:c.886A>G | ENSP00000341083.2:p.Ile296Val | | 19 |
| 9 | 35799634 | ['C', 'T'] | 2 | 1.00 | ['missense_variant'] | MODERATE | NPR2 | ENST00000342694.6:c.890C>T | ENSP00000341083.2:p.Thr297Met | 3.98E-06 | 26 |
| 9 | 35799645 | ['C', 'T'] | 1 | 1.00 | ['missense_variant'] | MODERATE | NPR2 | ENST00000342694.6:c.901C>T | ENSP00000341083.2:p.Pro301Ser | | 25 |
| 9 | 35799660 | ['T', 'G'] | 1 | 1.00 | ['missense_variant'] | MODERATE | NPR2 | ENST00000342694.6:c.916T>G | ENSP00000341083.2:p.Tyr306Asp | | 28 |
| 9 | 35799679 | ['G', 'C'] | 1 | 1.00 | ['missense_variant'] | MODERATE | NPR2 | ENST00000342694.6:c.935G>C | ENSP00000341083.2:p.Arg312Pro | | 24 |

Figure 7 cont'd

Genetic variants found in the 5 Core genes

| chr | position | alleles | AC | variant_q | vep.consequence | vep.impact | vep.symbol | vep.hgvsc | vep.hgvsp | vep.gnomі | vep.cadd_phred |
|---|---|---|---|---|---|---|---|---|---|---|---|
| 9 | 35799697 | ['G', 'A'] | 7 | 1.00 | ['missense_variant'] | MODERATE | NPR2 | ENST00000342694.6:c.953G>A | ENSP00000341083.2:p.Arg318Gln | 7.95E-05 | 22 |
| 9 | 35799699 | ['G', 'C'] | 2 | 1.00 | ['missense_variant'] | MODERATE | NPR2 | ENST00000342694.6:c.955G>C | ENSP00000341083.2:p.Glu319Gln | | 17 |
| 9 | 35799714 | ['G', 'C'] | 1 | 1.00 | ['missense_variant'] | MODERATE | NPR2 | ENST00000342694.6:c.970G>C | ENSP00000341083.2:p.Glu324Gln | 1.19E-05 | 22 |
| 9 | 35799715 | ['A', 'T'] | 1 | 1.00 | ['missense_variant'] | MODERATE | NPR2 | ENST00000342694.6:c.971A>T | ENSP00000341083.2:p.Glu324Val | | 23 |
| 9 | 35800041 | ['G', 'GCTT | 1 | 1.00 | ['inframe_insertion'] | MODERATE | NPR2 | ENST00000342694.6:c.1010_1012dup | ENSP00000341083.2:p.Phe337dup | 3.98E-06 | |
| 9 | 35800104 | ['C', 'T'] | 1 | 1.00 | ['missense_variant'] | MODERATE | NPR2 | ENST00000342694.6:c.1070C>T | ENSP00000341083.2:p.Thr357Ile | 5.17E-05 | 21 |
| 9 | 35800110 | ['A', 'C'] | 2 | 1.00 | ['missense_variant'] | MODERATE | NPR2 | ENST00000342694.6:c.1076A>C | ENSP00000341083.2:p.Glu359Ala | | 19 |
| 9 | 35800122 | ['G', 'A'] | 4 | 1.00 | ['missense_variant'] | MODERATE | NPR2 | ENST00000342694.6:c.1088G>A | ENSP00000341083.2:p.Arg363Gln | 5.57E-05 | 22 |
| 9 | 35800124 | ['AT', 'A'] | 3 | 1.00 | ['frameshift_variant' | HIGH | NPR2 | ENST00000342694.6:c.1092del | ENSP00000341083.2:p.Ile364MetfsTer13 | 7.95E-06 | |
| 9 | 35800133 | ['A', 'G'] | 1 | 1.00 | ['missense_variant'] | MODERATE | NPR2 | ENST00000342694.6:c.1099A>G | ENSP00000341083.2:p.Lys367Glu | | 24 |
| 9 | 35800142 | ['G', 'A'] | 2 | 1.00 | ['missense_variant'] | MODERATE | NPR2 | ENST00000342694.6:c.1108G>A | ENSP00000341083.2:p.Gly370Arg | 1.19E-05 | 24 |
| 9 | 35800427 | ['C', 'T'] | 2 | 1.00 | ['stop_gained'] | HIGH | NPR2 | ENST00000342694.6:c.1162C>T | ENSP00000341083.2:p.Arg388Ter | 1.19E-05 | 35 |
| 9 | 35800720 | ['C', 'G'] | 1 | 1.00 | ['missense_variant'] | MODERATE | NPR2 | ENST00000342694.6:c.1230C>G | ENSP00000341083.2:p.His410Gln | | 18 |
| 9 | 35800733 | ['G', 'A'] | 4 | 1.00 | ['missense_variant'] | MODERATE | NPR2 | ENST00000342694.6:c.1243G>A | ENSP00000341083.2:p.Glu415Lys | | 21 |
| 9 | 35800752 | ['C', 'T'] | 7 | 1.00 | ['missense_variant'] | MODERATE | NPR2 | ENST00000342694.6:c.1262C>T | ENSP00000341083.2:p.Thr421Met | 7.16E-05 | 21 |
| 9 | 35800757 | ['C', 'T'] | 6 | 1.00 | ['missense_variant'] | MODERATE | NPR2 | ENST00000342694.6:c.1267C>T | ENSP00000341083.2:p.Arg423Trp | 2.39E-05 | 24 |
| 9 | 35800758 | ['G', 'A'] | 1 | 1.00 | ['missense_variant'] | MODERATE | NPR2 | ENST00000342694.6:c.1268G>A | ENSP00000341083.2:p.Arg423Gln | 1.19E-05 | 22 |
| 9 | 35800782 | ['C', 'T'] | 2 | 1.00 | ['missense_variant'] | MODERATE | NPR2 | ENST00000342694.6:c.1292C>T | ENSP00000341083.2:p.Ala431Val | | 12 |
| 9 | 35800791 | ['C', 'T'] | 2 | 1.00 | ['missense_variant'] | MODERATE | NPR2 | ENST00000342694.6:c.1301C>T | ENSP00000341083.2:p.Ser434Leu | 1.99E-05 | 15 |
| 9 | 35800803 | ['C', 'A'] | 1 | 1.00 | ['missense_variant'] | MODERATE | NPR2 | ENST00000342694.6:c.1313C>A | ENSP00000341083.2:p.Pro438His | | 23 |
| 9 | 35800814 | ['G', 'A'] | 2 | 1.00 | ['missense_variant'] | MODERATE | NPR2 | ENST00000342694.6:c.1324G>A | ENSP00000341083.2:p.Asp442Asn | 3.98E-06 | 23 |
| 9 | 35800815 | ['A', 'G'] | 1 | 1.00 | ['missense_variant'] | MODERATE | NPR2 | ENST00000342694.6:c.1325A>G | ENSP00000341083.2:p.Asp442Gly | 3.98E-06 | 24 |
| 9 | 35801090 | ['A', 'G'] | 1 | 1.00 | ['missense_variant'] | MODERATE | NPR2 | ENST00000342694.6:c.1372A>G | ENSP00000341083.2:p.Ile458Val | 2.39E-05 | 21 |
| 9 | 35801091 | ['T', 'C'] | 1 | 1.00 | ['missense_variant'] | MODERATE | NPR2 | ENST00000342694.6:c.1373T>C | ENSP00000341083.2:p.Ile458Thr | 7.95E-06 | 24 |
| 9 | 35801118 | ['T', 'G'] | 1 | 1.00 | ['missense_variant'] | MODERATE | NPR2 | ENST00000342694.6:c.1400T>G | ENSP00000341083.2:p.Phe467Cys | | 25 |
| 9 | 35801125 | ['G', 'A'] | 3 | 1.00 | ['missense_variant'] | MODERATE | NPR2 | ENST00000342694.6:c.1407G>A | ENSP00000341083.2:p.Met469Ile | 1.99E-05 | 16 |
| 9 | 35801154 | ['G', 'A'] | 1 | 1.00 | ['missense_variant', | MODERATE | NPR2 | ENST00000342694.6:c.1436G>A | ENSP00000341083.2:p.Arg479Gln | 7.96E-06 | 35 |
| 9 | 35801646 | ['G', 'C'] | 3 | 1.00 | ['missense_variant'] | MODERATE | NPR2 | ENST00000342694.6:c.1440G>C | ENSP00000341083.2:p.Lys480Asn | 1.59E-05 | 23 |
| 9 | 35801684 | ['G', 'A'] | 4 | 1.00 | ['missense_variant'] | MODERATE | NPR2 | ENST00000342694.6:c.1478G>A | ENSP00000341083.2:p.Arg493His | 7.96E-06 | 33 |
| 9 | 35801722 | ['C', 'T'] | 1 | 1.00 | ['missense_variant'] | MODERATE | NPR2 | ENST00000342694.6:c.1516C>T | ENSP00000341083.2:p.Arg506Cys | 1.59E-05 | 24 |
| 9 | 35801723 | ['G', 'A'] | 2 | 1.00 | ['missense_variant'] | MODERATE | NPR2 | ENST00000342694.6:c.1517G>A | ENSP00000341083.2:p.Arg506His | 0.000119 | 28 |
| 9 | 35801728 | ['C', 'G'] | 2 | 1.00 | ['missense_variant'] | MODERATE | NPR2 | ENST00000342694.6:c.1522C>G | ENSP00000341083.2:p.His508Asp | 3.98E-06 | 22 |
| 9 | 35801744 | ['G', 'A'] | 1 | 1.00 | ['missense_variant'] | MODERATE | NPR2 | ENST00000342694.6:c.1538G>A | ENSP00000341083.2:p.Ser513Asn | | 29 |
| 9 | 35801759 | ['C', 'T'] | 2 | 1.00 | ['missense_variant'] | MODERATE | NPR2 | ENST00000342694.6:c.1553C>T | ENSP00000341083.2:p.Ser518Leu | 7.95E-06 | 25 |
| 9 | 35801932 | ['T', 'C'] | 1 | 1.00 | ['missense_variant'] | MODERATE | NPR2 | ENST00000342694.6:c.1564T>C | ENSP00000341083.2:p.Ser522Pro | | 31 |
| 9 | 35801941 | ['G', 'A'] | 1 | 1.00 | ['missense_variant'] | MODERATE | NPR2 | ENST00000342694.6:c.1573G>A | ENSP00000341083.2:p.Gly525Ser | | 24 |
| 9 | 35801989 | ['G', 'A'] | 2 | 1.00 | ['missense_variant'] | MODERATE | NPR2 | ENST00000342694.6:c.1621G>A | ENSP00000341083.2:p.Gly541Ser | 0.000151 | 32 |
| 9 | 35802209 | ['A', 'T'] | 6 | 1.00 | ['missense_variant'] | MODERATE | NPR2 | ENST00000342694.6:c.1636A>T | ENSP00000341083.2:p.Asn546Tyr | 3.18E-05 | 27 |
| 9 | 35802218 | ['G', 'A'] | 2 | 1.00 | ['missense_variant'] | MODERATE | NPR2 | ENST00000342694.6:c.1645G>A | ENSP00000341083.2:p.Ala549Thr | 1.19E-05 | 30 |
| 9 | 35802230 | ['G', 'C'] | 1 | 1.00 | ['missense_variant'] | MODERATE | NPR2 | ENST00000342694.6:c.1657G>C | ENSP00000341083.2:p.Val553Leu | | 22 |
| 9 | 35802246 | ['T', 'C'] | 1 | 1.00 | ['missense_variant'] | MODERATE | NPR2 | ENST00000342694.6:c.1673T>C | ENSP00000341083.2:p.Ile558Thr | 7.97E-06 | 27 |
| 9 | 35802249 | ['A', 'G'] | 1 | 1.00 | ['missense_variant'] | MODERATE | NPR2 | ENST00000342694.6:c.1676A>G | ENSP00000341083.2:p.Glu559Gly | | 29 |
| 9 | 35802263 | ['G', 'C'] | 1 | 1.00 | ['missense_variant'] | MODERATE | NPR2 | ENST00000342694.6:c.1690G>C | ENSP00000341083.2:p.Val564Leu | | 23 |
| 9 | 35802545 | ['G', 'A'] | 1 | 1.00 | ['missense_variant'] | MODERATE | NPR2 | ENST00000342694.6:c.1753G>A | ENSP00000341083.2:p.Ala585Thr | 3.98E-06 | 28 |
| 9 | 35802609 | ['T', 'G'] | 1 | 1.00 | ['splice_donor_variar | HIGH | NPR2 | ENST00000342694.6:c.1815+2T>G | | | 34 |
| 9 | 35802749 | ['C', 'G'] | 1 | 1.00 | ['missense_variant'] | MODERATE | NPR2 | ENST00000342694.6:c.1833C>G | ENSP00000341083.2:p.Asp611Glu | | 18 |
| 9 | 35802761 | ['G', 'C'] | 2 | 1.00 | ['missense_variant'] | MODERATE | NPR2 | ENST00000342694.6:c.1845G>C | ENSP00000341083.2:p.Leu615Phe | | 27 |
| 9 | 35802774 | ['C', 'T'] | 4 | 1.00 | ['missense_variant'] | MODERATE | NPR2 | ENST00000342694.6:c.1858C>T | ENSP00000341083.2:p.Arg620Cys | 3.98E-06 | 28 |
| 9 | 35802802 | ['A', 'G'] | 1 | 1.00 | ['missense_variant', | MODERATE | NPR2 | ENST00000342694.6:c.1886A>G | ENSP00000341083.2:p.Lys629Arg | | 28 |
| 9 | 35805565 | ['T', 'G'] | 1 | 1.00 | ['missense_variant'] | MODERATE | NPR2 | ENST00000342694.6:c.1942T>G | ENSP00000341083.2:p.Ser648Ala | | 26 |
| 9 | 35805638 | ['C', 'T'] | 1 | 1.00 | ['missense_variant'] | MODERATE | NPR2 | ENST00000342694.6:c.2015C>T | ENSP00000341083.2:p.Ala672Val | | 16 |
| 9 | 35805648 | ['T', 'A'] | 2 | 1.00 | ['missense_variant'] | MODERATE | NPR2 | ENST00000342694.6:c.2025T>A | ENSP00000341083.2:p.Asp675Glu | | 17 |
| 9 | 35805656 | ['A', 'G'] | 1 | 1.00 | ['missense_variant'] | MODERATE | NPR2 | ENST00000342694.6:c.2033A>G | ENSP00000341083.2:p.His678Arg | | 24 |
| 9 | 35805661 | ['C', 'T'] | 1 | 1.00 | ['missense_variant'] | MODERATE | NPR2 | ENST00000342694.6:c.2038C>T | ENSP00000341083.2:p.Leu680Phe | 3.98E-06 | 21 |
| 9 | 35805664 | ['T', 'C'] | 1 | 1.00 | ['missense_variant'] | MODERATE | NPR2 | ENST00000342694.6:c.2041T>C | ENSP00000341083.2:p.Tyr681His | | 25 |
| 9 | 35805833 | ['A', 'C'] | 1 | 1.00 | ['missense_variant'] | MODERATE | NPR2 | ENST00000342694.6:c.2051A>C | ENSP00000341083.2:p.Lys684Thr | | 27 |
| 9 | 35805844 | ['G', 'T'] | 3 | 1.00 | ['missense_variant'] | MODERATE | NPR2 | ENST00000342694.6:c.2062G>T | ENSP00000341083.2:p.Ala688Ser | 7.96E-06 | 25 |
| 9 | 35805869 | ['C', 'T'] | 1 | 1.00 | ['missense_variant'] | MODERATE | NPR2 | ENST00000342694.6:c.2087C>T | ENSP00000341083.2:p.Pro696Leu | 3.98E-06 | 16 |
| 9 | 35805873 | ['G', 'T'] | 1 | 1.00 | ['missense_variant'] | MODERATE | NPR2 | ENST00000342694.6:c.2091G>T | ENSP00000341083.2:p.Leu697Phe | 3.98E-06 | 19 |
| 9 | 35805895 | ['G', 'A'] | 1 | 1.00 | ['missense_variant'] | MODERATE | NPR2 | ENST00000342694.6:c.2113G>A | ENSP00000341083.2:p.Ala705Thr | 3.98E-06 | 28 |
| 9 | 35805901 | ['G', 'A'] | 1 | 1.00 | ['missense_variant'] | MODERATE | NPR2 | ENST00000342694.6:c.2119G>A | ENSP00000341083.2:p.Val707Ile | 1.99E-05 | 22 |
| 9 | 35805932 | ['T', 'C'] | 1 | 1.00 | ['missense_variant'] | MODERATE | NPR2 | ENST00000342694.6:c.2150T>C | ENSP00000341083.2:p.Ile717Thr | 1.20E-05 | 28 |

Figure 7 cont'd

Genetic variants found in the 5 Core genes

| chr | position | alleles | AC | variant_q | vep.consequence | vep.impact | vep.symbol | vep.hgvsc | vep.hgvsp | vep.gnom: | vep.cadd_phred |
|---|---|---|---|---|---|---|---|---|---|---|---|
| 9 | 35805941 | ['G', 'A'] | 1 | 1.00 | ['missense_variant'] | MODERATE | NPR2 | ENST00000342694.6:c.2159G>A | ENSP00000341083.2:p.Arg720His | 2.39E-05 | 32 |
| 9 | 35805945 | ['T', 'A'] | 3 | 1.00 | ['missense_variant'] | MODERATE | NPR2 | ENST00000342694.6:c.2163T>A | ENSP00000341083.2:p.Ser721Arg | 7.97E-06 | 18 |
| 9 | 35805961 | ['G', 'C'] | 1 | 1.00 | ['missense_variant'] | MODERATE | NPR2 | ENST00000342694.6:c.2179G>C | ENSP00000341083.2:p.Glu727Gln | | 24 |
| 9 | 35806069 | ['T', 'G'] | 1 | 1.00 | ['missense_variant'] | MODERATE | NPR2 | ENST00000342694.6:c.2208T>G | ENSP00000341083.2:p.Ile736Met | 7.95E-06 | 24 |
| 9 | 35806090 | ['TCAG', 'T | 1 | 1.00 | ['inframe_deletion'] | MODERATE | NPR2 | ENST00000342694.6:c.2231_2233del | ENSP00000341083.2:p.Gln744del | | |
| 9 | 35806095 | ['G', 'A'] | 3 | 1.00 | ['missense_variant'] | MODERATE | NPR2 | ENST00000342694.6:c.2234G>A | ENSP00000341083.2:p.Arg745Gln | 2.39E-05 | 22 |
| 9 | 35806103 | ['T', 'A'] | 1 | 1.00 | ['missense_variant'] | MODERATE | NPR2 | ENST00000342694.6:c.2242T>A | ENSP00000341083.2:p.Phe748Ile | | 27 |
| 9 | 35806121 | ['C', 'T'] | 3 | 1.00 | ['missense_variant'] | MODERATE | NPR2 | ENST00000342694.6:c.2260C>T | ENSP00000341083.2:p.Arg754Trp | 7.95E-05 | 24 |
| 9 | 35806129 | ['A', 'C'] | 2 | 1.00 | ['missense_variant'] | MODERATE | NPR2 | ENST00000342694.6:c.2268A>C | ENSP00000341083.2:p.Gln756His | | 15 |
| 9 | 35806157 | ['G', 'C'] | 4 | 1.00 | ['missense_variant'] | MODERATE | NPR2 | ENST00000342694.6:c.2296G>C | ENSP00000341083.2:p.Glu766Gln | 7.95E-06 | 21 |
| 9 | 35806161 | ['G', 'A'] | 1 | 1.00 | ['missense_variant'] | MODERATE | NPR2 | ENST00000342694.6:c.2300G>A | ENSP00000341083.2:p.Arg767Gln | 1.19E-05 | 26 |
| 9 | 35806187 | ['C', 'T'] | 1 | 1.00 | ['missense_variant'] | MODERATE | NPR2 | ENST00000342694.6:c.2326C>T | ENSP00000341083.2:p.Arg776Trp | 7.96E-06 | 26 |
| 9 | 35806220 | ['C', 'T'] | 1 | 1.00 | ['missense_variant'] | MODERATE | NPR2 | ENST00000342694.6:c.2359C>T | ENSP00000341083.2:p.Arg787Trp | 0.000291 | 28 |
| 9 | 35806221 | ['G', 'C'] | 2 | 1.00 | ['missense_variant'] | MODERATE | NPR2 | ENST00000342694.6:c.2360G>C | ENSP00000341083.2:p.Arg787Pro | | 28 |
| 9 | 35806221 | ['G', 'A'] | 1 | 1.00 | ['missense_variant'] | MODERATE | NPR2 | ENST00000342694.6:c.2360G>A | ENSP00000341083.2:p.Arg787Gln | 3.98E-06 | 27 |
| 9 | 35806223 | ['C', 'T'] | 1 | 1.00 | ['missense_variant'] | MODERATE | NPR2 | ENST00000342694.6:c.2362C>T | ENSP00000341083.2:p.Arg788Cys | 2.79E-05 | 27 |
| 9 | 35806429 | ['C', 'T'] | 1 | 1.00 | ['missense_variant'] | MODERATE | NPR2 | ENST00000342694.6:c.2410C>T | ENSP00000341083.2:p.Arg804Cys | 3.98E-06 | 28 |
| 9 | 35806448 | ['A', 'T'] | 1 | 1.00 | ['missense_variant'] | MODERATE | NPR2 | ENST00000342694.6:c.2429A>T | ENSP00000341083.2:p.Asn810Ile | | 25 |
| 9 | 35806474 | ['C', 'T'] | 1 | 1.00 | ['missense_variant'] | MODERATE | NPR2 | ENST00000342694.6:c.2455C>T | ENSP00000341083.2:p.Arg819Cys | 1.99E-05 | 27 |
| 9 | 35806501 | ['C', 'T'] | 1 | 1.00 | ['missense_variant'] | MODERATE | NPR2 | ENST00000342694.6:c.2482C>T | ENSP00000341083.2:p.Arg828Cys | | 29 |
| 9 | 35806506 | ['G', 'C'] | 1 | 1.00 | ['missense_variant'] | MODERATE | NPR2 | ENST00000342694.6:c.2487G>C | ENSP00000341083.2:p.Lys829Asn | | 25 |
| 9 | 35807045 | ['C', 'T'] | 1 | 1.00 | ['missense_variant'] | MODERATE | NPR2 | ENST00000342694.6:c.2542C>T | ENSP00000341083.2:p.Arg848Trp | 1.59E-05 | 24 |
| 9 | 35807053 | ['G', 'C'] | 3 | 1.00 | ['missense_variant'] | MODERATE | NPR2 | ENST00000342694.6:c.2550G>C | ENSP00000341083.2:p.Glu850Asp | 3.98E-06 | 24 |
| 9 | 35807085 | ['C', 'T'] | 1 | 1.00 | ['missense_variant'] | MODERATE | NPR2 | ENST00000342694.6:c.2582C>T | ENSP00000341083.2:p.Thr861Ile | | 27 |
| 9 | 35807129 | ['G', 'A'] | 1 | 1.00 | ['missense_variant'] | MODERATE | NPR2 | ENST00000342694.6:c.2626G>A | ENSP00000341083.2:p.Glu876Lys | | 31 |
| 9 | 35807144 | ['C', 'G'] | 2 | 1.00 | ['missense_variant', | MODERATE | NPR2 | ENST00000342694.6:c.2641C>G | ENSP00000341083.2:p.Gln881Glu | | 23 |
| 9 | 35808509 | ['G', 'A'] | 1 | 1.00 | ['missense_variant', | MODERATE | NPR2 | ENST00000342694.6:c.2713G>A | ENSP00000341083.2:p.Val905Met | 4.02E-06 | 35 |
| 9 | 35808519 | ['T', 'C'] | 3 | 1.00 | ['missense_variant'] | MODERATE | NPR2 | ENST00000342694.6:c.2723T>C | ENSP00000341083.2:p.Ile908Thr | 6.42E-05 | 29 |
| 9 | 35808545 | ['G', 'C'] | 1 | 1.00 | ['missense_variant'] | MODERATE | NPR2 | ENST00000342694.6:c.2749G>C | ENSP00000341083.2:p.Gly917Arg | | 32 |
| 9 | 35808558 | ['G', 'A'] | 1 | 1.00 | ['missense_variant'] | MODERATE | NPR2 | ENST00000342694.6:c.2762G>A | ENSP00000341083.2:p.Arg921Gln | 1.20E-05 | 33 |
| 9 | 35808591 | ['G', 'A'] | 7 | 1.00 | ['missense_variant'] | MODERATE | NPR2 | ENST00000342694.6:c.2795G>A | ENSP00000341083.2:p.Arg932His | 3.19E-05 | 29 |
| 9 | 35808608 | ['C', 'G'] | 1 | 1.00 | ['missense_variant'] | MODERATE | NPR2 | ENST00000342694.6:c.2812C>G | ENSP00000341083.2:p.Leu938Val | | 24 |
| 9 | 35808613 | ['T', 'A'] | 1 | 1.00 | ['missense_variant'] | MODERATE | NPR2 | ENST00000342694.6:c.2817T>A | ENSP00000341083.2:p.Asp939Glu | | 17 |
| 9 | 35808621 | ['C', 'A'] | 1 | 1.00 | ['missense_variant'] | MODERATE | NPR2 | ENST00000342694.6:c.2825C>A | ENSP00000341083.2:p.Ser942Tyr | | 18 |
| 9 | 35808629 | ['C', 'T'] | 1 | 1.00 | ['missense_variant'] | MODERATE | NPR2 | ENST00000342694.6:c.2833C>T | ENSP00000341083.2:p.Arg945Cys | 3.18E-05 | 25 |
| 9 | 35808644 | ['C', 'A'] | 1 | 1.00 | ['missense_variant'] | MODERATE | NPR2 | ENST00000342694.6:c.2848C>A | ENSP00000341083.2:p.Pro950Thr | | 26 |
| 9 | 35808663 | ['T', 'A'] | 3 | 1.00 | ['missense_variant'] | MODERATE | NPR2 | ENST00000342694.6:c.2867T>A | ENSP00000341083.2:p.Leu956Gln | 1.99E-05 | 32 |
| 9 | 35808665 | ['C', 'T'] | 1 | 1.00 | ['missense_variant'] | MODERATE | NPR2 | ENST00000342694.6:c.2869C>T | ENSP00000341083.2:p.Arg957Cys | 1.19E-05 | 31 |
| 9 | 35808669 | ['T', 'C'] | 1 | 1.00 | ['missense_variant'] | MODERATE | NPR2 | ENST00000342694.6:c.2873T>C | ENSP00000341083.2:p.Ile958Thr | 7.95E-06 | 29 |
| 9 | 35809177 | ['C', 'A'] | 1 | 1.00 | ['missense_variant'] | MODERATE | NPR2 | ENST00000342694.6:c.3008C>A | ENSP00000341083.2:p.Ser1003Tyr | | 25 |
| 9 | 35809180 | ['C', 'T'] | 4 | 1.00 | ['missense_variant'] | MODERATE | NPR2 | ENST00000342694.6:c.3011C>T | ENSP00000341083.2:p.Thr1004Ile | 2.39E-05 | 24 |
| 9 | 35809186 | ['A', 'C'] | 1 | 1.00 | ['missense_variant'] | MODERATE | NPR2 | ENST00000342694.6:c.3017A>C | ENSP00000341083.2:p.Lys1006Thr | 3.98E-06 | 27 |
| 9 | 35809194 | ['C', 'G'] | 2 | 1.00 | ['missense_variant'] | MODERATE | NPR2 | ENST00000342694.6:c.3025C>G | ENSP00000341083.2:p.Leu1009Val | | 24 |
| 9 | 35809206 | ['G', 'A'] | 1 | 1.00 | ['missense_variant'] | MODERATE | NPR2 | ENST00000342694.6:c.3037G>A | ENSP00000341083.2:p.Gly1013Arg | | 28 |
| 9 | 35809227 | ['CGG', 'C' | 1 | 1.00 | ['frameshift_variant' | HIGH | NPR2 | ENST00000342694.6:c.3063_3064del | ENSP00000341083.2:p.Asp1022CysfsTer35 | | |
| 9 | 35809244 | ['G', 'A'] | 1 | 1.00 | ['missense_variant'] | MODERATE | NPR2 | ENST00000342694.6:c.3075G>A | ENSP00000341083.2:p.Met1025Ile | 1.19E-05 | 24 |
| 9 | 35809395 | ['C', 'T'] | 2 | 1.00 | ['stop_gained'] | HIGH | NPR2 | ENST00000342694.6:c.3094C>T | ENSP00000341083.2:p.Arg1032Ter | | 40 |
| 9 | 35809396 | ['G', 'A'] | 3 | 1.00 | ['missense_variant'] | MODERATE | NPR2 | ENST00000342694.6:c.3095G>A | ENSP00000341083.2:p.Arg1032Gln | 3.18E-05 | 24 |
| 9 | 35809413 | ['G', 'A'] | 1 | 1.00 | ['missense_variant'] | MODERATE | NPR2 | ENST00000342694.6:c.3112G>A | ENSP00000341083.2:p.Gly1038Arg | | 29 |
| 9 | 35809419 | ['C', 'T'] | 7 | 1.00 | ['missense_variant'] | MODERATE | NPR2 | ENST00000342694.6:c.3118C>T | ENSP00000341083.2:p.Arg1040Trp | 3.18E-05 | 25 |
| 9 | 35809420 | ['G', 'A'] | 6 | 1.00 | ['missense_variant'] | MODERATE | NPR2 | ENST00000342694.6:c.3119G>A | ENSP00000341083.2:p.Arg1040Gln | 7.56E-05 | 19 |
| 9 | 35809428 | ['C', 'T'] | 1 | 1.00 | ['missense_variant'] | MODERATE | NPR2 | ENST00000342694.6:c.3127C>T | ENSP00000341083.2:p.Pro1043Ser | | 18 |
| 9 | 35809434 | ['G', 'A'] | 1 | 1.00 | ['missense_variant'] | MODERATE | NPR2 | ENST00000342694.6:c.3133G>A | ENSP00000341083.2:p.Gly1045Arg | | 37 |
| 9 | 35809436 | ['AC', 'A'] | 1 | 1.00 | ['frameshift_variant' | HIGH | NPR2 | ENST00000342694.6:c.3136del | ENSP00000341083.2:p.Leu1046SerfsTer? | | |
| 9 | 35809441 | ['T', 'C'] | 1 | 1.00 | ['missense_variant'] | MODERATE | NPR2 | ENST00000342694.6:c.3140T>C | ENSP00000341083.2:p.Leu1047Pro | | 25 |
| 15 | 98649583 | ['T', 'C'] | 1 | 1.00 | ['start_lost'] | HIGH | IGF1R | ENST00000650285.1:c.2T>C | ENSP00000497069.1:p.Met1? | | 23 |
| 15 | 98649597 | ['G', 'A'] | 3 | 1.00 | ['missense_variant'] | MODERATE | IGF1R | ENST00000650285.1:c.16G>A | ENSP00000497069.1:p.Gly6Arg | 0.000605 | 22 |
| 15 | 98649609 | ['C', 'T'] | 1 | 1.00 | ['missense_variant'] | MODERATE | IGF1R | ENST00000650285.1:c.28C>T | ENSP00000497069.1:p.Pro10Ser | 1.21E-05 | 21 |
| 15 | 98649610 | ['C', 'T'] | 1 | 1.00 | ['missense_variant'] | MODERATE | IGF1R | ENST00000650285.1:c.29C>T | ENSP00000497069.1:p.Pro10Leu | 4.05E-06 | 20 |
| 15 | 98649636 | ['C', 'G'] | 1 | 1.00 | ['missense_variant'] | MODERATE | IGF1R | ENST00000650285.1:c.55C>G | ENSP00000497069.1:p.Leu19Val | 1.21E-05 | 15 |
| 15 | 98649636 | ['C', 'T'] | 1 | 1.00 | ['missense_variant'] | MODERATE | IGF1R | ENST00000650285.1:c.55C>T | ENSP00000497069.1:p.Leu19Phe | 1.62E-05 | 15 |
| 15 | 98649640 | ['C', 'T'] | 1 | 1.00 | ['missense_variant'] | MODERATE | IGF1R | ENST00000650285.1:c.59C>T | ENSP00000497069.1:p.Ser20Phe | 3.24E-05 | 20 |

Figure 7 cont'd

Genetic variants found in the 5 Core genes

| chr | position | alleles | AC | variant_q | vep.consequence | vep.impact | vep.symbol | vep.hgvsc | vep.hgvsp | vep.gnom: | vep.cadd_phred |
|---|---|---|---|---|---|---|---|---|---|---|---|
| 15 | 98649652 | ['C', 'G'] | 1 | 1.00 | ['missense_variant'] | MODERATE | IGF1R | ENST00000650285.1:c.71C>G | ENSP00000497069.1:p.Ser24Trp | 4.05E-06 | 21 |
| 15 | 98649654 | ['C', 'T'] | 1 | 1.00 | ['missense_variant'] | MODERATE | IGF1R | ENST00000650285.1:c.73C>T | ENSP00000497069.1:p.Leu25Phe | | 21 |
| 15 | 98649661 | ['C', 'T'] | 1 | 1.00 | ['missense_variant'] | MODERATE | IGF1R | ENST00000650285.1:c.80C>T | ENSP00000497069.1:p.Pro27Leu | 1.62E-05 | 23 |
| 15 | 98649674 | ['AAGTG', | 1 | 1.00 | ['splice_donor_variar | HIGH | IGF1R | ENST00000650285.1:c.94+3_94+6del | | 3.64E-05 | |
| 15 | 98707651 | ['C', 'A'] | 1 | 1.00 | ['missense_variant'] | MODERATE | IGF1R | ENST00000650285.1:c.184C>A | ENSP00000497069.1:p.Leu62Met | | 25 |
| 15 | 98707667 | ['C', 'G'] | 1 | 1.00 | ['missense_variant'] | MODERATE | IGF1R | ENST00000650285.1:c.200C>G | ENSP00000497069.1:p.Ala67Gly | | 19 |
| 15 | 98707679 | ['G', 'A'] | 2 | 1.00 | ['missense_variant'] | MODERATE | IGF1R | ENST00000650285.1:c.212G>A | ENSP00000497069.1:p.Arg71His | 2.39E-05 | 25 |
| 15 | 98707703 | ['C', 'T'] | 2 | 1.00 | ['missense_variant'] | MODERATE | IGF1R | ENST00000650285.1:c.236C>T | ENSP00000497069.1:p.Thr79Met | 1.59E-05 | 26 |
| 15 | 98707808 | ['A', 'G'] | 1 | 1.00 | ['missense_variant'] | MODERATE | IGF1R | ENST00000650285.1:c.341A>G | ENSP00000497069.1:p.Asn114Ser | | 23 |
| 15 | 98707838 | ['A', 'G'] | 1 | 1.00 | ['missense_variant'] | MODERATE | IGF1R | ENST00000650285.1:c.371A>G | ENSP00000497069.1:p.Asn124Ser | 1.59E-05 | 19 |
| 15 | 98707849 | ['A', 'G'] | 2 | 1.00 | ['missense_variant'] | MODERATE | IGF1R | ENST00000650285.1:c.382A>G | ENSP00000497069.1:p.Ile128Val | 3.98E-06 | 22 |
| 15 | 98707868 | ['G', 'A'] | 1 | 1.00 | ['missense_variant'] | MODERATE | IGF1R | ENST00000650285.1:c.401G>A | ENSP00000497069.1:p.Arg134Lys | 3.98E-06 | 21 |
| 15 | 98707958 | ['T', 'G'] | 1 | 1.00 | ['missense_variant'] | MODERATE | IGF1R | ENST00000650285.1:c.491T>G | ENSP00000497069.1:p.Val164Gly | | 22 |
| 15 | 98707976 | ['T', 'C'] | 2 | 1.00 | ['missense_variant'] | MODERATE | IGF1R | ENST00000650285.1:c.509T>C | ENSP00000497069.1:p.Val170Ala | 3.98E-06 | 23 |
| 15 | 98708024 | ['TGGA', '1 | 1 | 1.00 | ['inframe_deletion'] | MODERATE | IGF1R | ENST00000650285.1:c.562_564del | ENSP00000497069.1:p.Glu188del | | |
| 15 | 98708072 | ['A', 'G'] | 2 | 1.00 | ['missense_variant'] | MODERATE | IGF1R | ENST00000650285.1:c.605A>G | ENSP00000497069.1:p.Asn202Ser | 0.000137 | 17 |
| 15 | 98891348 | ['C', 'T'] | 1 | 1.00 | ['missense_variant'] | MODERATE | IGF1R | ENST00000650285.1:c.664C>T | ENSP00000497069.1:p.Arg222Trp | 0.00011 | 23 |
| 15 | 98891352 | ['C', 'T'] | 1 | 1.00 | ['missense_variant'] | MODERATE | IGF1R | ENST00000650285.1:c.668C>T | ENSP00000497069.1:p.Ala223Val | 4.05E-06 | 23 |
| 15 | 98891390 | ['C', 'G'] | 1 | 1.00 | ['missense_variant'] | MODERATE | IGF1R | ENST00000650285.1:c.706C>G | ENSP00000497069.1:p.Leu236Val | | 24 |
| 15 | 98891405 | ['G', 'A'] | 2 | 1.00 | ['missense_variant'] | MODERATE | IGF1R | ENST00000650285.1:c.721G>A | ENSP00000497069.1:p.Ala241Thr | 8.00E-06 | 16 |
| 15 | 98891417 | ['G', 'A'] | 3 | 1.00 | ['missense_variant'] | MODERATE | IGF1R | ENST00000650285.1:c.733G>A | ENSP00000497069.1:p.Asp245Asn | 4.00E-06 | 18 |
| 15 | 98891420 | ['A', 'G'] | 6 | 1.00 | ['missense_variant'] | MODERATE | IGF1R | ENST00000650285.1:c.736A>G | ENSP00000497069.1:p.Thr246Ala | 2.80E-05 | 17 |
| 15 | 98891439 | ['G', 'A'] | 4 | 1.00 | ['missense_variant'] | MODERATE | IGF1R | ENST00000650285.1:c.755G>A | ENSP00000497069.1:p.Arg252His | 2.79E-05 | 22 |
| 15 | 98891469 | ['C', 'G'] | 1 | 1.00 | ['missense_variant'] | MODERATE | IGF1R | ENST00000650285.1:c.785C>G | ENSP00000497069.1:p.Pro262Arg | | 15 |
| 15 | 98891478 | ['C', 'T'] | 1 | 1.00 | ['missense_variant'] | MODERATE | IGF1R | ENST00000650285.1:c.794C>T | ENSP00000497069.1:p.Pro265Leu | 7.96E-06 | 26 |
| 15 | 98891484 | ['A', 'C'] | 1 | 1.00 | ['missense_variant'] | MODERATE | IGF1R | ENST00000650285.1:c.800A>C | ENSP00000497069.1:p.Asn267Thr | 1.99E-05 | 16 |
| 15 | 98891540 | ['C', 'G'] | 1 | 1.00 | ['missense_variant'] | MODERATE | IGF1R | ENST00000650285.1:c.856C>G | ENSP00000497069.1:p.Leu286Val | | 13 |
| 15 | 98891564 | ['G', 'A'] | 1 | 1.00 | ['missense_variant'] | MODERATE | IGF1R | ENST00000650285.1:c.880G>A | ENSP00000497069.1:p.Glu294Lys | 8.09E-06 | 17 |
| 15 | 98891606 | ['C', 'T'] | 1 | 1.00 | ['missense_variant'] | MODERATE | IGF1R | ENST00000650285.1:c.922C>T | ENSP00000497069.1:p.Pro308Ser | | 26 |
| 15 | 98891622 | ['G', 'A'] | 1 | 1.00 | ['missense_variant'] | MODERATE | IGF1R | ENST00000650285.1:c.938G>A | ENSP00000497069.1:p.Arg313His | 4.18E-06 | 24 |
| 15 | 98891625 | ['A', 'G'] | 1 | 1.00 | ['missense_variant'] | MODERATE | IGF1R | ENST00000650285.1:c.941A>G | ENSP00000497069.1:p.Asn314Ser | | 18 |
| 15 | 98891628 | ['G', 'A'] | 1 | 1.00 | ['missense_variant'] | MODERATE | IGF1R | ENST00000650285.1:c.944G>A | ENSP00000497069.1:p.Gly315Asp | | 12 |
| 15 | 98891633 | ['C', 'G'] | 1 | 1.00 | ['missense_variant'] | MODERATE | IGF1R | ENST00000650285.1:c.949C>G | ENSP00000497069.1:p.Gln317Glu | | 16 |
| 15 | 98896760 | ['G', 'A'] | 1 | 1.00 | ['missense_variant'] | MODERATE | IGF1R | ENST00000650285.1:c.957G>A | ENSP00000497069.1:p.Met319Ile | | 23 |
| 15 | 98896789 | ['C', 'T'] | 1 | 1.00 | ['missense_variant'] | MODERATE | IGF1R | ENST00000650285.1:c.986C>T | ENSP00000497069.1:p.Pro329Leu | 7.96E-06 | 23 |
| 15 | 98896794 | ['G', 'A'] | 3 | 1.00 | ['missense_variant'] | MODERATE | IGF1R | ENST00000650285.1:c.991G>A | ENSP00000497069.1:p.Val331Ile | 1.99E-05 | 21 |
| 15 | 98896816 | ['C', 'G'] | 2 | 1.00 | ['missense_variant'] | MODERATE | IGF1R | ENST00000650285.1:c.1013C>G | ENSP00000497069.1:p.Thr338Arg | | 17 |
| 15 | 98896829 | ['T', 'G'] | 1 | 1.00 | ['missense_variant'] | MODERATE | IGF1R | ENST00000650285.1:c.1026T>G | ENSP00000497069.1:p.Asp342Glu | | 22 |
| 15 | 98896879 | ['A', 'G'] | 1 | 1.00 | ['missense_variant'] | MODERATE | IGF1R | ENST00000650285.1:c.1076A>G | ENSP00000497069.1:p.Asn359Ser | 1.59E-05 | 23 |
| 15 | 98896884 | ['C', 'T'] | 1 | 1.00 | ['missense_variant'] | MODERATE | IGF1R | ENST00000650285.1:c.1081C>T | ENSP00000497069.1:p.Leu361Phe | 3.98E-06 | 22 |
| 15 | 98896897 | ['G', 'A'] | 1 | 1.00 | ['missense_variant'] | MODERATE | IGF1R | ENST00000650285.1:c.1094G>A | ENSP00000497069.1:p.Arg365Gln | | 33 |
| 15 | 98896899 | ['C', 'T'] | 1 | 1.00 | ['missense_variant'] | MODERATE | IGF1R | ENST00000650285.1:c.1096C>T | ENSP00000497069.1:p.Arg366Trp | 1.19E-05 | 24 |
| 15 | 98899488 | ['T', 'A'] | 1 | 1.00 | ['missense_variant'] | MODERATE | IGF1R | ENST00000650285.1:c.1114T>A | ENSP00000497069.1:p.Ser372Thr | | 22 |
| 15 | 98899518 | ['G', 'A'] | 1 | 1.00 | ['missense_variant'] | MODERATE | IGF1R | ENST00000650285.1:c.1144G>A | ENSP00000497069.1:p.Glu382Lys | | 28 |
| 15 | 98899536 | ['G', 'A'] | 4 | 1.00 | ['missense_variant'] | MODERATE | IGF1R | ENST00000650285.1:c.1162G>A | ENSP00000497069.1:p.Val388Met | 0.000577 | 26 |
| 15 | 98899542 | ['A', 'G'] | 1 | 1.00 | ['missense_variant'] | MODERATE | IGF1R | ENST00000650285.1:c.1168A>G | ENSP00000497069.1:p.Ile390Val | | 23 |
| 15 | 98899568 | ['C', 'CT'] | 1 | 1.00 | ['frameshift_variant' | HIGH | IGF1R | ENST00000650285.1:c.1196dup | ENSP00000497069.1:p.Leu399PhefsTer71 | 3.98E-06 | |
| 15 | 98899591 | ['G', 'A'] | 7 | 1.00 | ['missense_variant'] | MODERATE | IGF1R | ENST00000650285.1:c.1217G>A | ENSP00000497069.1:p.Arg406His | 3.18E-05 | 24 |
| 15 | 98908740 | ['G', 'A'] | 1 | 1.00 | ['missense_variant'] | MODERATE | IGF1R | ENST00000650285.1:c.1303G>A | ENSP00000497069.1:p.Asp435Asn | 7.96E-06 | 22 |
| 15 | 98908800 | ['T', 'C'] | 1 | 1.00 | ['missense_variant'] | MODERATE | IGF1R | ENST00000650285.1:c.1363T>C | ENSP00000497069.1:p.Cys455Arg | | 28 |
| 15 | 98908818 | ['C', 'T'] | 2 | 1.00 | ['missense_variant'] | MODERATE | IGF1R | ENST00000650285.1:c.1381C>T | ENSP00000497069.1:p.Arg461Cys | | 28 |
| 15 | 98908819 | ['G', 'A'] | 4 | 1.00 | ['missense_variant'] | MODERATE | IGF1R | ENST00000650285.1:c.1382G>A | ENSP00000497069.1:p.Arg461His | 1.99E-05 | 23 |
| 15 | 98908834 | ['C', 'T'] | 2 | 1.00 | ['missense_variant'] | MODERATE | IGF1R | ENST00000650285.1:c.1397C>T | ENSP00000497069.1:p.Thr466Met | 3.98E-06 | 27 |
| 15 | 98908848 | ['C', 'T'] | 3 | 1.00 | ['missense_variant'] | MODERATE | IGF1R | ENST00000650285.1:c.1411C>T | ENSP00000497069.1:p.Arg471Cys | 1.20E-05 | 27 |
| 15 | 98908849 | ['G', 'A'] | 4 | 1.00 | ['missense_variant'] | MODERATE | IGF1R | ENST00000650285.1:c.1412G>A | ENSP00000497069.1:p.Arg471His | 4.78E-05 | 25 |
| 15 | 98911326 | ['G', 'A'] | 1 | 1.00 | ['missense_variant'] | MODERATE | IGF1R | ENST00000650285.1:c.1474G>A | ENSP00000497069.1:p.Val492Ile | 0.000569 | 17 |
| 15 | 98911333 | ['A', 'T'] | 2 | 1.00 | ['missense_variant'] | MODERATE | IGF1R | ENST00000650285.1:c.1481A>T | ENSP00000497069.1:p.His494Leu | 3.98E-06 | 24 |
| 15 | 98911354 | ['C', 'T'] | 1 | 1.00 | ['missense_variant'] | MODERATE | IGF1R | ENST00000650285.1:c.1502C>T | ENSP00000497069.1:p.Ser501Leu | 0.000358 | 15 |
| 15 | 98911357 | ['A', 'G'] | 1 | 1.00 | ['missense_variant'] | MODERATE | IGF1R | ENST00000650285.1:c.1505A>G | ENSP00000497069.1:p.Lys502Arg | | 23 |
| 15 | 98911362 | ['C', 'T'] | 4 | 1.00 | ['missense_variant'] | MODERATE | IGF1R | ENST00000650285.1:c.1510C>T | ENSP00000497069.1:p.Arg504Cys | 1.19E-05 | 28 |
| 15 | 98911383 | ['C', 'T'] | 2 | 1.00 | ['missense_variant'] | MODERATE | IGF1R | ENST00000650285.1:c.1531C>T | ENSP00000497069.1:p.Arg511Trp | 2.39E-05 | 25 |
| 15 | 98911390 | ['G', 'A'] | 1 | 1.00 | ['missense_variant'] | MODERATE | IGF1R | ENST00000650285.1:c.1538G>A | ENSP00000497069.1:p.Arg513Gln | 7.95E-06 | 23 |

Figure 7 cont'd

Genetic variants found in the 5 Core genes

| chr | position | alleles | AC | variant_q | vep.consequence | vep.impact | vep.symbol | vep.hgvsc | vep.hgvsp | vep.gnom: | vep.cadd_phred |
|---|---|---|---|---|---|---|---|---|---|---|---|
| 15 | 98911414 | ['T', 'C'] | 1 | 1.00 | ['missense_variant'] | MODERATE | IGF1R | ENST00000650285.1:c.1562T>C | ENSP00000497069.1:p.Ile521Thr | | 25 |
| 15 | 98911417 | ['G', 'C'] | 1 | 1.00 | ['missense_variant'] | MODERATE | IGF1R | ENST00000650285.1:c.1565G>C | ENSP00000497069.1:p.Ser522Thr | 3.98E-06 | 23 |
| 15 | 98911425 | ['G', 'A'] | 2 | 1.00 | ['missense_variant'] | MODERATE | IGF1R | ENST00000650285.1:c.1573G>A | ENSP00000497069.1:p.Val525Ile | 3.98E-05 | 25 |
| 15 | 98911441 | ['C', 'T'] | 5 | 1.00 | ['missense_variant', | MODERATE | IGF1R | ENST00000650285.1:c.1589C>T | ENSP00000497069.1:p.Ala530Val | 1.19E-05 | 34 |
| 15 | 98913124 | ['C', 'G'] | 1 | 1.00 | ['missense_variant'] | MODERATE | IGF1R | ENST00000650285.1:c.1670C>G | ENSP00000497069.1:p.Pro557Arg | | 19 |
| 15 | 98913124 | ['C', 'T'] | 1 | 1.00 | ['missense_variant'] | MODERATE | IGF1R | ENST00000650285.1:c.1670C>T | ENSP00000497069.1:p.Pro557Leu | 7.95E-06 | 24 |
| 15 | 98913138 | ['G', 'A'] | 1 | 1.00 | ['missense_variant'] | MODERATE | IGF1R | ENST00000650285.1:c.1684G>A | ENSP00000497069.1:p.Val562Met | 1.59E-05 | 9 |
| 15 | 98913138 | ['G', 'T'] | 1 | 1.00 | ['missense_variant'] | MODERATE | IGF1R | ENST00000650285.1:c.1684G>T | ENSP00000497069.1:p.Val562Leu | 3.98E-06 | 7 |
| 15 | 98913147 | ['G', 'A'] | 2 | 1.00 | ['missense_variant'] | MODERATE | IGF1R | ENST00000650285.1:c.1693G>A | ENSP00000497069.1:p.Gly565Ser | 2.78E-05 | 22 |
| 15 | 98913160 | ['A', 'G'] | 1 | 1.00 | ['missense_variant'] | MODERATE | IGF1R | ENST00000650285.1:c.1706A>G | ENSP00000497069.1:p.His569Arg | 1.19E-05 | 19 |
| 15 | 98913189 | ['G', 'A'] | 1 | 1.00 | ['missense_variant'] | MODERATE | IGF1R | ENST00000650285.1:c.1735G>A | ENSP00000497069.1:p.Val579Ile | 6.76E-05 | 16 |
| 15 | 98913204 | ['G', 'A'] | 4 | 1.00 | ['missense_variant'] | MODERATE | IGF1R | ENST00000650285.1:c.1750G>A | ENSP00000497069.1:p.Val584Met | 1.99E-05 | 24 |
| 15 | 98913216 | ['A', 'G'] | 6 | 1.00 | ['missense_variant'] | MODERATE | IGF1R | ENST00000650285.1:c.1762A>G | ENSP00000497069.1:p.Met588Val | | 21 |
| 15 | 98913228 | ['G', 'A'] | 1 | 1.00 | ['missense_variant'] | MODERATE | IGF1R | ENST00000650285.1:c.1774G>A | ENSP00000497069.1:p.Asp592Asn | 2.39E-05 | 22 |
| 15 | 98913237 | ['C', 'G'] | 1 | 1.00 | ['missense_variant'] | MODERATE | IGF1R | ENST00000650285.1:c.1783C>G | ENSP00000497069.1:p.Arg595Gly | | 23 |
| 15 | 98913264 | ['A', 'T'] | 1 | 1.00 | ['missense_variant'] | MODERATE | IGF1R | ENST00000650285.1:c.1810A>T | ENSP00000497069.1:p.Ile604Phe | | 22 |
| 15 | 98913277 | ['C', 'CT'] | 1 | 1.00 | ['frameshift_variant' | HIGH | IGF1R | ENST00000650285.1:c.1825dup | ENSP00000497069.1:p.Ser609PhefsTer73 | | |
| 15 | 98915984 | ['G', 'A'] | 1 | 1.00 | ['missense_variant'] | MODERATE | IGF1R | ENST00000650285.1:c.1849G>A | ENSP00000497069.1:p.Val617Ile | 2.78E-05 | 17 |
| 15 | 98916017 | ['A', 'C'] | 1 | 1.00 | ['missense_variant'] | MODERATE | IGF1R | ENST00000650285.1:c.1882A>C | ENSP00000497069.1:p.Ile628Leu | | 19 |
| 15 | 98916048 | ['A', 'G'] | 1 | 1.00 | ['missense_variant'] | MODERATE | IGF1R | ENST00000650285.1:c.1913A>G | ENSP00000497069.1:p.Asn638Ser | 1.19E-05 | 26 |
| 15 | 98916090 | ['C', 'G'] | 1 | 1.00 | ['missense_variant'] | MODERATE | IGF1R | ENST00000650285.1:c.1955C>G | ENSP00000497069.1:p.Pro652Arg | | 22 |
| 15 | 98916098 | ['G', 'A'] | 1 | 1.00 | ['missense_variant'] | MODERATE | IGF1R | ENST00000650285.1:c.1963G>A | ENSP00000497069.1:p.Gly655Ser | 8.35E-05 | 15 |
| 15 | 98916111 | ['G', 'A'] | 3 | 1.00 | ['missense_variant'] | MODERATE | IGF1R | ENST00000650285.1:c.1976G>A | ENSP00000497069.1:p.Arg659Gln | 0.00066 | 19 |
| 15 | 98916126 | ['C', 'T'] | 5 | 1.00 | ['missense_variant'] | MODERATE | IGF1R | ENST00000650285.1:c.1991C>T | ENSP00000497069.1:p.Ser664Phe | 1.19E-05 | 23 |
| 15 | 98916701 | ['G', 'A'] | 2 | 1.00 | ['missense_variant'] | MODERATE | IGF1R | ENST00000650285.1:c.2026G>A | ENSP00000497069.1:p.Gly676Ser | 1.59E-05 | 22 |
| 15 | 98916708 | ['T', 'C'] | 1 | 1.00 | ['missense_variant'] | MODERATE | IGF1R | ENST00000650285.1:c.2033T>C | ENSP00000497069.1:p.Ile678Thr | | 19 |
| 15 | 98916755 | ['G', 'T'] | 1 | 1.00 | ['missense_variant'] | MODERATE | IGF1R | ENST00000650285.1:c.2080G>T | ENSP00000497069.1:p.Gly694Trp | 3.98E-06 | 24 |
| 15 | 98916797 | ['G', 'A'] | 1 | 1.00 | ['missense_variant'] | MODERATE | IGF1R | ENST00000650285.1:c.2122G>A | ENSP00000497069.1:p.Glu708Lys | 3.98E-06 | 23 |
| 15 | 98916797 | ['G', 'C'] | 1 | 1.00 | ['missense_variant'] | MODERATE | IGF1R | ENST00000650285.1:c.2122G>C | ENSP00000497069.1:p.Glu708Gln | 3.98E-06 | 22 |
| 15 | 98916799 | ['G', 'C'] | 1 | 1.00 | ['missense_variant'] | MODERATE | IGF1R | ENST00000650285.1:c.2124G>C | ENSP00000497069.1:p.Glu708Asp | 3.98E-06 | 21 |
| 15 | 98916805 | ['G', 'C'] | 1 | 1.00 | ['missense_variant'] | MODERATE | IGF1R | ENST00000650285.1:c.2130G>C | ENSP00000497069.1:p.Gln710His | 3.98E-06 | 21 |
| 15 | 98916845 | ['A', 'G'] | 1 | 1.00 | ['missense_variant'] | MODERATE | IGF1R | ENST00000650285.1:c.2170A>G | ENSP00000497069.1:p.Asn724Asp | | 24 |
| 15 | 98916856 | ['C', 'G'] | 1 | 1.00 | ['missense_variant'] | MODERATE | IGF1R | ENST00000650285.1:c.2181C>G | ENSP00000497069.1:p.His727Gln | | 23 |
| 15 | 98916869 | ['G', 'A'] | 2 | 1.00 | ['missense_variant'] | MODERATE | IGF1R | ENST00000650285.1:c.2194G>A | ENSP00000497069.1:p.Val732Met | 7.97E-06 | 24 |
| 15 | 98922156 | ['G', 'T'] | 1 | 1.00 | ['missense_variant'] | MODERATE | IGF1R | ENST00000650285.1:c.2210G>T | ENSP00000497069.1:p.Arg737Met | | 29 |
| 15 | 98922204 | ['G', 'A'] | 1 | 1.00 | ['missense_variant'] | MODERATE | IGF1R | ENST00000650285.1:c.2258G>A | ENSP00000497069.1:p.Arg753Gln | 3.98E-06 | 23 |
| 15 | 98922221 | ['G', 'A'] | 2 | 1.00 | ['missense_variant'] | MODERATE | IGF1R | ENST00000650285.1:c.2275G>A | ENSP00000497069.1:p.Ala759Thr | | 8 |
| 15 | 98922286 | ['C', 'G'] | 2 | 1.00 | ['missense_variant'] | MODERATE | IGF1R | ENST00000650285.1:c.2340C>G | ENSP00000497069.1:p.Ser780Arg | | 20 |
| 15 | 98922326 | ['C', 'T'] | 1 | 1.00 | ['missense_variant'] | MODERATE | IGF1R | ENST00000650285.1:c.2380C>T | ENSP00000497069.1:p.Arg794Trp | 3.58E-05 | 28 |
| 15 | 98922345 | ['G', 'A'] | 1 | 1.00 | ['missense_variant'] | MODERATE | IGF1R | ENST00000650285.1:c.2399G>A | ENSP00000497069.1:p.Arg800His | 3.98E-06 | 30 |
| 15 | 98922381 | ['A', 'G'] | 1 | 1.00 | ['missense_variant'] | MODERATE | IGF1R | ENST00000650285.1:c.2435A>G | ENSP00000497069.1:p.Lys812Arg | | 17 |
| 15 | 98922396 | ['C', 'T'] | 6 | 1.00 | ['missense_variant'] | MODERATE | IGF1R | ENST00000650285.1:c.2450C>T | ENSP00000497069.1:p.Ala817Val | | 20 |
| 15 | 98922406 | ['C', 'G'] | 2 | 1.00 | ['missense_variant'] | MODERATE | IGF1R | ENST00000650285.1:c.2460C>G | ENSP00000497069.1:p.Phe820Leu | 4.00E-06 | 11 |
| 15 | 98922407 | ['G', 'A'] | 5 | 1.00 | ['missense_variant'] | MODERATE | IGF1R | ENST00000650285.1:c.2461G>A | ENSP00000497069.1:p.Val821Ile | 8.00E-06 | 24 |
| 15 | 98923948 | ['C', 'T'] | 4 | 1.00 | ['missense_variant'] | MODERATE | IGF1R | ENST00000650285.1:c.2558C>T | ENSP00000497069.1:p.Pro853Leu | 0.000167 | 19 |
| 15 | 98923997 | ['C', 'G'] | 1 | 1.00 | ['stop_gained'] | HIGH | IGF1R | ENST00000650285.1:c.2607C>G | ENSP00000497069.1:p.Tyr869Ter | | 35 |
| 15 | 98924534 | ['G', 'A'] | 4 | 1.00 | ['missense_variant'] | MODERATE | IGF1R | ENST00000650285.1:c.2632G>A | ENSP00000497069.1:p.Glu878Lys | 1.59E-05 | 23 |
| 15 | 98924551 | ['G', 'T'] | 1 | 1.00 | ['missense_variant'] | MODERATE | IGF1R | ENST00000650285.1:c.2649G>T | ENSP00000497069.1:p.Gln883His | 3.98E-06 | 22 |
| 15 | 98924558 | ['A', 'G'] | 1 | 1.00 | ['missense_variant'] | MODERATE | IGF1R | ENST00000650285.1:c.2656A>G | ENSP00000497069.1:p.Arg886Gly | 3.98E-06 | 21 |
| 15 | 98924595 | ['C', 'A'] | 5 | 1.00 | ['missense_variant'] | MODERATE | IGF1R | ENST00000650285.1:c.2693C>A | ENSP00000497069.1:p.Pro898Gln | 1.19E-05 | 26 |
| 15 | 98924625 | ['C', 'T'] | 1 | 1.00 | ['missense_variant'] | MODERATE | IGF1R | ENST00000650285.1:c.2723C>T | ENSP00000497069.1:p.Thr908Ile | | 23 |
| 15 | 98929558 | ['C', 'G'] | 1 | 1.00 | ['missense_variant', | MODERATE | IGF1R | ENST00000650285.1:c.2783C>G | ENSP00000497069.1:p.Thr928Arg | | 14 |
| 15 | 98929590 | ['G', 'A'] | 2 | 1.00 | ['missense_variant'] | MODERATE | IGF1R | ENST00000650285.1:c.2815G>A | ENSP00000497069.1:p.Ala939Thr | | 17 |
| 15 | 98929602 | ['G', 'A'] | 2 | 1.00 | ['missense_variant'] | MODERATE | IGF1R | ENST00000650285.1:c.2827G>A | ENSP00000497069.1:p.Ala943Thr | 1.59E-05 | 18 |
| 15 | 98929617 | ['G', 'A'] | 1 | 1.00 | ['missense_variant'] | MODERATE | IGF1R | ENST00000650285.1:c.2842G>A | ENSP00000497069.1:p.Val948Met | 1.19E-05 | 23 |
| 15 | 98929644 | ['G', 'A'] | 1 | 1.00 | ['missense_variant'] | MODERATE | IGF1R | ENST00000650285.1:c.2869G>A | ENSP00000497069.1:p.Val957Ile | | 19 |
| 15 | 98929648 | ['T', 'C'] | 1 | 1.00 | ['missense_variant'] | MODERATE | IGF1R | ENST00000650285.1:c.2873T>C | ENSP00000497069.1:p.Phe958Ser | | 24 |
| 15 | 98930252 | ['G', 'C'] | 1 | 1.00 | ['missense_variant'] | MODERATE | IGF1R | ENST00000650285.1:c.2903G>C | ENSP00000497069.1:p.Gly968Ala | | 24 |
| 15 | 98930266 | ['T', 'C'] | 1 | 1.00 | ['missense_variant'] | MODERATE | IGF1R | ENST00000650285.1:c.2917T>C | ENSP00000497069.1:p.Tyr973His | | 32 |
| 15 | 98930299 | ['G', 'A'] | 1 | 1.00 | ['missense_variant'] | MODERATE | IGF1R | ENST00000650285.1:c.2950G>A | ENSP00000497069.1:p.Ala984Thr | 4.03E-06 | 23 |
| 15 | 98934863 | ['T', 'C'] | 1 | 1.00 | ['missense_variant'] | MODERATE | IGF1R | ENST00000650285.1:c.2996T>C | ENSP00000497069.1:p.Ile999Thr | | 30 |
| 15 | 98934875 | ['G', 'A'] | 1 | 1.00 | ['missense_variant'] | MODERATE | IGF1R | ENST00000650285.1:c.3008G>A | ENSP00000497069.1:p.Arg1003Gln | 3.18E-05 | 31 |

Figure 7 cont'd

Genetic variants found in the 5 Core genes

| chr | position | alleles | AC | variant_q | vep.consequence | vep.impact | vep.symbol | vep.hgvsc | vep.hgvsp | vep.gnoma | vep.cadd_phred |
|---|---|---|---|---|---|---|---|---|---|---|---|
| 15 | 98934880 | ['C', 'A'] | 1 | 1.00 | ['missense_variant'] | MODERATE | IGF1R | ENST00000650285.1:c.3013C>A | ENSP00000497069.1:p.Leu1005Ile | | 25 |
| 15 | 98934908 | ['A', 'G'] | 1 | 1.00 | ['missense_variant'] | MODERATE | IGF1R | ENST00000650285.1:c.3041A>G | ENSP00000497069.1:p.Tyr1014Cys | 1.19E-05 | 32 |
| 15 | 98934982 | ['G', 'T'] | 2 | 1.00 | ['missense_variant'] | MODERATE | IGF1R | ENST00000650285.1:c.3115G>T | ENSP00000497069.1:p.Ala1039Ser | 7.96E-06 | 29 |
| 15 | 98934983 | ['C', 'T'] | 2 | 1.00 | ['missense_variant'] | MODERATE | IGF1R | ENST00000650285.1:c.3116C>T | ENSP00000497069.1:p.Ala1039Val | | 27 |
| 15 | 98934988 | ['A', 'G'] | 1 | 1.00 | ['missense_variant'] | MODERATE | IGF1R | ENST00000650285.1:c.3121A>G | ENSP00000497069.1:p.Met1041Val | 3.98E-06 | 22 |
| 15 | 98935328 | ['G', 'T'] | 1 | 1.00 | ['missense_variant'] | MODERATE | IGF1R | ENST00000650285.1:c.3199G>T | ENSP00000497069.1:p.Gly1067Cys | | 34 |
| 15 | 98935380 | ['G', 'A'] | 1 | 1.00 | ['missense_variant'] | MODERATE | IGF1R | ENST00000650285.1:c.3251G>A | ENSP00000497069.1:p.Arg1084Gln | 6.39E-06 | 27 |
| 15 | 98935392 | ['A', 'T'] | 1 | 1.00 | ['missense_variant'] | MODERATE | IGF1R | ENST00000650285.1:c.3263A>T | ENSP00000497069.1:p.Lys1088Ile | | 33 |
| 15 | 98935403 | ['C', 'T'] | 1 | 1.00 | ['missense_variant'] | MODERATE | IGF1R | ENST00000650285.1:c.3274C>T | ENSP00000497069.1:p.Arg1092Trp | 6.39E-06 | 24 |
| 15 | 98935404 | ['G', 'A'] | 5 | 1.00 | ['missense_variant'] | MODERATE | IGF1R | ENST00000650285.1:c.3275G>A | ENSP00000497069.1:p.Arg1092Gln | | 34 |
| 15 | 98935422 | ['T', 'C'] | 1 | 1.00 | ['missense_variant'] | MODERATE | IGF1R | ENST00000650285.1:c.3293T>C | ENSP00000497069.1:p.Met1098Thr | | 21 |
| 15 | 98939223 | ['C', 'T'] | 1 | 1.00 | ['missense_variant'] | MODERATE | IGF1R | ENST00000650285.1:c.3320C>T | ENSP00000497069.1:p.Pro1107Leu | | 28 |
| 15 | 98939233 | ['C', 'G'] | 2 | 1.00 | ['missense_variant'] | MODERATE | IGF1R | ENST00000650285.1:c.3330C>G | ENSP00000497069.1:p.Ser1110Arg | 7.95E-06 | 22 |
| 15 | 98939238 | ['T', 'G'] | 2 | 1.00 | ['missense_variant'] | MODERATE | IGF1R | ENST00000650285.1:c.3335T>G | ENSP00000497069.1:p.Met1112Arg | | 31 |
| 15 | 98942935 | ['C', 'T'] | 1 | 1.00 | ['missense_variant'] | MODERATE | IGF1R | ENST00000650285.1:c.3470C>T | ENSP00000497069.1:p.Thr1157Met | 3.98E-06 | 27 |
| 15 | 98942947 | ['A', 'G'] | 1 | 1.00 | ['missense_variant'] | MODERATE | IGF1R | ENST00000650285.1:c.3482A>G | ENSP00000497069.1:p.Tyr1161Cys | 2.39E-05 | 33 |
| 15 | 98942959 | ['A', 'G'] | 1 | 1.00 | ['missense_variant'] | MODERATE | IGF1R | ENST00000650285.1:c.3494A>G | ENSP00000497069.1:p.Tyr1165Cys | | 33 |
| 15 | 98942964 | ['C', 'T'] | 1 | 1.00 | ['missense_variant'] | MODERATE | IGF1R | ENST00000650285.1:c.3499C>T | ENSP00000497069.1:p.Arg1167Trp | | 32 |
| 15 | 98942970 | ['G', 'A'] | 1 | 1.00 | ['missense_variant'] | MODERATE | IGF1R | ENST00000650285.1:c.3505G>A | ENSP00000497069.1:p.Gly1169Arg | | 34 |
| 15 | 98948627 | ['A', 'T'] | 1 | 1.00 | ['missense_variant'] | MODERATE | IGF1R | ENST00000650285.1:c.3641A>T | ENSP00000497069.1:p.Gln1214Leu | | 32 |
| 15 | 98948645 | ['A', 'G'] | 1 | 1.00 | ['missense_variant'] | MODERATE | IGF1R | ENST00000650285.1:c.3659A>G | ENSP00000497069.1:p.Gln1220Arg | | 30 |
| 15 | 98948653 | ['C', 'T'] | 1 | 1.00 | ['missense_variant'] | MODERATE | IGF1R | ENST00000650285.1:c.3667C>T | ENSP00000497069.1:p.Arg1223Cys | | 33 |
| 15 | 98948691 | ['C', 'A'] | 2 | 1.00 | ['missense_variant'] | MODERATE | IGF1R | ENST00000650285.1:c.3705C>A | ENSP00000497069.1:p.Asp1235Glu | | 19 |
| 15 | 98957063 | ['T', 'A'] | 1 | 1.00 | ['missense_variant', | MODERATE | IGF1R | ENST00000650285.1:c.3725T>A | ENSP00000497069.1:p.Phe1242Tyr | | 20 |
| 15 | 98957093 | ['A', 'G'] | 1 | 1.00 | ['missense_variant'] | MODERATE | IGF1R | ENST00000650285.1:c.3755A>G | ENSP00000497069.1:p.Asn1252Ser | 3.98E-06 | 24 |
| 15 | 98957146 | ['A', 'G'] | 1 | 1.00 | ['missense_variant'] | MODERATE | IGF1R | ENST00000650285.1:c.3808A>G | ENSP00000497069.1:p.Met1270Val | | 19 |
| 15 | 98957183 | ['G', 'A'] | 1 | 1.00 | ['missense_variant'] | MODERATE | IGF1R | ENST00000650285.1:c.3845G>A | ENSP00000497069.1:p.Ser1282Asn | 7.95E-06 | 30 |
| 15 | 98957184 | ['CGAG', '( | 1 | 1.00 | ['inframe_deletion'] | MODERATE | IGF1R | ENST00000650285.1:c.3850_3852del | ENSP00000497069.1:p.Glu1284del | 1.99E-05 | |
| 15 | 98957185 | ['G', 'A'] | 2 | 1.00 | ['missense_variant'] | MODERATE | IGF1R | ENST00000650285.1:c.3847G>A | ENSP00000497069.1:p.Glu1283Lys | 0.000103 | 25 |
| 15 | 98957206 | ['C', 'T'] | 1 | 1.00 | ['missense_variant'] | MODERATE | IGF1R | ENST00000650285.1:c.3868C>T | ENSP00000497069.1:p.Pro1290Ser | | 9 |
| 15 | 98957207 | ['C', 'T'] | 2 | 1.00 | ['missense_variant'] | MODERATE | IGF1R | ENST00000650285.1:c.3869C>T | ENSP00000497069.1:p.Pro1290Leu | 3.58E-05 | 17 |
| 15 | 98957214 | ['G', 'GCT( | 1 | 1.00 | ['inframe_insertion'] | MODERATE | IGF1R | ENST00000650285.1:c.3882_3887dup | ENSP00000497069.1:p.Asp1294_Leu1295dup | 3.98E-06 | |
| 15 | 98957221 | ['C', 'G'] | 1 | 1.00 | ['missense_variant'] | MODERATE | IGF1R | ENST00000650285.1:c.3883C>G | ENSP00000497069.1:p.Leu1295Val | | 20 |
| 15 | 98957239 | ['G', 'A'] | 1 | 1.00 | ['missense_variant'] | MODERATE | IGF1R | ENST00000650285.1:c.3901G>A | ENSP00000497069.1:p.Glu1301Lys | | 32 |
| 15 | 98957270 | ['C', 'T'] | 5 | 1.00 | ['missense_variant'] | MODERATE | IGF1R | ENST00000650285.1:c.3932C>T | ENSP00000497069.1:p.Ser1311Leu | 8.00E-05 | 22 |
| 15 | 98957273 | ['C', 'T'] | 1 | 1.00 | ['missense_variant'] | MODERATE | IGF1R | ENST00000650285.1:c.3935C>T | ENSP00000497069.1:p.Ser1312Phe | | 23 |
| 15 | 98957290 | ['G', 'C'] | 1 | 1.00 | ['missense_variant'] | MODERATE | IGF1R | ENST00000650285.1:c.3952G>C | ENSP00000497069.1:p.Asp1318His | | 24 |
| 15 | 98957290 | ['G', 'T'] | 1 | 1.00 | ['missense_variant'] | MODERATE | IGF1R | ENST00000650285.1:c.3952G>T | ENSP00000497069.1:p.Asp1318Tyr | 1.20E-05 | 24 |
| 15 | 98957300 | ['C', 'A'] | 1 | 1.00 | ['stop_gained'] | HIGH | IGF1R | ENST00000650285.1:c.3962C>A | ENSP00000497069.1:p.Ser1321Ter | 3.99E-06 | 47 |
| 15 | 98957307 | ['C', 'G'] | 1 | 1.00 | ['missense_variant'] | MODERATE | IGF1R | ENST00000650285.1:c.3969C>G | ENSP00000497069.1:p.His1323Gln | | 16 |
| 15 | 98957317 | ['A', 'G'] | 1 | 1.00 | ['missense_variant'] | MODERATE | IGF1R | ENST00000650285.1:c.3979A>G | ENSP00000497069.1:p.Asn1327Asp | 3.60E-05 | 21 |
| 15 | 98957326 | ['G', 'A'] | 5 | 1.00 | ['missense_variant'] | MODERATE | IGF1R | ENST00000650285.1:c.3988G>A | ENSP00000497069.1:p.Gly1330Ser | 5.20E-05 | 14 |
| 15 | 98957341 | ['G', 'T'] | 1 | 1.00 | ['missense_variant'] | MODERATE | IGF1R | ENST00000650285.1:c.4003G>T | ENSP00000497069.1:p.Val1335Phe | | 23 |
| 15 | 98957348 | ['G', 'A'] | 1 | 1.00 | ['missense_variant'] | MODERATE | IGF1R | ENST00000650285.1:c.4010G>A | ENSP00000497069.1:p.Arg1337His | 2.00E-05 | 26 |
| 15 | 98957362 | ['G', 'A'] | 2 | 1.00 | ['missense_variant'] | MODERATE | IGF1R | ENST00000650285.1:c.4024G>A | ENSP00000497069.1:p.Glu1342Lys | 4.00E-06 | 25 |
| 15 | 98957366 | ['G', 'T'] | 5 | 1.00 | ['missense_variant'] | MODERATE | IGF1R | ENST00000650285.1:c.4028G>T | ENSP00000497069.1:p.Arg1343Ile | 2.00E-05 | 23 |
| 15 | 98957383 | ['A', 'G'] | 2 | 1.00 | ['missense_variant'] | MODERATE | IGF1R | ENST00000650285.1:c.4045A>G | ENSP00000497069.1:p.Met1349Val | 8.02E-06 | 26 |
| 15 | 98957393 | ['G', 'C'] | 2 | 1.00 | ['missense_variant'] | MODERATE | IGF1R | ENST00000650285.1:c.4055G>C | ENSP00000497069.1:p.Gly1352Ala | | 28 |
| 15 | 98957395 | ['C', 'T'] | 2 | 1.00 | ['missense_variant'] | MODERATE | IGF1R | ENST00000650285.1:c.4057C>T | ENSP00000497069.1:p.Arg1353Cys | 8.04E-06 | 28 |
| 15 | 98957404 | ['G', 'A'] | 3 | 1.00 | ['missense_variant'] | MODERATE | IGF1R | ENST00000650285.1:c.4066G>A | ENSP00000497069.1:p.Glu1356Lys | 4.83E-05 | 25 |
| 15 | 98957404 | ['G', 'C'] | 1 | 1.00 | ['missense_variant'] | MODERATE | IGF1R | ENST00000650285.1:c.4066G>C | ENSP00000497069.1:p.Glu1356Gln | | 25 |
| 15 | 98957407 | ['C', 'T'] | 2 | 1.00 | ['missense_variant'] | MODERATE | IGF1R | ENST00000650285.1:c.4069C>T | ENSP00000497069.1:p.Arg1357Trp | 0.00025 | 25 |
| 15 | 98957408 | ['G', 'A'] | 2 | 1.00 | ['missense_variant'] | MODERATE | IGF1R | ENST00000650285.1:c.4070G>A | ENSP00000497069.1:p.Arg1357Gln | 3.22E-05 | 32 |
| 15 | 98957425 | ['C', 'T'] | 1 | 1.00 | ['stop_gained'] | HIGH | IGF1R | ENST00000650285.1:c.4087C>T | ENSP00000497069.1:p.Gln1363Ter | 8.07E-06 | 52 |
| 15 | 98957432 | ['C', 'T'] | 1 | 1.00 | ['missense_variant'] | MODERATE | IGF1R | ENST00000650285.1:c.4094C>T | ENSP00000497069.1:p.Ser1365Leu | 8.08E-06 | 26 |
| X | 630910 | ['A', 'G'] | 1 | 1.00 | ['missense_variant'] | MODERATE | SHOX | ENST00000381578.6:c.13A>G | ENSP00000370990.1:p.Thr5Ala | 7.99E-06 | 25 |
| X | 630922 | ['T', 'C'] | 1 | 1.00 | ['missense_variant'] | MODERATE | SHOX | ENST00000381578.6:c.25T>C | ENSP00000370990.1:p.Ser9Pro | | 25 |
| X | 630950 | ['A', 'T'] | 1 | 1.00 | ['missense_variant'] | MODERATE | SHOX | ENST00000381578.6:c.53A>T | ENSP00000370990.1:p.Asp18Val | 3.99E-06 | 22 |
| X | 630981 | ['TAAG', 'T | 3 | 1.00 | ['inframe_deletion'] | MODERATE | SHOX | ENST00000381578.6:c.88_90del | ENSP00000370990.1:p.Lys30del | | |
| X | 631004 | ['G', 'A'] | 1 | 1.00 | ['missense_variant'] | MODERATE | SHOX | ENST00000381578.6:c.107G>A | ENSP00000370990.1:p.Arg36Gln | | 26 |
| X | 631028 | ['C', 'A'] | 5 | 1.00 | ['missense_variant'] | MODERATE | SHOX | ENST00000381578.6:c.131C>A | ENSP00000370990.1:p.Ala44Glu | | 23 |
| X | 631045 | ['G', 'A'] | 1 | 1.00 | ['missense_variant'] | MODERATE | SHOX | ENST00000381578.6:c.148G>A | ENSP00000370990.1:p.Gly50Arg | | 22 |

Figure 7 cont'd

Genetic variants found in the 5 Core genes

| chr | position | alleles | AC | variant_q | vep.consequence | vep.impact | vep.symbol | vep.hgvsc | vep.hgvsp | vep.gnom: | vep.cadd_phred |
|---|---|---|---|---|---|---|---|---|---|---|---|
| X | 631074 | ['C', 'G'] | 1 | 1.00 | ['missense_variant'] | MODERATE | SHOX | ENST00000381578.6:c.177C>G | ENSP00000370990.1:p.Ile59Met | | 0 |
| X | 631087 | ['G', 'C'] | 5 | 1.00 | ['missense_variant'] | MODERATE | SHOX | ENST00000381578.6:c.190G>C | ENSP00000370990.1:p.Gly64Arg | | 20 |
| X | 631097 | ['C', 'T'] | 1 | 1.00 | ['missense_variant'] | MODERATE | SHOX | ENST00000381578.6:c.200C>T | ENSP00000370990.1:p.Pro67Leu | | 23 |
| X | 631108 | ['T', 'C'] | 4 | 1.00 | ['missense_variant'] | MODERATE | SHOX | ENST00000381578.6:c.211T>C | ENSP00000370990.1:p.Phe71Leu | | 21 |
| X | 631115 | ['A', 'G'] | 1 | 1.00 | ['missense_variant'] | MODERATE | SHOX | ENST00000381578.6:c.218A>G | ENSP00000370990.1:p.Asp73Gly | | 20 |
| X | 631163 | ['G', 'C'] | 1 | 1.00 | ['missense_variant'] | MODERATE | SHOX | ENST00000381578.6:c.266G>C | ENSP00000370990.1:p.Arg89Thr | | 22 |
| X | 631169 | ['C', 'T'] | 1 | 1.00 | ['missense_variant'] | MODERATE | SHOX | ENST00000381578.6:c.272C>T | ENSP00000370990.1:p.Ala91Val | | 10 |
| X | 634631 | ['C', 'G'] | 1 | 1.00 | ['missense_variant'] | MODERATE | SHOX | ENST00000381578.6:c.291C>G | ENSP00000370990.1:p.Cys97Trp | | 24 |
| X | 634635 | ['G', 'A'] | 1 | 1.00 | ['missense_variant'] | MODERATE | SHOX | ENST00000381578.6:c.295G>A | ENSP00000370990.1:p.Glu99Lys | | 23 |
| X | 634637 | ['G', 'C'] | 1 | 1.00 | ['missense_variant'] | MODERATE | SHOX | ENST00000381578.6:c.297G>C | ENSP00000370990.1:p.Glu99Asp | | 7 |
| X | 634668 | ['G', 'T'] | 1 | 1.00 | ['missense_variant'] | MODERATE | SHOX | ENST00000381578.6:c.328G>T | ENSP00000370990.1:p.Asp110Tyr | | 26 |
| X | 634671 | ['G', 'C'] | 5 | 1.00 | ['missense_variant'] | MODERATE | SHOX | ENST00000381578.6:c.331G>C | ENSP00000370990.1:p.Gly111Arg | | 22 |
| X | 634676 | ['G', 'C'] | 1 | 1.00 | ['missense_variant'] | MODERATE | SHOX | ENST00000381578.6:c.336G>C | ENSP00000370990.1:p.Gln112His | | 24 |
| X | 634689 | ['CAG', 'C'] | 1 | 1.00 | ['frameshift_variant' | HIGH | SHOX | ENST00000381578.6:c.352_353del | ENSP00000370990.1:p.Arg118AlafsTer63 | | |
| X | 634696 | ['G', 'A'] | 1 | 1.00 | ['missense_variant'] | MODERATE | SHOX | ENST00000381578.6:c.356G>A | ENSP00000370990.1:p.Arg119His | | 24 |
| X | 634705 | ['C', 'G'] | 1 | 1.00 | ['missense_variant'] | MODERATE | SHOX | ENST00000381578.6:c.365C>G | ENSP00000370990.1:p.Thr122Ser | 4.01E-06 | 24 |
| X | 634719 | ['G', 'C'] | 1 | 1.00 | ['missense_variant'] | MODERATE | SHOX | ENST00000381578.6:c.379G>C | ENSP00000370990.1:p.Glu127Gln | | 25 |
| X | 634741 | ['G', 'A'] | 1 | 1.00 | ['missense_variant'] | MODERATE | SHOX | ENST00000381578.6:c.401G>A | ENSP00000370990.1:p.Arg134Gln | | 25 |
| X | 634743 | ['C', 'T'] | 1 | 1.00 | ['missense_variant'] | MODERATE | SHOX | ENST00000381578.6:c.403C>T | ENSP00000370990.1:p.Leu135Phe | | 23 |
| X | 634771 | ['C', 'G'] | 1 | 1.00 | ['missense_variant'] | MODERATE | SHOX | ENST00000381578.6:c.431C>G | ENSP00000370990.1:p.Ala144Gly | | 24 |
| X | 634776 | ['A', 'C'] | 1 | 1.00 | ['missense_variant'] | MODERATE | SHOX | ENST00000381578.6:c.436A>C | ENSP00000370990.1:p.Met146Leu | | 24 |
| X | 634782 | ['G', 'A'] | 1 | 1.00 | ['missense_variant'] | MODERATE | SHOX | ENST00000381578.6:c.442G>A | ENSP00000370990.1:p.Glu148Lys | | 25 |
| X | 640851 | ['C', 'A'] | 1 | 1.00 | ['missense_variant'] | MODERATE | SHOX | ENST00000381578.6:c.517C>A | ENSP00000370990.1:p.Arg173Ser | | 19 |
| X | 640877 | ['A', 'C'] | 4 | 1.00 | ['missense_variant', | MODERATE | SHOX | ENST00000381578.6:c.543A>C | ENSP00000370990.1:p.Lys181Asn | 3.58E-05 | 24 |
| X | 641001 | ['G', 'A'] | 4 | 1.00 | ['missense_variant', | MODERATE | SHOX | ENST00000381578.6:c.547G>A | ENSP00000370990.1:p.Val183Ile | | 17 |
| X | 641037 | ['C', 'T'] | 2 | 1.00 | ['stop_gained'] | HIGH | SHOX | ENST00000381578.6:c.583C>T | ENSP00000370990.1:p.Arg195Ter | | 35 |
| X | 641038 | ['G', 'A'] | 2 | 1.00 | ['missense_variant'] | MODERATE | SHOX | ENST00000381578.6:c.584G>A | ENSP00000370990.1:p.Arg195Gln | | 25 |
| X | 641052 | ['G', 'A'] | 3 | 1.00 | ['missense_variant'] | MODERATE | SHOX | ENST00000381578.6:c.598G>A | ENSP00000370990.1:p.Val200Ile | | 22 |
| X | 641065 | ['C', 'T'] | 4 | 1.00 | ['missense_variant'] | MODERATE | SHOX | ENST00000381578.6:c.611C>T | ENSP00000370990.1:p.Ala204Val | | 23 |
| X | 641065 | ['C', 'A'] | 1 | 1.00 | ['missense_variant'] | MODERATE | SHOX | ENST00000381578.6:c.611C>A | ENSP00000370990.1:p.Ala204Asp | | 23 |
| X | 641068 | ['T', 'C'] | 1 | 1.00 | ['missense_variant'] | MODERATE | SHOX | ENST00000381578.6:c.614T>C | ENSP00000370990.1:p.Leu205Ser | | 23 |
| X | 644397 | ['G', 'A'] | 1 | 1.00 | ['missense_variant'] | MODERATE | SHOX | ENST00000381578.6:c.640G>A | ENSP00000370990.1:p.Ala214Thr | | 25 |
| X | 644418 | ['G', 'A'] | 1 | 1.00 | ['missense_variant'] | MODERATE | SHOX | ENST00000381578.6:c.661G>A | ENSP00000370990.1:p.Val221Met | | 26 |
| X | 644422 | ['C', 'T'] | 1 | 1.00 | ['missense_variant'] | MODERATE | SHOX | ENST00000381578.6:c.665C>T | ENSP00000370990.1:p.Ala222Val | | 23 |
| X | 644423 | ['C', 'CCAC | 1 | 1.00 | ['inframe_insertion'] | MODERATE | SHOX | ENST00000381578.6:c.670_681dup | ENSP00000370990.1:p.Ala224_His227dup | 3.36E-05 | |
| X | 644427 | ['G', 'A'] | 1 | 1.00 | ['missense_variant'] | MODERATE | SHOX | ENST00000381578.6:c.670G>A | ENSP00000370990.1:p.Ala224Thr | | 22 |
| X | 644428 | ['CGCACCC | 3 | 1.00 | ['inframe_deletion'] | MODERATE | SHOX | ENST00000381578.6:c.685_696del | ENSP00000370990.1:p.His229_Leu232del | | |
| X | 644434 | ['C', 'CGCA | 1 | 1.00 | ['inframe_insertion'] | MODERATE | SHOX | ENST00000381578.6:c.683_688dup | ENSP00000370990.1:p.Leu228_His229dup | | |
| X | 644464 | ['C', 'T'] | 1 | 1.00 | ['missense_variant'] | MODERATE | SHOX | ENST00000381578.6:c.707C>T | ENSP00000370990.1:p.Ala236Val | | 25 |
| X | 644484 | ['C', 'G'] | 1 | 1.00 | ['missense_variant'] | MODERATE | SHOX | ENST00000381578.6:c.727C>G | ENSP00000370990.1:p.Pro243Ala | | 21 |
| X | 644524 | ['CCGCCTC | 1 | 1.00 | ['inframe_deletion'] | MODERATE | SHOX | ENST00000381578.6:c.772_792del | ENSP00000370990.1:p.Ser258_Ala264del | | |
| X | 644539 | ['C', 'G'] | 1 | 1.00 | ['missense_variant'] | MODERATE | SHOX | ENST00000381578.6:c.782C>G | ENSP00000370990.1:p.Ala261Gly | | 19 |
| X | 644563 | ['G', 'T'] | 1 | 1.00 | ['missense_variant'] | MODERATE | SHOX | ENST00000381578.6:c.806G>T | ENSP00000370990.1:p.Ser269Ile | | 24 |
| X | 644578 | ['C', 'T'] | 1 | 1.00 | ['missense_variant'] | MODERATE | SHOX | ENST00000381578.6:c.821C>T | ENSP00000370990.1:p.Ser274Phe | | 26 |
| X | 644586 | ['G', 'A'] | 5 | 1.00 | ['missense_variant'] | MODERATE | SHOX | ENST00000381578.6:c.829G>A | ENSP00000370990.1:p.Ala277Thr | | 27 |
| X | 644598 | ['C', 'T'] | 1 | 1.00 | ['missense_variant'] | MODERATE | SHOX | ENST00000381578.6:c.841C>T | ENSP00000370990.1:p.Leu281Phe | | 25 |
| X | 644604 | ['G', 'C'] | 1 | 1.00 | ['missense_variant'] | MODERATE | SHOX | ENST00000381578.6:c.847G>C | ENSP00000370990.1:p.Ala283Pro | | 26 |
| X | 644608 | ['G', 'A'] | 2 | 1.00 | ['missense_variant'] | MODERATE | SHOX | ENST00000381578.6:c.851G>A | ENSP00000370990.1:p.Arg284Gln | | 25 |
| X | 644622 | ['G', 'T'] | 1 | 1.00 | ['missense_variant'] | MODERATE | SHOX | ENST00000381578.6:c.865G>T | ENSP00000370990.1:p.Ala289Ser | | 24 |
| X | 644622 | ['G', 'T'] | 1 | 1.00 | ['missense_variant'] | MODERATE | SHOX | ENST00000381578.6:c.865G>T | ENSP00000370990.1:p.Ala289Ser | | 24 |

SEQUENCE LISTING

```
<160> NUMBER OF SEQ ID NOS: 68

<210> SEQ ID NO 1
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 1

Pro Gly Gln Glu His Pro Asn Ala Arg Lys Tyr Lys Gly Ala Asn Lys
1               5                   10                  15
```

Lys Gly Leu Ser Lys Gly Cys Phe Gly Leu Lys Leu Asp Arg Ile Gly
20 25 30

Ser Met Ser Gly Leu Gly Cys
35

<210> SEQ ID NO 2
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 2

Leu Gln Glu His Pro Asn Ala Arg Lys Tyr Lys Gly Ala Asn Lys Lys
1 5 10 15

Gly Leu Ser Lys Gly Cys Phe Gly Leu Lys Leu Asp Arg Ile Gly Ser
20 25 30

Met Ser Gly Leu Gly Cys
35

<210> SEQ ID NO 3
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 3

Gln Glu His Pro Asn Ala Arg Lys Tyr Lys Gly Ala Asn Lys Lys Gly
1 5 10 15

Leu Ser Lys Gly Cys Phe Gly Leu Lys Leu Asp Arg Ile Gly Ser Met
20 25 30

Ser Gly Leu Gly Cys
35

<210> SEQ ID NO 4
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 4

Pro Asn Ala Arg Lys Tyr Lys Gly Ala Asn Lys Lys Gly Leu Ser Lys
1 5 10 15

Gly Cys Phe Gly Leu Lys Leu Asp Arg Ile Gly Ser Met Ser Gly Leu
20 25 30

Gly Cys

<210> SEQ ID NO 5
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 5

Pro Gly Gln Glu His Pro Gln Ala Arg Arg Tyr Arg Gly Ala Gln Arg
1 5 10 15

Arg Gly Leu Ser Arg Gly Cys Phe Gly Leu Lys Leu Asp Arg Ile Gly
20 25 30

```
Ser Met Ser Gly Leu Gly Cys
        35


<210> SEQ ID NO 6
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 6

Pro Gly Gln Glu His Pro Asn Ala Arg Arg Tyr Arg Gly Ala Asn Arg
1               5                   10                  15

Arg Gly Leu Ser Arg Gly Cys Phe Gly Leu Lys Leu Asp Arg Ile Gly
            20                  25                  30

Ser Met Ser Gly Leu Gly Cys
        35


<210> SEQ ID NO 7
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 7

Pro Gly Gln Glu His Pro Gln Ala Arg Lys Tyr Lys Gly Ala Gln Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
        35


<210> SEQ ID NO 8
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N -terminal Acetyl
<220> FEATURE:
<221> NAME/KEY: MISC_FEATURE
<222> LOCATION: (39)..(39)
<223> OTHER INFORMATION: C -terminal OH

<400> SEQUENCE: 8

Pro Gly Gln Glu His Pro Gln Ala Arg Arg Tyr Arg Gly Ala Gln Arg
1               5                   10                  15

Arg Gly Leu Ser Arg Gly Cys Phe Gly Leu Lys Leu Asp Arg Ile Gly
            20                  25                  30

Ser Met Ser Gly Leu Gly Cys
        35


<210> SEQ ID NO 9
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N -terminal Acetyl
```

<220> FEATURE:
<221> NAME/KEY: MISC_FEATURE
<222> LOCATION: (39)..(39)
<223> OTHER INFORMATION: C -terminal NH2

<400> SEQUENCE: 9

```
Pro Gly Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
        35
```

<210> SEQ ID NO 10
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N -terminal Acetyl
<220> FEATURE:
<221> NAME/KEY: MISC_FEATURE
<222> LOCATION: (39)..(39)
<223> OTHER INFORMATION: C -terminal OH

<400> SEQUENCE: 10

```
Pro Gly Gln Glu His Pro Asn Ala Arg Arg Tyr Arg Gly Ala Asn Arg
1               5                   10                  15

Arg Gly Leu Ser Arg Gly Cys Phe Gly Leu Lys Leu Asp Arg Ile Gly
            20                  25                  30

Ser Met Ser Gly Leu Gly Cys
        35
```

<210> SEQ ID NO 11
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N -terminal Acetyl
<220> FEATURE:
<221> NAME/KEY: MISC_FEATURE
<222> LOCATION: (39)..(39)
<223> OTHER INFORMATION: C -terminal NH2

<400> SEQUENCE: 11

```
Pro Gly Gln Glu His Pro Asn Ala Arg Arg Tyr Arg Gly Ala Asn Arg
1               5                   10                  15

Arg Gly Leu Ser Arg Gly Cys Phe Gly Leu Lys Leu Asp Arg Ile Gly
            20                  25                  30

Ser Met Ser Gly Leu Gly Cys
        35
```

<210> SEQ ID NO 12
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N -terminal Acetyl
<220> FEATURE:
<221> NAME/KEY: MISC_FEATURE
<222> LOCATION: (39)..(39)
<223> OTHER INFORMATION: C -terminal NH2

<400> SEQUENCE: 12

```
Pro Gly Gln Glu His Pro Gln Ala Arg Arg Tyr Arg Gly Ala Gln Arg
1               5                   10                  15

Arg Gly Leu Ser Arg Gly Cys Phe Gly Leu Lys Leu Asp Arg Ile Gly
            20                  25                  30

Ser Met Ser Gly Leu Gly Cys
        35
```

<210> SEQ ID NO 13
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N -terminal Acetyl
<220> FEATURE:
<221> NAME/KEY: MISC_FEATURE
<222> LOCATION: (39)..(39)
<223> OTHER INFORMATION: C -terminal NH2

<400> SEQUENCE: 13

```
Pro Gly Gln Glu His Pro Gln Ala Arg Lys Tyr Lys Gly Ala Gln Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
        35
```

<210> SEQ ID NO 14
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N -terminal Acetyl
<220> FEATURE:
<221> NAME/KEY: MISC_FEATURE
<222> LOCATION: (39)..(39)
<223> OTHER INFORMATION: C -terminal OH

<400> SEQUENCE: 14

```
Pro Gly Gln Glu His Pro Gln Ala Arg Lys Tyr Lys Gly Ala Gln Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
        35
```

<210> SEQ ID NO 15
<211> LENGTH: 52
<212> TYPE: PRT
<213> ORGANISM: Artificial Sequence
<220> FEATURE:
<223> OTHER INFORMATION: Synthetic Polypeptide

<400> SEQUENCE: 15

Leu Arg Val Asp Thr Lys Ser Arg Ala Ala Trp Ala Arg Leu Leu Gln
1               5                   10                  15

Glu His Pro Asn Ala Arg Lys Tyr Lys Gly Ala Asn Lys Lys Gly Leu
            20                  25                  30

Ser Lys Gly Cys Phe Gly Leu Lys Leu Asp Arg Ile Gly Ser Met Ser
        35                  40                  45

Gly Leu Gly Cys
    50

<210> SEQ ID NO 16
<211> LENGTH: 51
<212> TYPE: PRT
<213> ORGANISM: Artificial Sequence
<220> FEATURE:
<223> OTHER INFORMATION: Synthetic Polypeptide

<400> SEQUENCE: 16

Arg Val Asp Thr Lys Ser Arg Ala Ala Trp Ala Arg Leu Leu Gln Glu
1               5                   10                  15

His Pro Asn Ala Arg Lys Tyr Lys Gly Ala Asn Lys Lys Gly Leu Ser
            20                  25                  30

Lys Gly Cys Phe Gly Leu Lys Leu Asp Arg Ile Gly Ser Met Ser Gly
        35                  40                  45

Leu Gly Cys
    50

<210> SEQ ID NO 17
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 17

Val Asp Thr Lys Ser Arg Ala Ala Trp Ala Arg Leu Leu Gln Glu His
1               5                   10                  15

Pro Asn Ala Arg Lys Tyr Lys Gly Ala Asn Lys Lys Gly Leu Ser Lys
            20                  25                  30

Gly Cys Phe Gly Leu Lys Leu Asp Arg Ile Gly Ser Met Ser Gly Leu
        35                  40                  45

Gly Cys
    50

<210> SEQ ID NO 18
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 18

Asp Thr Lys Ser Arg Ala Ala Trp Ala Arg Leu Leu Gln Glu His Pro
1               5                   10                  15

Asn Ala Arg Lys Tyr Lys Gly Ala Asn Lys Lys Gly Leu Ser Lys Gly
            20                  25                  30

Cys Phe Gly Leu Lys Leu Asp Arg Ile Gly Ser Met Ser Gly Leu Gly
        35                  40                  45

Cys

-continued

<210> SEQ ID NO 19
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 19

```
Thr Lys Ser Arg Ala Ala Trp Ala Arg Leu Leu Gln Glu His Pro Asn
1               5                   10                  15

Ala Arg Lys Tyr Lys Gly Ala Asn Lys Lys Gly Leu Ser Lys Gly Cys
            20                  25                  30

Phe Gly Leu Lys Leu Asp Arg Ile Gly Ser Met Ser Gly Leu Gly Cys
        35                  40                  45
```

<210> SEQ ID NO 20
<211> LENGTH: 47
<212> TYPE: PRT
<213> ORGANISM: Artificial Sequence
<220> FEATURE:
<223> OTHER INFORMATION: Synthetic Polypeptide

<400> SEQUENCE: 20

```
Lys Ser Arg Ala Ala Trp Ala Arg Leu Leu Gln Glu His Pro Asn Ala
1               5                   10                  15

Arg Lys Tyr Lys Gly Ala Asn Lys Lys Gly Leu Ser Lys Gly Cys Phe
            20                  25                  30

Gly Leu Lys Leu Asp Arg Ile Gly Ser Met Ser Gly Leu Gly Cys
        35                  40                  45
```

<210> SEQ ID NO 21
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 21

```
Ser Arg Ala Ala Trp Ala Arg Leu Leu Gln Glu His Pro Asn Ala Arg
1               5                   10                  15

Lys Tyr Lys Gly Ala Asn Lys Lys Gly Leu Ser Lys Gly Cys Phe Gly
            20                  25                  30

Leu Lys Leu Asp Arg Ile Gly Ser Met Ser Gly Leu Gly Cys
        35                  40                  45
```

<210> SEQ ID NO 22
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 22

```
Arg Ala Ala Trp Ala Arg Leu Leu Gln Glu His Pro Asn Ala Arg Lys
1               5                   10                  15

Tyr Lys Gly Ala Asn Lys Lys Gly Leu Ser Lys Gly Cys Phe Gly Leu
            20                  25                  30

Lys Leu Asp Arg Ile Gly Ser Met Ser Gly Leu Gly Cys
        35                  40                  45
```

<210> SEQ ID NO 23

<211> LENGTH: 44
<212> TYPE: PRT
<213> ORGANISM: Artificial Sequence
<220> FEATURE:
<223> OTHER INFORMATION: Synthetic Polypeptide

<400> SEQUENCE: 23

Ala Ala Trp Ala Arg Leu Leu Gln Glu His Pro Asn Ala Arg Lys Tyr
1 5 10 15

Lys Gly Ala Asn Lys Lys Gly Leu Ser Lys Gly Cys Phe Gly Leu Lys
20 25 30

Leu Asp Arg Ile Gly Ser Met Ser Gly Leu Gly Cys
35 40

<210> SEQ ID NO 24
<211> LENGTH: 43
<212> TYPE: PRT
<213> ORGANISM: Artificial Sequence
<220> FEATURE:
<223> OTHER INFORMATION: Synthetic Polypeptide

<400> SEQUENCE: 24

Ala Trp Ala Arg Leu Leu Gln Glu His Pro Asn Ala Arg Lys Tyr Lys
1 5 10 15

Gly Ala Asn Lys Lys Gly Leu Ser Lys Gly Cys Phe Gly Leu Lys Leu
20 25 30

Asp Arg Ile Gly Ser Met Ser Gly Leu Gly Cys
35 40

<210> SEQ ID NO 25
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 25

Trp Ala Arg Leu Leu Gln Glu His Pro Asn Ala Arg Lys Tyr Lys Gly
1 5 10 15

Ala Asn Lys Lys Gly Leu Ser Lys Gly Cys Phe Gly Leu Lys Leu Asp
20 25 30

Arg Ile Gly Ser Met Ser Gly Leu Gly Cys
35 40

<210> SEQ ID NO 26
<211> LENGTH: 41
<212> TYPE: PRT
<213> ORGANISM: Artificial Sequence
<220> FEATURE:
<223> OTHER INFORMATION: Synthetic Polypeptide

<400> SEQUENCE: 26

Ala Arg Leu Leu Gln Glu His Pro Asn Ala Arg Lys Tyr Lys Gly Ala
1 5 10 15

Asn Lys Lys Gly Leu Ser Lys Gly Cys Phe Gly Leu Lys Leu Asp Arg
20 25 30

Ile Gly Ser Met Ser Gly Leu Gly Cys
35 40

<210> SEQ ID NO 27
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 27

```
Arg Leu Leu Gln Glu His Pro Asn Ala Arg Lys Tyr Lys Gly Ala Asn
1               5                   10                  15

Lys Lys Gly Leu Ser Lys Gly Cys Phe Gly Leu Lys Leu Asp Arg Ile
            20                  25                  30

Gly Ser Met Ser Gly Leu Gly Cys
        35                  40
```

<210> SEQ ID NO 28
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 28

```
Leu Leu Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
        35
```

<210> SEQ ID NO 29
<211> LENGTH: 36
<212> TYPE: PRT
<213> ORGANISM: Artificial Sequence
<220> FEATURE:
<223> OTHER INFORMATION: Synthetic Polypeptide

<400> SEQUENCE: 29

```
Glu His Pro Asn Ala Arg Lys Tyr Lys Gly Ala Asn Lys Lys Gly Leu
1               5                   10                  15

Ser Lys Gly Cys Phe Gly Leu Lys Leu Asp Arg Ile Gly Ser Met Ser
            20                  25                  30

Gly Leu Gly Cys
        35
```

<210> SEQ ID NO 30
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 30

```
His Pro Asn Ala Arg Lys Tyr Lys Gly Ala Asn Lys Lys Gly Leu Ser
1               5                   10                  15

Lys Gly Cys Phe Gly Leu Lys Leu Asp Arg Ile Gly Ser Met Ser Gly
            20                  25                  30

Leu Gly Cys
        35
```

<210> SEQ ID NO 31
<211> LENGTH: 33
<212> TYPE: PRT
<213> ORGANISM: Artificial Sequence
<220> FEATURE:
<223> OTHER INFORMATION: Synthetic Polypeptide

<400> SEQUENCE: 31

Asn Ala Arg Lys Tyr Lys Gly Ala Asn Lys Lys Gly Leu Ser Lys Gly
1 5 10 15

Cys Phe Gly Leu Lys Leu Asp Arg Ile Gly Ser Met Ser Gly Leu Gly
20 25 30

Cys

<210> SEQ ID NO 32
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 32

Ala Arg Lys Tyr Lys Gly Ala Asn Lys Lys Gly Leu Ser Lys Gly Cys
1 5 10 15

Phe Gly Leu Lys Leu Asp Arg Ile Gly Ser Met Ser Gly Leu Gly Cys
20 25 30

<210> SEQ ID NO 33
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 33

Arg Lys Tyr Lys Gly Ala Asn Lys Lys Gly Leu Ser Lys Gly Cys Phe
1 5 10 15

Gly Leu Lys Leu Asp Arg Ile Gly Ser Met Ser Gly Leu Gly Cys
20 25 30

<210> SEQ ID NO 34
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 34

Lys Tyr Lys Gly Ala Asn Lys Lys Gly Leu Ser Lys Gly Cys Phe Gly
1 5 10 15

Leu Lys Leu Asp Arg Ile Gly Ser Met Ser Gly Leu Gly Cys
20 25 30

<210> SEQ ID NO 35
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 35

Tyr Lys Gly Ala Asn Lys Lys Gly Leu Ser Lys Gly Cys Phe Gly Leu
1 5 10 15

Lys Leu Asp Arg Ile Gly Ser Met Ser Gly Leu Gly Cys
20 25

<210> SEQ ID NO 36
<211> LENGTH: 28
<212> TYPE: PRT
<213> ORGANISM: Artificial Sequence -continued
<220> FEATURE:
<223> OTHER INFORMATION: Synthetic Polypeptide

<400> SEQUENCE: 36

```
Lys Gly Ala Asn Lys Lys Gly Leu Ser Lys Gly Cys Phe Gly Leu Lys
1               5                   10                  15

Leu Asp Arg Ile Gly Ser Met Ser Gly Leu Gly Cys
            20                  25
```

<210> SEQ ID NO 37
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 37

```
Gly Ala Asn Lys Lys Gly Leu Ser Lys Gly Cys Phe Gly Leu Lys Leu
1               5                   10                  15

Asp Arg Ile Gly Ser Met Ser Gly Leu Gly Cys
            20                  25
```

<210> SEQ ID NO 38
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 38

```
Ala Asn Lys Lys Gly Leu Ser Lys Gly Cys Phe Gly Leu Lys Leu Asp
1               5                   10                  15

Arg Ile Gly Ser Met Ser Gly Leu Gly Cys
            20                  25
```

<210> SEQ ID NO 39
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 39

```
Asn Lys Lys Gly Leu Ser Lys Gly Cys Phe Gly Leu Lys Leu Asp Arg
1               5                   10                  15

Ile Gly Ser Met Ser Gly Leu Gly Cys
            20                  25
```

<210> SEQ ID NO 40
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 40

```
Lys Lys Gly Leu Ser Lys Gly Cys Phe Gly Leu Lys Leu Asp Arg Ile
1               5                   10                  15

Gly Ser Met Ser Gly Leu Gly Cys
            20
```

<210> SEQ ID NO 41
<211> LENGTH: 23
<212> TYPE: PRT

<213> ORGANISM: Artificial Sequence
<220> FEATURE:
<223> OTHER INFORMATION: Synthetic Polypeptide

<400> SEQUENCE: 41

Lys Gly Leu Ser Lys Gly Cys Phe Gly Leu Lys Leu Asp Arg Ile Gly
1 5 10 15

Ser Met Ser Gly Leu Gly Cys
20

<210> SEQ ID NO 42
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 42

Leu Ser Lys Gly Cys Phe Gly Leu Lys Leu Asp Arg Ile Gly Ser Met
1 5 10 15

Ser Gly Leu Gly Cys
20

<210> SEQ ID NO 43
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 43

Ser Lys Gly Cys Phe Gly Leu Lys Leu Asp Arg Ile Gly Ser Met Ser
1 5 10 15

Gly Leu Gly Cys
20

<210> SEQ ID NO 44
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 44

Lys Gly Cys Phe Gly Leu Lys Leu Asp Arg Ile Gly Ser Met Ser Gly
1 5 10 15

Leu Gly Cys

<210> SEQ ID NO 45
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 45

Gly Cys Phe Gly Leu Lys Leu Asp Arg Ile Gly Ser Met Ser Gly Leu
1 5 10 15

Gly Cys

<210> SEQ ID NO 46
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 46

Gln Glu His Pro Asn Ala Arg Lys Tyr Lys Gly Ala Asn Lys Lys Gly
1 5 10 15

Leu Ser Lys Gly Cys Phe Gly Leu Lys Leu Asp Arg Ile Gly Ser Asn
20 25 30

Ser Gly Leu Gly Cys
35

<210> SEQ ID NO 47
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 47

Met Gln Glu His Pro Asn Ala Arg Lys Tyr Lys Gly Ala Asn Lys Lys
1 5 10 15

Gly Leu Ser Lys Gly Cys Phe Gly Leu Lys Leu Asp Arg Ile Gly Ser
20 25 30

Met Ser Gly Leu Gly Cys
35

<210> SEQ ID NO 48
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 48

Pro Gln Glu His Pro Asn Ala Arg Lys Tyr Lys Gly Ala Asn Lys Lys
1 5 10 15

Gly Leu Ser Lys Gly Cys Phe Gly Leu Lys Leu Asp Arg Ile Gly Ser
20 25 30

Met Ser Gly Leu Gly Cys
35

<210> SEQ ID NO 49
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 49

Gly Gln Glu His Pro Asn Ala Arg Lys Tyr Lys Gly Ala Asn Lys Lys
1 5 10 15

Gly Leu Ser Lys Gly Cys Phe Gly Leu Lys Leu Asp Arg Ile Gly Ser
20 25 30

Asn Ser Gly Leu Gly Cys
35

<210> SEQ ID NO 50
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 50

Met Gly Gln Glu His Pro Asn Ala Arg Lys Tyr Lys Gly Ala Asn Lys
1 5 10 15

Lys Gly Leu Ser Lys Gly Cys Phe Gly Leu Lys Leu Asp Arg Ile Gly
20 25 30

Ser Met Ser Gly Leu Gly Cys
35

<210> SEQ ID NO 51
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 51

Gly Gln Glu His Pro Asn Ala Arg Lys Tyr Lys Gly Ala Asn Lys Lys
1 5 10 15

Gly Leu Ser Lys Gly Cys Phe Gly Leu Lys Leu Asp Arg Ile Gly Ser
20 25 30

Met Ser Gly Leu Gly Cys
35

<210> SEQ ID NO 52
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 52

Gly Gln Glu His Pro Asn Ala Arg Lys Tyr Lys Gly Ala Asn Pro Lys
1 5 10 15

Gly Leu Ser Lys Gly Cys Phe Gly Leu Lys Leu Asp Arg Ile Gly Ser
20 25 30

Met Ser Gly Leu Gly Cys
35

<210> SEQ ID NO 53
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 53

Gly Gln Glu His Pro Asn Ala Arg Lys Tyr Lys Gly Ala Asn Gln Lys
1 5 10 15

Gly Leu Ser Lys Gly Cys Phe Gly Leu Lys Leu Asp Arg Ile Gly Ser
20 25 30

Met Ser Gly Leu Gly Cys
35

<210> SEQ ID NO 54
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 54

Gly Gln Glu His Pro Asn Ala Arg Lys Tyr Lys Gly Ala Asn Gln Gln

-continued

```
1               5                   10                  15

Gly Leu Ser Lys Gly Cys Phe Gly Leu Lys Leu Asp Arg Ile Gly Ser
            20                  25                  30

Met Ser Gly Leu Gly Cys
        35


<210> SEQ ID NO 55
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 55

Gly Gln Glu His Pro Asn Ala Arg Lys Tyr Lys Gly Ala Asn Lys Pro
1               5                   10                  15

Gly Leu Ser Lys Gly Cys Phe Gly Leu Lys Leu Asp Arg Ile Gly Ser
            20                  25                  30

Met Ser Gly Leu Gly Cys
        35


<210> SEQ ID NO 56
<211> LENGTH: 53
<212> TYPE: PRT
<213> ORGANISM: Artificial Sequence
<220> FEATURE:
<223> OTHER INFORMATION: Synthetic Polypeptide

<400> SEQUENCE: 56

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
    50


<210> SEQ ID NO 57
<211> LENGTH: 667
<212> TYPE: DNA
<213> ORGANISM: Artificial Sequence
<220> FEATURE:
<223> OTHER INFORMATION: Synthetic Polynucleotide

<400> SEQUENCE: 57

atggcactgc catccctgct actggtggtg gcagccctgg caggtggggt gcgtcctccg     60

ggggcacgga acctgacgct ggcggtggtg ctgccagaac acaacctgag ctatgcctgg    120

gcctggccac gggtgggtcc tgctgtggca ctggctgtgg aggcgctggg ccgggcactg    180

cccgtggacc tgcggtttgt cagctccgaa ctagacggcg cctgctctga gtacctggca    240

ccactgcgcg ctgtggatct caagctgtac catgaccccg accttctgtt gggccctggt    300

tgtgtgtacc ctgctgcctc tgtggctcgc tttgcctcgc actggcacct tcccctcctg    360

actgcgggtg cagtggcctc tggctttgca gctaagaatg agcattatcg taccctggtt    420

cgcactggcc cctctgcgcc caagctgggt gagttcgtag tgacattaca cgggcacttc    480

aattggactg ctcgggctgc tttgctgtat ctggatgctc gcacagatga ccggccccac    540

tacttcacca tcgagggggt gtttgaggcc ctgcagggca gcaacctcag tgtgcaacac    600
```

-continued

```
caggtgtata cccgagagcc aggtggccct gagcaagcca cccacttcat cagagccaac    660

gggcgca                                                              667


<210> SEQ ID NO 58
<211> LENGTH: 667
<212> TYPE: DNA
<213> ORGANISM: Artificial Sequence
<220> FEATURE:
<223> OTHER INFORMATION: Synthetic Polynucleotide

<400> SEQUENCE: 58

atggcactgc catccctgct actggtggtg gcagccctgg caggtggggt gcgtcctccg     60

ggggcacgga acctgacgct ggcggtggtg ctgccagaac acaacctgag ctatgcctgg    120

gcctggccac gggtgggtcc tgctgtggca ctggctgtgg aggcgctggg ccgggcactg    180

cccgtggacc tgcggtttgt cagctccgaa ctagacggcg cctgctctga gtacctggca    240

ccactgcgcg ctgtggatct caagctgtac catgaccccg accttctgtt gggccctggt    300

tgtgtgtacc ctgctgcctc tgtggctcgc tttgcctcgc actggcacct tcccctcctg    360

actgcgggtg cagtggcctc tggctttgca gctaagaatg agcattatcg taccctggtt    420

cgcactggcc cctctgcgcc caagctgggt gagttcgtag tgacattaca cgggcacttc    480

aattggactg ctcgggctgc tttgctgtat ctggatgctc gcacagatga ccggccccac    540

tacttcacca tcgagggggt gtttgaggcc ctgcagggca gcaacctcag tgtgcaacac    600

caggtgtata cccgagagcc aggtggccct gagcaagcca cccacttcat cagagccaac    660

gggcgca                                                              667


<210> SEQ ID NO 59
<211> LENGTH: 669
<212> TYPE: DNA
<213> ORGANISM: Artificial Sequence
<220> FEATURE:
<223> OTHER INFORMATION: Synthetic Polynucleotide

<400> SEQUENCE: 59

atggcactgc catccctgct actggtggtg gcagccctgg caggtggggt gcgtcctccg     60

ggggcacgga acctgacgct ggcggtggtg ctgccagaac acaacctgag ctatgcctgg    120

gcctggccac gggtgggtcc tgctgtggca ctggctgtgg aggcgctggg ccgggcactg    180

cccgtggacc tgcggtttgt cagctccgaa ctagacggcg cctgctctga gtacctggca    240

ccactgcgcg ctgtggatct caagctgtac catgaccccg accttctgtt gggccctggt    300

tgtgtgtacc ctgctgcctc tgtggctcgc tttgcctcgc actggcacct tcccctcctg    360

actgcgggtg cagtggcctc tggctttgca gctaagaatg agcattatcg taccctggtt    420

cgcactggcc cctctgcgcc caagctgggt gagttcgtag tgacattaca cgggcacttc    480

acaattggac tgctcgggct gctttgctgt atctggatgc tcgcacagat gaccggcccc    540

actacttcac catcgagggg gtgtttgagg ccctgcaggg cagcaacctc agtgtgcaac    600

accaggtgta tacccgagag ccaggtggcc ctgagcaagc cacccacttc atcagagcca    660

acgggcgca                                                            669


<210> SEQ ID NO 60
<211> LENGTH: 668
<212> TYPE: DNA
<213> ORGANISM: Artificial Sequence
<220> FEATURE:
<223> OTHER INFORMATION: Synthetic Polynucleotide
```

<400> SEQUENCE: 60
atggcactgc catccctgct actggtggtg gcagccctgg caggtggggt gcgtcctccg 60
ggggcacgga acctgacgct ggcggtggtg ctgccagaac acaacctgag ctatgcctgg 120
gcctggccac gggtgggtcc tgctgtggca ctggctgtgg aggcgctggg ccgggcactg 180
cccgtggacc tgcggtttgt cagctccgaa ctagacggcg cctgctctga gtacctggca 240
ccactgcgcg ctgtggatct caagctgtac catgaccccg accttctgtt gggccctggt 300
tgtgtgtacc ctgctgcctc tgtggctcgc tttgcctcgc actggcacct tcccctcctg 360
actgcgggtg cagtggcctc tggctttgca gctaagaatg agcattatcg taccctggtt 420
cgcactggcc cctctgcgcc caagctgggt gagttcgtag tgacattaca cgggcacttc 480
aattggactg ctcgggctgc tttgctgtat ctggatgctc gcacagatga ccggccccac 540
tacttcacca tccgaggggg tgtttgaggc cctgcagggc agcaacctca gtgtgcaaca 600
ccaggtgtat acccgagagc caggtggccc tgagcaagcc acccacttca tcagagccaa 660
cgggcgca 668

<210> SEQ ID NO 61
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 61
atggcactgc catccctgct actggtggtg gcagccctgg caggtggggt gcgtcctccg 60
ggggcacgga acctgacgct ggcggtggtg ctgccagaac acaacctgag ctatgcctgg 120
gcctggccac gggtgggtcc tgctgtggca ctggctgtgg aggcgctggg ccgggcactg 180
cccgtggacc tgcggtttgt cagctccgaa ctagacggcg cctgctctga gtacctggca 240
ccggggtgtt tgaggccctg cagggcagca acctcagtgt gcaacaccag gtgtataccc 300
gagagccagg tggccctgag caagccaccc acttcatcag agccaacggg cgca 354

<210> SEQ ID NO 62
<211> LENGTH: 1047
<212> TYPE: PRT
<213> ORGANISM: Artificial Sequence
<220> FEATURE:
<223> OTHER INFORMATION: Synthetic Polypeptide

<400> SEQUENCE: 62

Met Ala Leu Pro Ser Leu Leu Leu Val Val Ala Ala Leu Ala Gly Gly
1 5 10 15

Val Arg Pro Pro Gly Ala Arg Asn Leu Thr Leu Ala Val Val Leu Pro
20 25 30

Glu His Asn Leu Ser Tyr Ala Trp Ala Trp Pro Arg Val Gly Pro Ala
35 40 45

Val Ala Leu Ala Val Glu Ala Leu Gly Arg Ala Leu Pro Val Asp Leu
50 55 60

Arg Phe Val Ser Ser Glu Leu Asp Gly Ala Cys Ser Glu Tyr Leu Ala
65 70 75 80

Pro Leu Arg Ala Val Asp Leu Lys Leu Tyr His Asp Pro Asp Leu Leu
85 90 95

Leu Gly Pro Gly Cys Val Tyr Pro Ala Ala Ser Val Ala Arg Phe Ala
100 105 110

-continued

```
Ser His Trp His Leu Pro Leu Leu Thr Ala Gly Ala Val Ala Ser Gly
        115                 120                 125

Phe Ala Ala Lys Asn Glu His Tyr Arg Thr Leu Val Arg Thr Gly Pro
    130                 135                 140

Ser Ala Pro Lys Leu Gly Glu Phe Val Val Thr Leu His Gly His Phe
145                 150                 155                 160

Asn Trp Thr Ala Arg Ala Ala Leu Leu Tyr Leu Asp Ala Arg Thr Asp
                165                 170                 175

Asp Arg Pro His Tyr Phe Thr Ile Glu Gly Val Phe Glu Ala Leu Gln
            180                 185                 190

Gly Ser Asn Leu Ser Val Gln His Gln Val Tyr Thr Arg Glu Pro Gly
        195                 200                 205

Gly Pro Glu Gln Ala Thr His Phe Ile Arg Ala Asn Gly Arg Ile Val
    210                 215                 220

Tyr Ile Cys Gly Pro Leu Glu Met Leu His Glu Ile Leu Leu Gln Ala
225                 230                 235                 240

Gln Arg Glu Asn Leu Thr Asn Gly Asp Tyr Val Phe Phe Tyr Leu Asp
                245                 250                 255

Val Phe Gly Glu Ser Leu Arg Ala Gly Pro Thr Arg Ala Thr Gly Arg
            260                 265                 270

Pro Trp Gln Asp Asn Arg Thr Gln Glu Gln Ala Gln Ala Leu Arg Glu
        275                 280                 285

Ala Phe Gln Thr Val Leu Val Ile Thr Tyr Arg Glu Pro Pro Asn Pro
    290                 295                 300

Glu Tyr Gln Glu Phe Gln Asn Arg Leu Leu Ile Arg Ala Arg Glu Asp
305                 310                 315                 320

Phe Gly Val Glu Leu Ala Pro Ser Leu Met Asn Leu Ile Ala Gly Cys
                325                 330                 335

Phe Tyr Asp Gly Ile Leu Leu Tyr Ala Gln Val Leu Asn Glu Thr Ile
            340                 345                 350

Gln Glu Gly Gly Thr Arg Glu Asp Gly Leu Arg Ile Val Glu Lys Met
        355                 360                 365

Gln Gly Arg Arg Tyr His Gly Val Thr Gly Leu Val Val Met Asp Lys
    370                 375                 380

Asn Asn Asp Arg Glu Thr Asp Phe Val Leu Trp Ala Met Gly Asp Leu
385                 390                 395                 400

Glu Ser Gly Asp Phe Gln Pro Ala Ala His Tyr Ser Gly Ala Glu Lys
                405                 410                 415

Gln Ile Trp Trp Thr Gly Arg Pro Ile Pro Trp Val Lys Gly Ala Pro
            420                 425                 430

Pro Leu Asp Asn Pro Pro Cys Ala Phe Asp Leu Asp Asp Pro Ser Cys
        435                 440                 445

Asp Lys Thr Pro Leu Ser Thr Leu Ala Ile Val Ala Leu Gly Thr Gly
    450                 455                 460

Ile Thr Phe Ile Met Phe Gly Val Ser Ser Phe Leu Ile Phe Arg Lys
465                 470                 475                 480

Leu Met Leu Glu Lys Glu Leu Ala Ser Met Leu Trp Arg Ile Arg Trp
                485                 490                 495

Glu Glu Leu Gln Phe Gly Asn Ser Asp Arg Tyr His Lys Gly Ala Gly
            500                 505                 510

Ser Arg Leu Thr Leu Ser Leu Arg Gly Ser Ser Tyr Gly Ser Leu Met
        515                 520                 525
```

-continued

```
Thr Ala His Gly Lys Tyr Gln Ile Phe Ala Asn Thr Gly His Phe Lys
    530                 535                 540

Gly Asn Val Val Ala Ile Lys His Val Asn Lys Lys Arg Ile Glu Leu
545                 550                 555                 560

Thr Arg Gln Val Leu Phe Glu Leu Lys His Met Arg Asp Val Gln Phe
                565                 570                 575

Asn His Leu Thr Arg Phe Ile Gly Ala Cys Ile Asp Pro Pro Asn Ile
                580                 585                 590

Cys Ile Val Thr Glu Tyr Cys Pro Arg Gly Ser Leu Gln Asp Ile Leu
        595                 600                 605

Glu Asn Asp Ser Ile Asn Leu Asp Trp Met Phe Arg Tyr Ser Leu Ile
    610                 615                 620

Asn Asp Leu Val Lys Gly Met Ala Phe Leu His Asn Ser Ile Ile Ser
625                 630                 635                 640

Ser His Gly Ser Leu Lys Ser Ser Asn Cys Val Val Asp Ser Arg Phe
                645                 650                 655

Val Leu Lys Ile Thr Asp Tyr Gly Leu Ala Ser Phe Arg Ser Thr Ala
                660                 665                 670

Glu Pro Asp Asp Ser His Ala Leu Tyr Ala Lys Lys Leu Trp Thr Ala
        675                 680                 685

Pro Glu Leu Leu Ser Gly Asn Pro Leu Pro Thr Thr Gly Met Gln Lys
    690                 695                 700

Ala Asp Val Tyr Ser Phe Ala Ile Ile Leu Gln Glu Ile Ala Leu Arg
705                 710                 715                 720

Ser Gly Pro Phe Tyr Leu Glu Gly Leu Asp Leu Ser Pro Lys Glu Ile
                725                 730                 735

Val Gln Lys Val Arg Asn Gly Gln Arg Pro Tyr Phe Arg Pro Ser Ile
                740                 745                 750

Asp Arg Thr Gln Leu Asn Glu Glu Leu Val Leu Leu Met Glu Arg Cys
        755                 760                 765

Trp Ala Gln Asp Pro Thr Glu Arg Pro Asp Phe Gly Gln Ile Lys Gly
    770                 775                 780

Phe Ile Arg Arg Phe Asn Lys Glu Gly Gly Thr Ser Ile Leu Asp Asn
785                 790                 795                 800

Leu Leu Leu Arg Met Glu Gln Tyr Ala Asn Asn Leu Glu Lys Leu Val
                805                 810                 815

Glu Glu Arg Thr Gln Ala Tyr Leu Glu Glu Lys Arg Lys Ala Glu Ala
                820                 825                 830

Leu Leu Tyr Gln Ile Leu Pro His Ser Val Ala Glu Gln Leu Lys Arg
        835                 840                 845

Gly Glu Thr Val Gln Ala Glu Ala Phe Asp Ser Val Thr Ile Tyr Phe
    850                 855                 860

Ser Asp Ile Val Gly Phe Thr Ala Leu Ser Ala Glu Ser Thr Pro Met
865                 870                 875                 880

Gln Val Val Thr Leu Leu Asn Asp Leu Tyr Thr Cys Phe Asp Ala Ile
                885                 890                 895

Ile Asp Asn Phe Asp Val Tyr Lys Val Glu Thr Ile Gly Asp Ala Tyr
                900                 905                 910

Met Val Val Ser Gly Leu Pro Gly Arg Asn Gly Gln Arg His Ala Pro
        915                 920                 925

Glu Ile Ala Arg Met Ala Leu Ala Leu Leu Asp Ala Val Ser Ser Phe
    930                 935                 940

Arg Ile Arg His Arg Pro His Asp Gln Leu Arg Leu Arg Ile Gly Val
```

-continued

```
945                 950                 955                 960

His Thr Gly Pro Val Cys Ala Gly Val Val Gly Leu Lys Met Pro Arg
                965                 970                 975

Tyr Cys Leu Phe Gly Asp Thr Val Asn Thr Ala Ser Arg Met Glu Ser
            980                 985                 990

Asn Gly Gln Ala Leu Lys Ile His  Val Ser Ser Thr Thr  Lys Asp Ala
        995                 1000                1005

Leu Asp  Glu Leu Gly Cys Phe  Gln Leu Glu Leu Arg  Gly Asp Val
    1010                 1015                 1020

Glu Met  Lys Gly Lys Gly Lys  Met Arg Thr Tyr Trp  Leu Leu Gly
    1025                 1030                 1035

Glu Arg  Lys Gly Pro Pro Gly  Leu Leu
    1040                 1045


<210> SEQ ID NO 63
<211> LENGTH: 1047
<212> TYPE: PRT
<213> ORGANISM: Artificial Sequence
<220> FEATURE:
<223> OTHER INFORMATION: Synthetic Polypeptide

<400> SEQUENCE: 63

Met Ala Leu Pro Ser Leu Leu Leu Val Val Ala Ala Leu Ala Gly Gly
1               5                   10                  15

Val Arg Pro Pro Gly Ala Arg Asn Leu Thr Leu Ala Val Val Leu Pro
            20                  25                  30

Glu His Asn Leu Ser Tyr Ala Trp Ala Trp Pro Arg Val Gly Pro Ala
        35                  40                  45

Val Ala Leu Ala Val Glu Ala Leu Gly Arg Ala Leu Pro Val Asp Leu
    50                  55                  60

Arg Phe Val Ser Ser Glu Leu Asp Gly Ala Cys Ser Glu Tyr Leu Ala
65                  70                  75                  80

Pro Leu Arg Ala Val Asp Leu Lys Leu Tyr His Asp Pro Asp Leu Leu
                85                  90                  95

Leu Gly Pro Gly Cys Val Tyr Pro Ala Ala Ser Val Ala Arg Phe Ala
            100                 105                 110

Ser His Trp His Leu Pro Leu Leu Thr Ala Gly Ala Val Ala Ser Gly
        115                 120                 125

Phe Ala Ala Lys Asn Glu His Tyr Arg Thr Leu Val Arg Thr Gly Pro
    130                 135                 140

Ser Ala Pro Lys Leu Gly Glu Phe Val Val Thr Leu His Gly His Phe
145                 150                 155                 160

Asn Trp Thr Ala Arg Ala Ala Leu Leu Tyr Leu Asp Ala Arg Thr Asp
                165                 170                 175

Asp Arg Pro His Tyr Phe Thr Ile Glu Gly Val Phe Glu Ala Leu Gln
            180                 185                 190

Gly Ser Asn Leu Ser Val Gln His Gln Val Tyr Thr Arg Glu Pro Gly
        195                 200                 205

Gly Pro Glu Gln Ala Thr His Phe Ile Arg Ala Asn Gly Arg Ile Val
    210                 215                 220

Tyr Ile Cys Gly Pro Leu Glu Met Leu His Glu Ile Leu Leu Gln Ala
225                 230                 235                 240

Gln Arg Glu Asn Leu Thr Asn Gly Asp Tyr Val Phe Phe Tyr Leu Asp
                245                 250                 255

Val Phe Gly Glu Ser Leu Arg Ala Gly Pro Thr Arg Ala Thr Gly Arg
```

-continued

```
            260                 265                 270

Pro Trp Gln Asp Asn Arg Thr Gln Glu Gln Ala Gln Ala Leu Arg Glu
        275                 280                 285

Ala Phe Gln Thr Val Leu Val Ile Thr Tyr Arg Glu Pro Pro Asn Pro
    290                 295                 300

Glu Tyr Gln Glu Phe Gln Asn Arg Leu Leu Ile Arg Ala Arg Glu Asp
305                 310                 315                 320

Phe Gly Val Glu Leu Ala Pro Ser Leu Met Asn Leu Ile Ala Gly Cys
                325                 330                 335

Phe Tyr Asp Gly Ile Leu Leu Tyr Ala Gln Val Leu Asn Glu Thr Ile
            340                 345                 350

Gln Glu Gly Gly Thr Arg Glu Asp Gly Leu Arg Ile Val Glu Lys Met
        355                 360                 365

Gln Gly Arg Arg Tyr His Gly Val Thr Gly Leu Val Val Met Asp Lys
    370                 375                 380

Asn Asn Asp Arg Glu Thr Asp Phe Val Leu Trp Ala Met Gly Asp Leu
385                 390                 395                 400

Glu Ser Gly Asp Phe Gln Pro Ala Ala His Tyr Ser Gly Ala Glu Lys
                405                 410                 415

Gln Ile Trp Trp Thr Gly Arg Pro Ile Pro Trp Val Lys Gly Ala Pro
            420                 425                 430

Pro Leu Asp Asn Pro Pro Cys Ala Phe Asp Leu Asp Asp Pro Ser Cys
        435                 440                 445

Asp Lys Thr Pro Leu Ser Thr Leu Ala Ile Val Ala Leu Gly Thr Gly
    450                 455                 460

Ile Thr Phe Ile Met Phe Gly Val Ser Ser Phe Leu Ile Phe Arg Lys
465                 470                 475                 480

Leu Met Leu Glu Lys Glu Leu Ala Ser Met Leu Trp Arg Ile Arg Trp
                485                 490                 495

Glu Glu Leu Gln Phe Gly Asn Ser Asp Arg Tyr His Lys Gly Ala Gly
            500                 505                 510

Ser Arg Leu Thr Leu Ser Leu Arg Gly Ser Ser Tyr Gly Ser Leu Met
        515                 520                 525

Thr Ala His Gly Lys Tyr Gln Ile Phe Ala Asn Thr Gly His Phe Lys
    530                 535                 540

Gly Asn Val Val Ala Ile Lys His Val Asn Lys Lys Arg Ile Glu Leu
545                 550                 555                 560

Thr Arg Gln Val Leu Phe Glu Leu Lys His Met Arg Asp Val Gln Phe
                565                 570                 575

Asn His Leu Thr Arg Phe Ile Gly Ala Cys Ile Asp Pro Pro Asn Ile
            580                 585                 590

Cys Ile Val Thr Glu Tyr Cys Pro Arg Gly Ser Leu Gln Asp Ile Leu
        595                 600                 605

Glu Asn Asp Ser Ile Asn Leu Asp Trp Met Phe Arg Tyr Ser Leu Ile
    610                 615                 620

Asn Asp Leu Val Lys Gly Met Ala Phe Leu His Asn Ser Ile Ile Ser
625                 630                 635                 640

Ser His Gly Ser Leu Lys Ser Ser Asn Cys Val Val Asp Ser Arg Phe
                645                 650                 655

Val Leu Lys Ile Thr Asp Tyr Gly Leu Ala Ser Phe Arg Ser Thr Ala
            660                 665                 670

Glu Pro Asp Asp Ser His Ala Leu Tyr Ala Lys Lys Leu Trp Thr Ala
        675                 680                 685
```

-continued

```
Pro Glu Leu Leu Ser Gly Asn Pro Leu Pro Thr Thr Gly Met Gln Lys
    690                 695                 700

Ala Asp Val Tyr Ser Phe Ala Ile Ile Leu Gln Glu Ile Ala Leu Arg
705                 710                 715                 720

Ser Gly Pro Phe Tyr Leu Glu Gly Leu Asp Leu Ser Pro Lys Glu Ile
                725                 730                 735

Val Gln Lys Val Arg Asn Gly Gln Arg Pro Tyr Phe Arg Pro Ser Ile
            740                 745                 750

Asp Arg Thr Gln Leu Asn Glu Glu Leu Val Leu Leu Met Glu Arg Cys
        755                 760                 765

Trp Ala Gln Asp Pro Thr Glu Arg Pro Asp Phe Gly Gln Ile Lys Gly
    770                 775                 780

Phe Ile Arg Arg Phe Asn Lys Glu Gly Gly Thr Ser Ile Leu Asp Asn
785                 790                 795                 800

Leu Leu Leu Arg Met Glu Gln Tyr Ala Asn Asn Leu Glu Lys Leu Val
                805                 810                 815

Glu Glu Arg Thr Gln Ala Tyr Leu Glu Glu Lys Arg Lys Ala Glu Ala
            820                 825                 830

Leu Leu Tyr Gln Ile Leu Pro His Ser Val Ala Glu Gln Leu Lys Arg
        835                 840                 845

Gly Glu Thr Val Gln Ala Glu Ala Phe Asp Ser Val Thr Ile Tyr Phe
    850                 855                 860

Ser Asp Ile Val Gly Phe Thr Ala Leu Ser Ala Glu Ser Thr Pro Met
865                 870                 875                 880

Gln Val Val Thr Leu Leu Asn Asp Leu Tyr Thr Cys Phe Asp Ala Ile
                885                 890                 895

Ile Asp Asn Phe Asp Val Tyr Lys Val Glu Thr Ile Gly Asp Ala Tyr
            900                 905                 910

Met Val Val Ser Gly Leu Pro Gly Arg Asn Gly Gln Arg His Ala Pro
        915                 920                 925

Glu Ile Ala Arg Met Ala Leu Ala Leu Leu Asp Ala Val Ser Ser Phe
    930                 935                 940

Arg Ile Arg His Arg Pro His Asp Gln Leu Arg Leu Arg Ile Gly Val
945                 950                 955                 960

His Thr Gly Pro Val Cys Ala Gly Val Val Gly Leu Lys Met Pro Arg
                965                 970                 975

Tyr Cys Leu Phe Gly Asp Thr Val Asn Thr Ala Ser Arg Met Glu Ser
            980                 985                 990

Asn Gly Gln Ala Leu Lys Ile His  Val Ser Ser Thr Thr  Lys Asp Ala
        995                 1000                1005

Leu Asp  Glu Leu Gly Cys Phe  Gln Leu Glu Leu Arg  Gly Asp Val
    1010                 1015                1020

Glu Met  Lys Gly Lys Gly Lys  Met Arg Thr Tyr Trp  Leu Leu Gly
    1025                 1030                1035

Glu Arg  Lys Gly Pro Pro Gly  Leu Leu
    1040                 1045
```

<210> SEQ ID NO 64
<211> LENGTH: 245
<212> TYPE: PRT
<213> ORGANISM: Artificial Sequence
<220> FEATURE:
<223> OTHER INFORMATION: Synthetic Polypeptide

<400> SEQUENCE: 64

```
Met Ala Leu Pro Ser Leu Leu Leu Val Val Ala Ala Leu Ala Gly Gly
1               5                   10                  15

Val Arg Pro Pro Gly Ala Arg Asn Leu Thr Leu Ala Val Val Leu Pro
            20                  25                  30

Glu His Asn Leu Ser Tyr Ala Trp Ala Trp Pro Arg Val Gly Pro Ala
        35                  40                  45

Val Ala Leu Ala Val Glu Ala Leu Gly Arg Ala Leu Pro Val Asp Leu
    50                  55                  60

Arg Phe Val Ser Ser Glu Leu Asp Gly Ala Cys Ser Glu Tyr Leu Ala
65                  70                  75                  80

Pro Leu Arg Ala Val Asp Leu Lys Leu Tyr His Asp Pro Asp Leu Leu
                85                  90                  95

Leu Gly Pro Gly Cys Val Tyr Pro Ala Ala Ser Val Ala Arg Phe Ala
            100                 105                 110

Ser His Trp His Leu Pro Leu Leu Thr Ala Gly Ala Val Ala Ser Gly
        115                 120                 125

Phe Ala Ala Lys Asn Glu His Tyr Arg Thr Leu Val Arg Thr Gly Pro
    130                 135                 140

Ser Ala Pro Lys Leu Gly Glu Phe Val Val Thr Leu His Gly His Phe
145                 150                 155                 160

Thr Ile Gly Leu Leu Gly Leu Leu Cys Cys Ile Trp Met Leu Ala Gln
                165                 170                 175

Met Thr Gly Pro Thr Thr Ser Pro Ser Arg Gly Cys Leu Arg Pro Cys
            180                 185                 190

Arg Ala Ala Thr Ser Val Cys Asn Thr Arg Cys Ile Pro Glu Ser Gln
        195                 200                 205

Val Ala Leu Ser Lys Pro Pro Thr Ser Ser Glu Pro Thr Gly Ala Leu
    210                 215                 220

Cys Ile Ser Ala Ala Arg Trp Arg Cys Phe Met Arg Ser Cys Phe Arg
225                 230                 235                 240

Pro Arg Gly Arg Thr
                245
```

<210> SEQ ID NO 65
<211> LENGTH: 188
<212> TYPE: PRT
<213> ORGANISM: Artificial Seuqence
<220> FEATURE:
<223> OTHER INFORMATION: Synthetic Polypeptide

<400> SEQUENCE: 65

```
Met Ala Leu Pro Ser Leu Leu Leu Val Val Ala Ala Leu Ala Gly Gly
1               5                   10                  15

Val Arg Pro Pro Gly Ala Arg Asn Leu Thr Leu Ala Val Val Leu Pro
            20                  25                  30

Glu His Asn Leu Ser Tyr Ala Trp Ala Trp Pro Arg Val Gly Pro Ala
        35                  40                  45

Val Ala Leu Ala Val Glu Ala Leu Gly Arg Ala Leu Pro Val Asp Leu
    50                  55                  60

Arg Phe Val Ser Ser Glu Leu Asp Gly Ala Cys Ser Glu Tyr Leu Ala
65                  70                  75                  80

Pro Leu Arg Ala Val Asp Leu Lys Leu Tyr His Asp Pro Asp Leu Leu
                85                  90                  95

Leu Gly Pro Gly Cys Val Tyr Pro Ala Ala Ser Val Ala Arg Phe Ala
            100                 105                 110
```

-continued

```
Ser His Trp His Leu Pro Leu Leu Thr Ala Gly Ala Val Ala Ser Gly
        115                 120                 125

Phe Ala Ala Lys Asn Glu His Tyr Arg Thr Leu Val Arg Thr Gly Pro
    130                 135                 140

Ser Ala Pro Lys Leu Gly Glu Phe Val Val Thr Leu His Gly His Phe
145                 150                 155                 160

Asn Trp Thr Ala Arg Ala Ala Leu Leu Tyr Leu Asp Ala Arg Thr Asp
                165                 170                 175

Asp Arg Pro His Tyr Phe Thr Ile Arg Gly Gly Val
            180                 185


<210> SEQ ID NO 66
<211> LENGTH: 140
<212> TYPE: PRT
<213> ORGANISM: Artificial Sequence
<220> FEATURE:
<223> OTHER INFORMATION: Synthetic Polypeptide

<400> SEQUENCE: 66

Met Ala Leu Pro Ser Leu Leu Leu Val Val Ala Ala Leu Ala Gly Gly
1               5                   10                  15

Val Arg Pro Pro Gly Ala Arg Asn Leu Thr Leu Ala Val Val Leu Pro
            20                  25                  30

Glu His Asn Leu Ser Tyr Ala Trp Ala Trp Pro Arg Val Gly Pro Ala
        35                  40                  45

Val Ala Leu Ala Val Glu Ala Leu Gly Arg Ala Leu Pro Val Asp Leu
    50                  55                  60

Arg Phe Val Ser Ser Glu Leu Asp Gly Ala Cys Ser Glu Tyr Leu Ala
65                  70                  75                  80

Pro Gly Cys Leu Arg Pro Cys Arg Ala Ala Thr Ser Val Cys Asn Thr
                85                  90                  95

Arg Cys Ile Pro Glu Ser Gln Val Ala Leu Ser Lys Pro Pro Thr Ser
            100                 105                 110

Ser Glu Pro Thr Gly Ala Leu Cys Ile Ser Ala Ala Arg Trp Arg Cys
        115                 120                 125

Phe Met Arg Ser Cys Phe Arg Pro Arg Gly Arg Thr
    130                 135                 140


<210> SEQ ID NO 67
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 67

Cys Phe Gly Leu Lys Leu Asp Arg Ile Gly Ser Met Ser Gly Leu Gly
1               5                   10                  15

Cys


<210> SEQ ID NO 68
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 68

Gly Leu Ser Lys Gly Cys Phe Gly Leu Lys Leu Asp Arg Ile Gly Ser
```

-continued

```
1               5                  10                 15

Met Ser Gly Leu Gly Cys
            20
```

CNP VARIANTS AND CONJUGATES THEREOF

CROSS-REFERENCE TO RELATED APPLICATIONS

The present application is a national stage of PCT/US2020/51100, filed Sep. 16, 2020 which claims the priority benefit of U.S. Provisional Patent Application No. 62/901,093, filed Sep. 16, 2019, U.S. Provisional Patent Application No. 62/935,050, filed Nov. 13, 2019, U.S. Provisional Patent Application No. 62/963,350, filed Jan. 20, 2020, U.S. Provisional Patent Application No. 62/964,852, filed Jan. 23, 2020, and U.S. Provisional Patent Application No. 63/038,667, filed Jun. 12, 2020, herein incorporated by reference in their entireties.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "54736_Seqlisting.txt", which was created on Aug. 6, 2020 and is 54,429 bytes in size. The subject matter of the Sequence Listing is incorporated herein in its entirety by reference.

FIELD OF THE DISCLOSURE

The present disclosure, relates, in general, to variants of C-type natriuretic peptide (CNP), pharmaceutical compositions comprising CNP variants and methods of use. The CNP variants are useful as therapeutic agents for the treatment of diseases responsive to CNP, including but not limited to bone-related disorders, such as skeletal dysplasias (e.g., achondroplasia).

BACKGROUND

C-type natriuretic peptide (CNP) (Biochem. Biophys. Res. Commun., 168: 863-870 (1990) (GenBank Accession No. NP_077720, for the CNP precursor protein, NPPC) (J. Hypertens., 10: 907-912 (1992)) is a small, single chain peptide in a family of peptides (ANP, BNP, CNP) having a 17-amino acid loop structure (Levin et al., N. Engl. J. Med., 339: 863-870 (1998)) and have important roles in multiple biological processes. CNP interacts with natriuretic peptide receptor-B (NPR-B, GC-B) to stimulate the generation of cyclic- guanosine monophosphate (cGMP) (J. Hypertens., 10: 1111-1114 (1992)). CNP is expressed widely, including in the central nervous system, reproductive tract, bone and endothelium of blood vessels (Hypertension, 49: 419-426 (2007)).

In humans, CNP is initially produced from the natriuretic peptide precursor C (NPPC) gene as a single chain 126-amino acid pre-pro polypeptide (Biochem. Biophys. Res. Commun., 168: 863-870 (1990)). Removal of the signal peptide yields pro-CNP, and further cleavage by the endoprotease furin generates an active 53-amino acid peptide (CNP-53), which is secreted and cleaved again by an unknown enzyme to produce the mature 22-amino acid peptide (CNP-22) (Wu, J. Biol. Chem. 278: 25847-852 (2003)). CNP-53 and CNP-22 differ in their distribution, with CNP-53 predominating in tissues, while CNP-22 is mainly found in plasma and cerebrospinal fluid (J. Alfonzo, Recept. Signal. Transduct. Res., 26: 269-297 (2006)). Both CNP-53 and CNP-22 bind similarly to NPR-B.

Downstream signaling mediated by cGMP generation influences a diverse array of biological processes that include endochondral ossification. For example, knockout of either CNP or NPR-B in mouse models results in animals having a dwarfed phenotype with shorter long bones and vertebrae. Mutations in human NPR-B that block proper CNP signaling have been identified and result in dwarfism (Olney, et al., J. Clin. Endocrinol. Metab. 91(4): 1229-1232 (2006); Bartels, et al., Am. J. Hum. Genet. 75: 27-34 (2004)). In contrast, mice engineered to produce elevated levels of CNP display elongated long bones and vertebrae.

Therapeutic use of CNP (CNP22) has been limited by its short plasma half-life, which has been shown to be 2.6 minutes in vivo in humans (J Clin. Endocrinol. Metab., 78: 1428-35 (1994)). A CNP variant having a longer in vivo serum half-life and exhibiting similar or improved activity to that of wild-type CNP is important for a sustainable therapeutic strategy.

SUMMARY

The present disclosure relates to novel variants of C-type natriuretic peptide (CNP) having increased circulating half-life and stability in aqueous media, pharmaceutical compositions comprising such CNP variants, and methods of using such CNP variants to treat disorders responsive to CNP, including but not limited to bone-related disorders such as achondroplasia.

In various embodiments, the disclosure provides a variant of C-type natriuretic peptide (CNP) selected from the group consisting of

```
                                      (SEQ ID NO: 5)
PGQEHPQARRYRGAQRRGLSRGCFGLKLDRIGSMSGLGC;

                                      (SEQ ID NO: 1)
PGQEHPNARKYKGANKKGLSKGCFGLKLDRIGSMSGLGC;

                                      (SEQ ID NO: 6)
PGQEHPNARRYRGANRRGLSRGCFGLKLDRIGSMSGLGC;
and

                                      (SEQ ID NO: 5)
PGQEHPQARRYRGAQRRGLSRGCFGLKLDRIGSMSGLGC.
```

In various embodiments, the disclosure provides a variant of C-type natriuretic peptide (CNP) selected from the group consisting of

```
                                      (SEQ ID NO: 5)
PGQEHPQARRYRGAQRRGLSRGCFGLKLDRIGSMSGLGC;

                                      (SEQ ID NO: 1)
PGQEHPNARKYKGANKKGLSKGCFGLKLDRIGSMSGLGC;

                                      (SEQ ID NO: 6)
PGQEHPNARRYRGANRRGLSRGCFGLKLDRIGSMSGLGC;

                                      (SEQ ID NO: 5)
PGQEHPQARRYRGAQRRGLSRGCFGLKLDRIGSMSGLGC;
and

                                      (SEQ ID NO: 7)
PGQEHPQARKYKGAQKKGLSKGCFGLKLDRIGSMSGLGC.
```

In various embodiments, the variant peptide further comprises an acetyl group. In various embodiments, the acetyl group is on the N-terminus of the peptide. In various embodiments, the peptide further comprises an OH or an $NH_2$ group at the C-terminus.

In various embodiments, the variant peptide comprises a conjugate moiety. In various embodiments, the conjugate moiety is on a residue of the CNP cyclic domain or at a site other than the CNP cyclic domain. In various embodiments, the conjugate moiety is on a lysine residue. In various embodiments, the conjugate moiety comprises one or more acid moieties. In various embodiments, the acid moiety is a hydrophobic acid.

In various embodiments, the conjugate moiety comprises one or more acid moieties linked to a hydrophilic spacer. In various embodiments, the hydrophilic spacer is any amino acid. In various embodiments, the hydrophilic spacer is gamma glutamic acid (γGlu). In various embodiments, the hydrophilic spacer is OEG (8-amino-3,6-dioxaoctanoic acid). In various embodiments, the hydrophilic spacer is gamma glutamic acid (γGlu) or OEG (8-amino-3,6-dioxaoctanoic acid). In various embodiments, the hydrophilic spacer is gamma glutamic acid (γGlu) linked to one or two or more OEG (8-amino-3,6-dioxaoctanoic acid). In various embodiments, the acid moiety is a fatty acid. Exemplary fatty acids include short chain, medium chain, or long chain fatty acids, or a dicarboxylic fatty acid. In various embodiments, the fatty acid is saturated or unsaturated. Contemplated are C-6 to C-20 fatty acids, including but not limited to, C-6, C-8, C-10, C-12, C-14, C-16, C-18 or C-20 fatty acids, saturated or unsaturated. In various embodiments, the fatty acid is decanoic acid, dodecanoic acid, myristic acid, palmitic acid, stearic acid, arachidic acid, or diacids of the same.

In various embodiments, the acid moiety and the hydrophilic spacer have the structure AEEA-AEEA-γGlu-C18DA. In various embodiments, the acid moiety and the hydrophilic spacer have the structure:

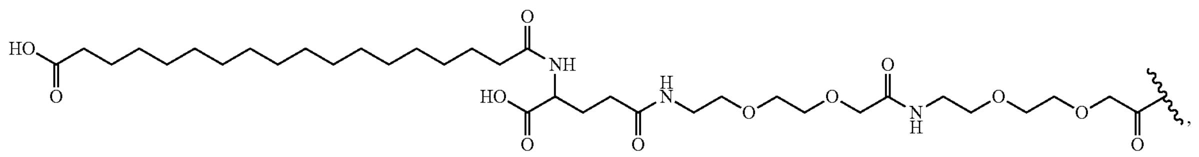 [SMILES: *C(=O)COCCOCCNC(=O)COCCOCCNC(=O)CCC(NC(=O)CCCCCCCCCCCCCCCCC(=O)O)C(=O)O]

wherein "~" represents the point of attachment to a CNP variant. In various embodiments, "~" represents the point of attachment to a hydrolysable linker, wherein the hydrolysable linker is attached to a CNP variant. In various embodiments, the hydrolysable linker is capable of releasing intact CNP variant.

In various embodiments, the CNP variant with the conjugate moiety is a component of modified release composition. In various embodiments, the modified release composition is an extended release composition. In various embodiments, the CNP variant comprising a conjugate moiety and hydrolysable linker is capable of releasing the CNP variant, wherein (i) less than about 20% of CNP variant is released by day 1; and (ii) about 90% of the CNP variant is released weekly, or about 90% of the CNP variant is released bi-weekly, or about 90% of the CNP variant is released monthly, at pH 7 to 7.6.

In various embodiments, (i) less than about 25%, about 30%, about 35%, about 40%, about 45%, about 50%, about 55%, about 60%, about 65%, about 70%, or about 75% of peptide is released by day 1, at pH 7.0 to 7.6; and (ii) about 90% of peptide is released weekly, or about 90% of peptide is released bi-weekly, or about 90% of peptide is released monthly, at pH 7 to 7.6. It is further contemplated that (i) less than about 25%, about 30%, about 35%, about 40%, about 45%, about 50%, about 55%, about 60% about 65%, about 70%, or about 75% of peptide is released by day 1, at pH 7.0 to 7.6; and (ii) about 70%, about 80%, or about 90% of peptide is released weekly; or about 70%, about 80%, or about 90% of peptide is released bi-weekly; or about 70%, about 80%, or about 90% of peptide is released every three weeks; or about 70%, about 80%, or about 90% of peptide is released monthly, at pH 7 to 7.6; or alternatively ii) about 70%, about 75%, about 80%, about 85%, or about 90% of peptide is released weekly; or about 70%, about 75%, about 80%, about 85%, or about 90% of peptide is released bi-weekly; or about 70%, about 75%, about 80%, about 85%, or about 90% of peptide is released every three weeks; or about 70%, about 75%, about 80%, about 85%, or about 90% of peptide is released monthly, at pH 7 to 7.6

In various embodiments, the variant has the structure:

(SEQ ID NO: 5)
PGQEHPQARRYRGAQRRGLSRGCFGLK(AEEA-AEEA-γGlu-C18DA) LDRIGSMSGLGC, or (SEQ ID NO: 8)
Ac-PGQEHPQARRYRGAQRRGLSRGCFGLK(AEEA-AEEA-γGlu-C18DA)LDRIGSMSGLGC-OH.

In various embodiments, the variant is selected from the group consisting of (SEQ ID NO: 8)
Ac-PGQEHPQARRYRGAQRRGLSRGCFGLKLDRIGSMSGLGC-OH;

(SEQ ID NO: 9)
Ac-PGQEHPNARKYKGANKKGLSKGCFGLKLDRIGSMSGLGC-$NH_2$;

(SEQ ID NO: 10)
Ac-PGQEHPNARRYRGANRRGLSRGCFGLKLDRIGSMSGLGC-OH;

(SEQ ID NO: 11)
Ac-PGQEHPNARRYRGANRRGLSRGCFGLKLDRIGSMSGLGC-$NH_2$;

(SEQ ID NO: 12)
Ac-PGQEHPQARRYRGAQRRGLSRGCFGLKLDRIGSMSGLGC-$NH_2$;

(SEQ ID NO: 13)
Ac-PGQEHPQARKYKGAQKKGLSKGCFGLKLDRIGSMSGLGC-$NH_2$;

and (SEQ ID NO: 14)
Ac-PGQEHPQARKYKGAQKKGLSKGCFGLKLDRIGSMSGLGC-OH.

In various embodiments, the variant comprises one or more linker groups. In various embodiments, the linker is on a residue of the CNP cyclic domain or at a site other than the CNP cyclic domain. In various embodiments, the linker is on a lysine residue.

In various embodiments, the linker is a hydrolysable linker.

In various embodiments, the CNP variant is attached to the conjugate moiety via the linker. In various embodiments, the linker is attached to the conjugate moiety via the hydrophilic spacer of the conjugate moiety. In various embodiments, the linker is aminoethoxy-2-ethoxy acetic acid (AEEA). In various embodiments, the linker is a bicin-type or peptoid linker, which refers to a linker having a similar cleavage mechanism as bicin (bis-2-hydroxyethylglycinamide), but cleaving instead via an asymmetric N-alkyl peptide, i.e., a peptoid. In various embodiments, the linker is an electronic linker based on nonenzymatic β-elimination. In various embodiments, the electronic linker comprises an $SO_2$ moiety. Examples of linkers as illustrated in a CNP conjugate are set out in FIG. 1. See also Santi, et. al., Proc Natl Acad Sci USA 109:6211-6216, 2012).

In various embodiments, the conjugate moiety is a synthetic polymeric group. In various embodiments, the variant comprises a synthetic polymeric group coupled to the variant through a hydrolysable linker. In various embodiments, the synthetic polymeric group comprises a hydrophilic polymer moiety. In various embodiments, the hydrophilic polymer moiety comprises polyethylene glycol (PEG). In various embodiments, the hydrophilic polymer moiety comprises polyethylene glycol (PEG) having a 6 to 20 atom chain length.

In various embodiments, the variant peptide is made synthetically.

In various embodiments, the variant peptide is stable for 10 days at about 37° C., pH 7.0 to 7.6. In various embodiments, the variant peptide is stable for at least 10 days at about 37° C., pH 7.0 to 7.4. In various embodiments, the variant peptide is stable for at least 10 days at about 37° C., pH 7.2 to 7.6.

In various embodiments, the variant peptides are stable to deamidation. In various embodiments, the variant peptides are stable to oxidation. In various embodiments, the variant peptides are stable to deamidation, and/or oxidation, or combinations thereof. In various embodiments, methionine is replaced by nor-leucine. In various embodiments, there is little to no detectable deamidation after 10 days.

In various embodiments, the variant peptide has a half-life of about 10 days at about 37° C., pH 7.0 to 7.6. In various embodiments, the variant peptide has a half-life of about 10 days at about 37° C., pH 7.0 to 7.4. In various embodiments, the variant peptide has a half-life of about 10 days at about 37° C., pH 7.2 to 7.6. In various embodiments, the variant peptide has a half-life of at least 10 days at about 37° C., pH 7.0 to 7.6. In various embodiments, the variant peptide has a half-life of at least 10 days at about 37° C., pH 7.0 to 7.4. In various embodiments, the variant peptide has a half-life of at least 10 days at about 37° C., pH 7.2 to 7.6. In various embodiments, the half-life is at least about 15 days, 16 days, 17 days, 18 days, 19 days, 20 days, 21 days, 22 days, 23 days, 24 days, 25 days, 30 days or more.

In various embodiments, the variant peptide has an EC50 from 0.1 to 10 nM in a cGMP assay. In various embodiments, the variant peptide has an EC50 from 0.1 to 25 nM in a cGMP assay.

In various embodiments, greater than 45% of the variant peptide is detected after 10 days in aqueous media at physiological conditions, e.g., about 37° C., pH 7.0 to 7.6. In various embodiments, greater than 50%, 55%, 60%, 65%, 70%, 75%, 80%, 85%, 90% or 95% of the variant peptide is detected after 10 days in aqueous media at physiological conditions, e.g., about 37° C., pH 7.0 to 7.6.

In various embodiments, greater than 45% of the variant peptide is detected after 10 days in aqueous media at 37° C., pH 7.4. In various embodiments, greater than 50%, 55%, 60%, 65%, 70%, 75%, 80%, 85%, 90% or 95% of the variant peptide is detected after 10 days in aqueous media at 37° C., pH 7.4.

In various embodiments, greater than 45% of the variant peptide is detected after 10 days in plasma at physiological conditions, e.g., about 37° C., pH 7.0 to 7.6. In various embodiments, greater than 50%, 55%, 60%, 65%, 70%, 75%, 80%, 85%, 90% or 95% of the variant peptide is detected after 10 days in plasma at physiological conditions, e.g., about 37° C., pH 7.0 to 7.6.

In various embodiments, greater than 45% of the variant peptide is detected after 10 days in plasma at 37° C., pH 7.4. In various embodiments, greater than 50%, 55%, 60%, 65%, 70%, 75%, 80%, 85%, 90% or 95% of the variant peptide is detected after 10 days in plasma at 37° C., pH 7.4.

In various embodiments, the variant peptide is conjugated to a lipid, fatty acid, hydrophilic spacer, or linker, or optionally combinations thereof. In various embodiments, the linker is a hydrophilic polymer moiety. In various embodiments, the hydrophilic polymer moiety is a synthetic hydrophilic polymer moiety.

In various embodiments, the variant peptide has a longer half-life compared to Pro-Gly-CNP37. In various embodiments, the variant peptide has a longer half-life compared to CNP-22. In various embodiments, the variant peptide has a longer half-life compared to Pro-Gly-CNP37 and/or CNP-22. In various embodiments, the variant peptide has a longer half-life compared to Pro-Gly-CNP37 and/or CNP-22 in vitro and/or in vivo.

The disclosure further provides a pharmaceutical composition comprising a CNP variant described herein, and a pharmaceutically acceptable excipient, carrier or diluent.

In various embodiments, the composition is a lyophilized formulation prepared from a formulation that comprises a citric acid/citrate buffer or an acetic acid/acetate buffer having a pH from about 4 to about 6. In various embodiments, the lyophilized formulation is prepared from a formulation that further comprises an isotonicity-adjusting agent or a bulking agent selected from the group consisting of mannitol, sucrose, sorbitol, trehalose, polysorbate 80, and combinations thereof. In various embodiments, the lyophilized formulation is prepared from a formulation that further comprises an antioxidant selected from the group consisting of methionine, ascorbic acid, salt forms of ascorbic acid, thioglycerol, and combinations thereof. In various embodiments, the CNP variant composition is supplied as a lyophilized powder for reconstitution from 0.8 mg to 10 mg. In various embodiments, the CNP variant composition is supplied as a 0.8-mg or 2-mg lyophilized, preservative-free powder for reconstitution.

In various embodiments, the composition is an extended release composition.

In various embodiments, the CNP variant is

```
(Pro-Gly-CNP-37) (BMN111)
                                          (SEQ ID NO: 1)
PGQEHPNARKYKGANKKGLSKGCFGLKLDRIGSMSGLGC.
```

Also provided is a method of treating a bone-related disorder or skeletal dysplasia in a subject in need thereof comprising administering to the subject a composition comprising a CNP variant as described herein.

In various embodiments, the bone-related disorder or skeletal dysplasia is selected from the group consisting of osteoarthritis, hypophosphatemic rickets, achondroplasia, hypochondroplasia, short stature, dwarfism, osteochondrodysplasias, thanatophoric dysplasia, osteogenesis imperfecta, achondrogenesis, chondrodysplasia punctata, homozygous achondroplasia, chondrodysplasia punctata, camptomelic dysplasia, congenital lethal hypophosphatasia, perinatal lethal type of osteogenesis imperfecta, short-rib polydactyly syndromes, hypochondroplasia, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, and spondyloepimetaphyseal dysplasia.

In various embodiments the CNP variants are useful as an adjunct or alternative to growth hormone for treating idiopathic short stature and other skeletal dysplasias.

In various embodiments, the bone-related disorder, skeletal dysplasia or short stature disorder results from an NPR2 mutation, SHOX mutation (Turner's syndrome/Leri Weill), or PTPN11 mutations (Noonan's syndrome).

In various embodiments, the bone-related disorder, skeletal dysplasia or short stature disorder results from an NPR2 mutation, SHOX mutation (Turner's syndrome/Leri Weill), or PTPN11 mutations (Noonan's syndrome), or insulin growth factor 1 receptor (IGF1R).

In various embodiments, the CNP variants are useful to treat growth plate disorders and short stature, including familial short stature, dominant familial short stature which is also known as dominant inherited short stature, or idiopathic short stature. In various embodiments, the short stature or growth plate disorder is a result of a mutation in collagen (COL2A1, COL11A1, COL9A2, COL10), aggrecan (ACAN), indian hedgehog (IHH), PTPN11, NPR2, NPPC, or FGFR3.

In various embodiments, the growth plate disorder or short stature is associated with one or more mutations in a gene associated with a RASopathy.

In various embodiments, the bone-related disorder, skeletal dysplasia or short stature disorder results from a RASopathy. In various embodiments, the RASopathy is Noonan syndrome, Costello syndrome, Cardiofaciocutaneous syndrome, Neurofibromatosis Type 1, or LEOPARD syndrome.

In one embodiment, the RASopathy is hereditary gingival fibromatosis type 1.

In various embodiments, the CNP variants are useful to treat growth plate disorders and short stature, including familial short stature, dominant familial short stature which is also known as dominant inherited short stature, or idiopathic short stature. In various embodiments, the short stature or growth plate disorder is a result of a mutation in collagen (COL2A1, COL11A1, COL9A2, COL10), aggrecan (ACAN), indian hedgehog (IHH), PTPN11, NPR2, NPPC, FGFR3, or insulin growth factor 1 receptor (IGF1R).

In various embodiments, the growth plate disorder or short stature is associated with one or more mutations in a gene associated with a RASopathy.

In various embodiments, the CNP variants are useful to treat a subject with short stature having a height SDS of less than −1.0, −1.5, −2.0, −2.5, or −3.0, and having at least one parent with a height SDS of less than −1.0, −1.5, −2.0 or −2.5, optionally wherein the second parent has height within the normal range. In various embodiments, the CNP variants are useful to treat a subject with short stature having a height SDS of between −2.0 to −3.0. In various embodiments, the CNP variants are useful to treat a subject with short stature having a height SDS of between −2.0 to −2.5. In various embodiments, the short stature is associated with one or more mutations in a gene associated with short stature, such as, collagen (COL2A1, COL11A1, COL9A2, COL10), aggrecan (ACAN), indian hedgehog (IHH), PTPN11, NPR2, NPPC, FGFR3, or insulin growth factor 1 receptor (IGF1R), or combinations thereof. In various embodiments, the growth plate disorder or short stature is associated with one or more mutations in a gene associated with a RASopathy.

In various embodiments, the short stature is a result of mutations in multiple genes as determined by polygenic risk score (PRS). In various embodiments, the subject has a mutation in NPR2 and a low PRS. In various embodiments, the subject has a mutation in FGFR3 and a low PRS. In various embodiments, the subject has a mutation in NPR2 and a low PRS. In various embodiments, the subject has a mutation in IGF1R and a low PRS. In various embodiments, the subject has a mutation in NPPC and a low PRS. In various embodiments, the subject has a mutation in SHOX and a low PRS. In various embodiments, the subject has one or more mutation in one or more of FGFR3, IGF1R, NPPC, NPR2 and SHOX, and a low PRS. In various embodiments, the PRS is 1 or 2. In various embodiments, the PRS is 1. In various embodiments, the PRS is 2. Polygenic risk scores (PRS) were calculated for height as described in Example 4. PRS 1 refers to the lowest height, PRS 5 the tallest height.

In various embodiments, the CNP variant is

```
(Pro-Gly-CNP-37)
                                        (SEQ ID NO: 1)
PGQEHPNARKYKGANKKGLSKGCFGLKLDRIGSMSGLGC.
```

In various embodiments, the peptide further comprises an acetyl group. In various embodiments, the acetyl group is on the N-terminus of the peptide. In various embodiments, the peptide further comprises an OH or an $NH_2$ group at the C-terminus. In various embodiments, the variant comprises one or more linker groups as described herein. In various embodiments, the linker is a hydrolysable linker.

In various embodiments, the disclosure provides a method of elongating a bone or increasing long bone growth in a subject in need thereof, comprising administering to the subject a composition comprising a CNP variant described herein, and wherein the administering elongates a bone or increases long bone growth.

In various embodiments, the composition is administered subcutaneously, intradermally, intraarticularly, orally, or intramuscularly.

In various embodiments, the composition is administered once daily, once weekly, once every two weeks, once every three weeks, once every 4 weeks, once every 6 weeks, once every two months, once every three months or once every six months.

In various embodiments, the composition is an extended release composition.

Further contemplated is a method of treating a CNP-responsive condition or disorder, comprising administering a CNP variant or composition as described herein to a subject, and monitoring the level of at least one bone- or cartilage-associated biomarker in the subject, wherein an increase in the level of the at least one bone- or cartilage-associated biomarker indicates a therapeutic effect of the CNP peptide or variant on the subject or the condition or disorder.

Further contemplated is a method of overcoming cell growth arrest induced by a constitutively active mutant fibroblast growth factor receptor 3 (FGFR-3) comprising contacting a cell expressing the constitutively active FGFR-3 with a CNP variant or a composition as described herein.

Further contemplated is a method of stimulating cGMP production in a cell expressing natriuretic peptide receptor B (NPR-B) comprising contacting the cell expressing NPR-B with a CNP variant or a composition as described herein.

In various embodiments, the method further comprises adjusting the amount or frequency of administration of the CNP peptide or variant as described herein, wherein i) the amount or frequency of administration of the CNP peptide or variant is increased if the level of the at least one bone- or cartilage-associated biomarker is below a target level; or ii) the amount or frequency of administration of the CNP peptide or variant is decreased if the level of the at least one bone- or cartilage-associated biomarker is above a target level.

In various embodiments, the at least one bone- or cartilage-associated biomarker is selected from the group consisting of CNP, cGMP, propeptides of collagen type II and fragments thereof, collagen type II and fragments thereof, Collagen Type I C-Telopeptide (CTx), osteocalcin, proliferating cell nuclear antigen (PCNA), propeptides of type I procollagen (PINP) and fragments thereof, collagen type I and fragments thereof, aggrecan chondroitin sulfate, collagen X, and alkaline phosphatase.

In various embodiments, the CNP variant is

```
(Pro-Gly-CNP-37)
                                          (SEQ ID NO: 1)
PGQEHPNARKYKGANKKGLSKGCFGLKLDRIGSMSGLGC.
```

In various embodiments, the peptide further comprises an acetyl group. In various embodiments, the acetyl group is on the N-terminus of the peptide. In various embodiments, the acetyl group is on an amino acid side chain within the peptide sequence. In various embodiments, the peptide further comprises an OH or an $NH_2$ group at the C-terminus. In various embodiments, the variant comprises one or more linker groups as described herein. In various embodiments, the linker is a hydrolysable linker.

Also provided is a method of making a CNP variant described herein comprising synthesizing the peptide on a solid-phase resin using Fmoc amino acids.

In various embodiments, the method comprises acetylating the peptides by reacting the resin with NMP/$Ac_2O$/DIEA (10:1:0.1, v/v/v).

In various embodiments, the method comprises conjugating the peptide to a conjugate moiety, optionally on a lysine residue. In various embodiments, the method comprises cleaving the protective amino group on lysine, reacting the peptide with 2× Fmoc-amino PEG(2) followed by amino acid, followed by conjugation of the lipid or fatty acid moiety.

BRIEF DESCRIPTION OF THE DRAWINGS

FIG. 1 illustrates use of a peptoid or electronic linker in a CNP conjugate described herein.

FIG. 5 shows the nucleotide and predicted protein sequence of the first exon in NPR2 mutant clones transfected into RCS cells.

FIG. 6 shows exemplary NPR2 mutations analyzed for response to CNP.

FIG. 7 shows exemplary mutations associated with short stature in FGFR3, IGF1R, NPPC, NPR2 and SHOX.

FIG. 8 illustrates the Combined effect of PRS and rare coding variants on Height.

DETAILED DESCRIPTION

Figure 2A:
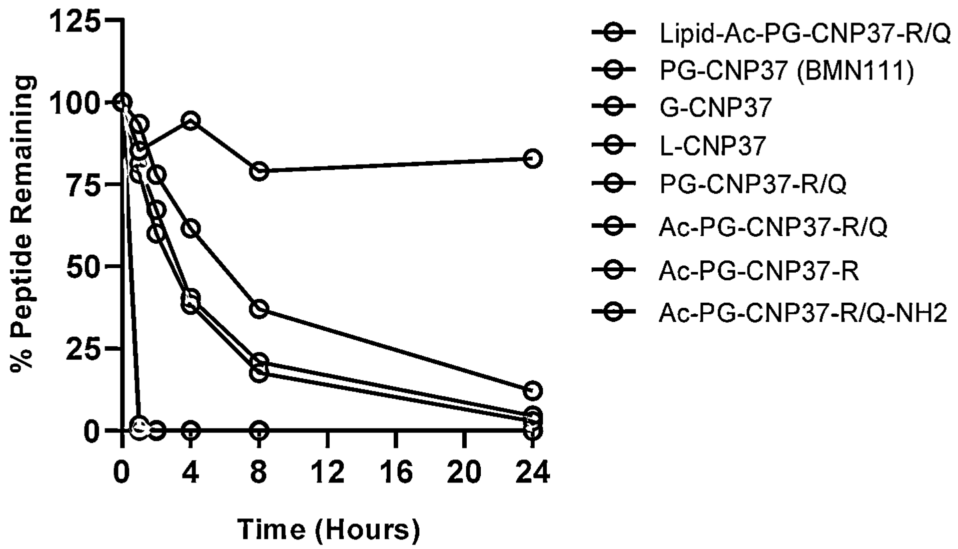
FIG. 2 shows the stability of CNP variants in human plasma over a period of 24 hrs.

The present disclosure relates to stable CNP variants useful in treating skeletal dysplasias and bone growth disorders.

As used in the specification and the appended claims, the indefinite articles "a" and "an" and the definite article "the" include plural as well as singular referents unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range. Whenever the term "about" or "approximately" precedes the first numerical value in a series of two or more numerical values, it is understood that the term "about" or "approximately" applies to each one of the numerical values in that series.

The term "C-type natriuretic peptide" or "CNP" refers to a small, single chain peptide having a 17-amino acid loop structure at the C-terminal end (GenBank Accession No. NP_077720, for the CNP precursor protein, NPPC) and variants thereof. The 17-mer CNP loop structure, is also referred to as CNP 17, the CNP ring, or CNP cyclic domain. CNP includes the active 53-amino acid peptide (CNP-53) and the mature 22-amino acid peptide (CNP-22), and peptides of varying lengths between the two peptides.

In various embodiments, a "CNP variant" is at least about 40%, 50%, 60%, 70%, 75%, 80%, 85%, 90%, or 95% homologous to the wild type NPPC over the same number of amino acid residues. It is further contemplated that a CNP variant peptide may comprise from about 1 to about 53, or 1 to 39, or 1 to 38, or 1 to 37, or 1 to 35, or 1 to 34, or 1 to 31, or 1 to 27, or 1 to 22, or 10 to 35, or about 15 to about 37 residues of the NPPC polypeptide. In one embodiment, a CNP variant may comprise a sequence of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35,36, 37, 38, 39, 40, 41, 42, 43, 44, 45, 46, 47, 48, 49, 50, 51, 52, or 53 amino acids derived from the NPPC polypeptide.

The term "conjugate moiety" refers to a moiety that is conjugated to the variant peptide. Conjugate moieties include a lipid, fatty acid, hydrophilic spacer, synthetic polymer, linker, or optionally, combinations thereof.

The term "effective amount" refers to a dosage sufficient to produce a desired result on a health condition, pathology, or disease of a subject or for a diagnostic purpose. The desired result may comprise a subjective or objective improvement in the recipient of the dosage. "Therapeutically effective amount" refers to that amount of an agent effective to produce the intended beneficial effect on health. An appropriate "effective" amount in any individual case may be determined by one of ordinary skill in the art using routine experimentation. It will be understood that the specific dose level and frequency of dosage for any particular patient may be varied and will depend upon a variety of factors, including the activity of the specific compound employed; the bioavailability, metabolic stability, rate of excretion and length of action of that compound; the mode and time of administration of the compound; the age, body weight, general health, sex, and diet of the patient; and the severity of the particular condition.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. In one embodiment, a substantially pure composition means that the species of interest comprises at least about 70%, 75%, 80%, 85%, 90%, 95%, 98% or more of the macromolecular species present in the composition on a molar or weight basis. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition. In an embodiment, the compounds of the disclosure are substantially pure or isolated. In another embodiment, the compounds of the disclosure are substantially pure or isolated with respect to the macromolecular starting materials used in their production. In yet another embodiment, the pharmaceutical compositions of the disclosure comprise a substantially pure or isolated CNP variant admixed with one or more pharmaceutically acceptable excipients, carriers or diluents, and optionally with another biologically active agent.

"Treatment" refers to prophylactic treatment or therapeutic treatment or diagnostic treatment. In certain embodiments, "treatment" refers to administration of a compound or composition to a subject for therapeutic, prophylactic or diagnostic purposes.

A "prophylactic" treatment is a treatment administered to a subject who does not exhibit signs of a disease or exhibits only early signs of the disease, for the purpose of decreasing the risk of developing pathology. The compounds or compositions of the disclosure may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional or physical, subjective or objective. The compounds of the disclosure may also be given as a therapeutic treatment or for diagnosis.

"Diagnostic" means identifying the presence, extent and/or nature of a pathologic condition. Diagnostic methods differ in their specificity and selectivity. While a particular diagnostic method may not provide a definitive diagnosis of a condition, it suffices if the method provides a positive indication that aids in diagnosis.

"Bone- or cartilage-associated biomarker" or "bone- or cartilage-associated marker" refers to a growth factor, enzyme, protein, or other detectable biological substance or moiety whose level is increased or decreased in association with, e.g., cartilage turnover, cartilage formation, cartilage growth, bone resorption, bone formation, bone growth, or combinations thereof. Such biomarkers may be measured before, during and/or after administration of a CNP variant as described herein. Exemplary bone- or cartilage-associated biomarkers include, but are not limited to, CNP, cGMP, propeptides of collagen type II and fragments thereof, collagen type II and fragments thereof, propeptides of collagen type I and fragments thereof, collagen type I and fragments thereof, osteocalcin, proliferating cell nuclear antigen (PCNA), aggrecan chondroitin sulfate, collagen X, and alkaline phosphatase. Cartilage- and bone-associated biomarkers can be measured in any appropriate biological sample, including but not limited to, tissues, blood, serum, plasma, cerebrospinal fluid, synovial fluid and urine. In some embodiments, the biomarkers are measured in blood, plasma or serum from animals undergoing efficacy/pharmacodynamic in vivo studies and/or from the conditioned media of ex vivo studies.

"Pharmaceutical composition" or "formulation" refers to a composition suitable for pharmaceutical use in subject animal, including humans and mammals. A pharmaceutical composition comprises a therapeutically effective amount of CNP variant, optionally another biologically active agent, and optionally a pharmaceutically acceptable excipient, carrier or diluent. In an embodiment, a pharmaceutical composition encompasses a composition comprising the active ingredient(s), and the inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and a pharmaceutically acceptable excipient, carrier or diluent.

"Pharmaceutically acceptable carrier" refers to any of the standard pharmaceutical carriers, buffers, and the like, such as a phosphate buffered saline solution, 5% aqueous solution of dextrose, and emulsions (e.g., an oil/water or water/oil emulsion). Non-limiting examples of excipients include adjuvants, binders, fillers, diluents, disintegrants, emulsifying agents, wetting agents, lubricants, glidants, sweetening agents, flavoring agents, and coloring agents. Suitable pharmaceutical carriers, excipients and diluents are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration).

A "pharmaceutically acceptable salt" is a salt that can be formulated into a compound for pharmaceutical use, including but not limited to metal salts (e.g., sodium, potassium, magnesium, calcium, etc.) and salts of ammonia or organic amines.

By "pharmaceutically acceptable" or "pharmacologically acceptable" is meant a material that is not biologically or otherwise undesirable, i.e., the material may be administered to an individual without causing any undesirable biological effects or without interacting in a deleterious manner with any of the components of the composition in which it is contained or with any components present on or in the body of the individual.

"Physiological conditions" refer to conditions in the body of an animal (e.g., a human). Physiological conditions include, but are not limited to, body temperature and an aqueous environment of physiologic ionic strength, pH and enzymes. Physiological conditions also encompass conditions in the body of a particular subject which differ from the "normal" conditions present in the majority of subjects, e.g., which differ from the normal human body temperature of approximately 37° C. or differ from the normal human blood pH of approximately 7.4.

By "physiological pH" or a "pH in a physiological range" is meant a pH in the range of approximately 7.0 to 8.0 inclusive, more typically in the range of approximately 7.2 to 7.6 inclusive.

As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, and the like. The term does not denote a particular age or gender. In various embodiments, the subject is human. In various embodiments the subject is a child or adolescent. In various embodiments, the subject is an infant. In various embodiments, the subject is older than 3 , older than 2, older than 1, or older than 6 months in age.

C-type Natriuretic Peptide Variants

C-type natriuretic peptide (CNP) (Biochem. Biophys. Res. Commun., 168: 863-870 (1990) (GenBank Accession No. NP_077720, for the CNP precursor protein, NPPC) (J. Hypertens., 10: 907-912 (1992)) is a small, single chain peptide in a family of peptides (ANP, BNP, CNP) having a 17-amino acid loop structure (Levin et al., N. Engl. J. Med., 339: 863-870 (1998)) and have important roles in multiple biological processes. CNP interacts with natriuretic peptide receptor-B (NPR-B, GC-B) to stimulate the generation of cyclic- guanosine monophosphate (cGMP) (J. Hypertens., 10: 1111-1114 (1992)). CNP is expressed more widely, including in the central nervous system, reproductive tract, bone and endothelium of blood vessels (Hypertension, 49: 419-426 (2007)).

Natural CNP gene and polypeptide have been previously described. U.S. Pat. No. 5,352,770 discloses isolated and purified CNP-22 from porcine brain identical in sequence to human CNP and its use in treating cardiovascular indications. U.S. Pat. No. 6,034,231 discloses the human gene and polypeptide of pre-proCNP (126 amino acids) and the human CNP-53 gene and polypeptide. The mature CNP is a 22-amino acid peptide (CNP-22). Certain CNP variants are disclosed in U.S. Pat. No. 8,198,242, incorporated by reference herein.

In various embodiments, CNP of the disclosure includes truncated CNP ranging from human CNP-17 (hCNP-17) to human CNP-53 (hCNP-53), and having wild-type amino acid sequences derived from hCNP-53. Such truncated CNP peptides include:

```
(CNP-53)
                                        (SEQ ID NO: 56)
DLRVDTKSRAAWARLLQEHPNARKYKGANKKGLSKGCFGLKLDRIGSMS

GLGC;

(CNP-52)
                                        (SEQ ID NO: 15)
LRVDTKSRAAWARLLQEHPNARKYKGANKKGLSKGCFGLKLDRIGSMSG

LGC;

(CNP-51)
                                        (SEQ ID NO: 16)
RVDTKSRAAWARLLQEHPNARKYKGANKKGLSKGCFGLKLDRIGSMSGL

GC;

(CNP-50)
                                        (SEQ ID NO: 17)
VDTKSRAAWARLLQEHPNARKYKGANKKGLSKGCFGLKLDRIGSMSGLG

C;

(CNP-49)
                                        (SEQ ID NO: 18)
DTKSRAAWARLLQEHPNARKYKGANKKGLSKGCFGLKLDRIGSMSGLGC

(CNP-48)
                                        (SEQ ID NO: 19)
TKSRAAWARLLQEHPNARKYKGANKKGLSKGCFGLKLDRIGSMSGLGC;

(CNP-47)
                                        (SEQ ID NO: 20)
KSRAAWARLLQEHPNARKYKGANKKGLSKGCFGLKLDRIGSMSGLGC;

(CNP-46)
                                        (SEQ ID NO: 21)
SRAAWARLLQEHPNARKYKGANKKGLSKGCFGLKLDRIGSMSGLGC;

(CNP-45)
                                        (SEQ ID NO: 22)
RAAWARLLQEHPNARKYKGANKKGLSKGCFGLKLDRIGSMSGLGC;

(CNP-44)
                                        (SEQ ID NO: 23)
AAWARLLQEHPNARKYKGANKKGLSKGCFGLKLDRIGSMSGLGC;

(CNP-43)
                                        (SEQ ID NO: 24)
AWARLLQEHPNARKYKGANKKGLSKGCFGLKLDRIGSMSGLGC;

(CNP-42)
                                        (SEQ ID NO: 25)
WARLLQEHPNARKYKGANKKGLSKGCFGLKLDRIGSMSGLGC;

(CNP-41)
                                        (SEQ ID NO: 26)
ARLLQEHPNARKYKGANKKGLSKGCFGLKLDRIGSMSGLGC;
```

-continued (CNP-40)
(SEQ ID NO: 27)
RLLQEHPNARKYKGANKKGLSKGCFGLKLDRIGSMSGLGC;

(CNP-39)
(SEQ ID NO: 28)
LLQEHPNARKYKGANKKGLSKGCFGLKLDRIGSMSGLGC;

(CNP-38)
(SEQ ID NO: 2)
LQEHPNARKYKGANKKGLSKGCFGLKLDRIGSMSGLGC;

(CNP-37)
(SEQ ID NO: 3)
QEHPNARKYKGANKKGLSKGCFGLKLDRIGSMSGLGC;

(CNP-36)
(SEQ ID NO: 29)
EHPNARKYKGANKKGLSKGCFGLKLDRIGSMSGLGC;

(CNP-35)
(SEQ ID NO: 30)
HPNARKYKGANKKGLSKGCFGLKLDRIGSMSGLGC;

(CNP-34)
(SEQ ID NO: 4)
PNARKYKGANKKGLSKGCFGLKLDRIGSMSGLGC;

(CNP-33)
(SEQ ID NO: 31)
NARKYKGANKKGLSKGCFGLKLDRIGSMSGLGC;

(CNP-32)
(SEQ ID NO: 32)
ARKYKGANKKGLSKGCFGLKLDRIGSMSGLGC;

(CNP-31)
(SEQ ID NO: 33)
RKYKGANKKGLSKGCFGLKLDRIGSMSGLGC;

(CNP-30)
(SEQ ID NO: 34)
KYKGANKKGLSKGCFGLKLDRIGSMSGLGC;

(CNP-29)
(SEQ ID NO: 35)
YKGANKKGLSKGCFGLKLDRIGSMSGLGC;

(CNP-28)
(SEQ ID NO: 36)
KGANKKGLSKGCFGLKLDRIGSMSGLGC;

(CNP-27)
(SEQ ID NO: 37)
GANKKGLSKGCFGLKLDRIGSMSGLGC;

(CNP-26)
(SEQ ID NO: 38)
ANKKGLSKGCFGLKLDRIGSMSGLGC;

(CNP-25)
(SEQ ID NO: 39)
NKKGLSKGCFGLKLDRIGSMSGLGC;

(CNP-24)
(SEQ ID NO: 40)
KKGLSKGCFGLKLDRIGSMSGLGC;

(CNP-23)
(SEQ ID NO: 41)
KGLSKGCFGLKLDRIGSMSGLGC;

(CNP-22)
(SEQ ID NO: 68)
GLSKGCFGLKLDRIGSMSGLGC;

(CNP-21)
(SEQ ID NO: 42)
LSKGCFGLKLDRIGSMSGLGC;

-continued (CNP-20)
(SEQ ID NO: 43)
SKGCFGLKLDRIGSMSGLGC;

(CNP-19)
(SEQ ID NO: 44)
KGCFGLKLDRIGSMSGLGC;

(CNP-18)
(SEQ ID NO: 45)
GCFGLKLDRIGSMSGLGC;
and (CNP-17)
(SEQ ID NO: 67)
CFGLKLDRIGSMSGLGC.

In various embodiments, the CNP variant peptides are modified CNP-37 or CNP-38 peptides, optionally having mutation(s)/substitution(s) at the furin cleavage site (underlined), and/or containing glycine or proline-glycine at the N-terminus. Exemplary CNP-37 variants include but are not limited to:

[CNP-37(M32N); SEQ ID NO: 46]
QEHPNARKYKGANKKGLSKGCFGLKLDRIGSNSGLGC;

(Met-CNP-37; SEQ ID NO: 47)
MQEHPNARKYKGANKKGLSKGCFGLKLDRIGSMSGLGC;

(Pro-CNP-37; SEQ ID NO: 48)
PQEHPNARKYKGANKKGLSKGCFGLKLDRIGSMSGLGC;

[Gly-CNP-37 (M32N); SEQ ID NO: 49]
GQEHPNARKYKGANKKGLSKGCFGLKLDRIGSNSGLGC;

(Pro-Gly-CNP-37; SEQ ID NO: 1)
PGQEHPNARKYKGANKKGLSKGCFGLKLDRIGSMSGLGC;

(Met-Gly-CNP-37; SEQ ID NO: 50)
MGQEHPNARKYKGANKKGLSKGCFGLKLDRIGSMSGLGC;

(Gly-CNP-37: SEQ ID NO: 51)
GQEHPNARKYKGANKKGLSKGCFGLKLDRIGSMSGLGC (SEQ ID NO: 52)
GQEHPNARKYKGANPKGLSKGCFGLKLDRIGSMSGLGC;

(SEQ ID NO: 53)
GQEHPNARKYKGANQKGLSKGCFGLKLDRIGSMSGLGC;

(SEQ ID NO: 54)
GQEHPNARKYKGANQQGLSKGCFGLKLDRIGSMSGLGC;
and (SEQ ID NO: 55)
GQEHPNARKYKGANKPGLSKGCFGLKLDRIGSMSGLGC;

In various embodiments, CNP variants of the disclosure include (SEQ ID NO: 5)
PGQEHPQARRYRGAQRRGLSRGCFGLKLDRIGSMSGLGC;

(SEQ ID NO: 1)
PGQEHPNARKYKGANKKGLSKGCFGLKLDRIGSMSGLGC;

(SEQ ID NO: 6)
PGQEHPNARRYRGANRRGLSRGCFGLKLDRIGSMSGLGC;

(SEQ ID NO: 5)
PGQEHPQARRYRGAQRRGLSRGCFGLKLDRIGSMSGLGC;

(SEQ ID NO: 7)
PGQEHPQARKYKGAQKKGLSKGCFGLKLDRIGSMSGLGC;

-continued (SEQ ID NO: 5)
PGQEHPQARRYRGAQRRGLSRGCFGLK(AEEA-AEEA-γGlu-C18DA)

LDRIGSMSGLGC;
and (SEQ ID NO: 1)
PGQEHPNARKYKGANKKGLSKGCFGLK(AEEA-AEEA-γGlu-C18DA)

LDRIGSMSGLGC.

It is further contemplated that any of the variants described herein having fewer than 53 amino acids, can be extended by addition of amino acids to the N-terminal end of the peptide. For example, if the CNP variant is a 34-, 35-, 36-, 37-, 38- or 39-mer having altered amino acids compared to wt CNP, such a variant can be extended on the N-terminal end with either wild type or modified residues from CNP53, or from other peptides.

In various embodiments, the CNP variant further comprises an acetyl group. In various embodiments, the acetyl group is on the N-terminus, C-terminus or attached to an internal amino acid side group. In various embodiments, the acetyl group is on the N-terminus of the peptide.

In various embodiments, the peptide variant further comprises an OH or an $NH_2$ group at the C-terminus.

In various embodiments the CNP variants are selected from the group consisting of:

(SEQ ID NO: 8)
Ac-PGQEHPQARRYRGAQRRGLSRGCFGLKLDRIGSMSGLGC-OH, (SEQ ID NO: 9)
Ac-PGQEHPNARKYKGANKKGLSKGCFGLKLDRIGSMSGLGC-$NH_2$, (SEQ ID NO: 10)
Ac-PGQEHPNARRYRGANRRGLSRGCFGLKLDRIGSMSGLGC-OH, (SEQ ID NO: 11)
Ac-PGQEHPNARRYRGANRRGLSRGCFGLKLDRIGSMSGLGC-$NH_2$,
and (SEQ ID NO: 12)
Ac-PGQEHPQARRYRGAQRRGLSRGCFGLKLDRIGSMSGLGC-$NH_2$.

In various embodiments, the CNP variants are selected from the group consisting of:

(SEQ ID NO: 8)
PGQEHPQARRYRGAQRRGLSRGCFGLKLDRIGSMSGLGC-OH, (SEQ ID NO: 9)
PGQEHPNARKYKGANKKGLSKGCFGLKLDRIGSMSGLGC-$NH_2$, (SEQ ID NO: 10)
PGQEHPNARRYRGANRRGLSRGCFGLKLDRIGSMSGLGC-OH, (SEQ ID NO: 11)
PGQEHPNARRYRGANRRGLSRGCFGLKLDRIGSMSGLGC-$NH_2$,
and (SEQ ID NO: 12)
PGQEHPQARRYRGAQRRGLSRGCFGLKLDRIGSMSGLGC-$NH_2$ (SEQ ID NO: 7)
PGQEHPQARKYKGAQKKGLSKGCFGLKLDRIGSMSGLGC-OH.

In various embodiments, the CNP variants are selected from the group consisting of:

(SEQ ID NO: 8)
Ac-PGQEHPQARRYRGAQRRGLSRGCFGLKLDRIGSMSGLGC-OH, (SEQ ID NO: 9)
Ac-PGQEHPNARKYKGANKKGLSKGCFGLKLDRIGSMSGLGC-$NH_2$, (SEQ ID NO: 10)
Ac-PGQEHPNARRYRGANRRGLSRGCFGLKLDRIGSMSGLGC-OH, (SEQ ID NO: 11)
Ac-PGQEHPNARRYRGANRRGLSRGCFGLKLDRIGSMSGLGC-$NH_2$, (SEQ ID NO: 12)
Ac-PGQEHPQARRYRGAQRRGLSRGCFGLKLDRIGSMSGLGC-$NH_2$;

(SEQ ID NO: 13)
Ac-PGQEHPQARKYKGAQKKGLSKGCFGLKLDRIGSMSGLGC-$NH_2$;
and (SEQ ID NO: 14)
Ac-PGQEHPQARKYKGAQKKGLSKGCFGLKLDRIGSMSGLGC-OH.

In various embodiments, the CNP variant is selected from the group consisting of Ac-PGQEHPQARRYRGAQRR-GLSRGCFGLK (AEEA-AEEA-γGlu-C18DA)LDRI-GSMSGLGC-OH (SEQ ID NO:8). In various embodiments, the CNP variant is Ac-PGQEHPNARKYKGANKKGL-SKGCFGLK (AEEA-AEEA-γGlu-C18DA)LDRI-GSMSGLGC-OH (SEQ ID NO: 1). In various embodiments, the CNP variant is (SEQ ID NO: 1)
PGQEHPNARKYKGANKKGLSKGCFGLK(AEEA-AEEA-γGlu-C18DA)

LDRIGSMSGLGC-OH.

In additional embodiments, for any of the CNP variants described herein that have asparagine (Asn/N) residue(s) and/or glutamine (Gln/Q) residue(s), whether they have a wild-type sequence or a non-natural amino acid sequence, any Asn residue(s) and/or any Gln residue(s) can independently be substituted with any other natural or unnatural amino acids, including conservative substitutions such as Asn to Gln. Such substitution(s) are designed in part to minimize or avoid any potential deamidation of asparagine and/or glutamine.

In additional embodiments, for any of the CNP variants described herein that have lysine (Lys/K) residue(s), whether they have a wild-type sequence or a non-natural amino acid sequence, any Lys residue(s) can independently be substituted with any other natural or unnatural amino acids, including substitutions such as Lys to Arg. In various embodiments, all lysine residues are independently substituted with any other natural or unnatural amino acids, including substitutions such as Lys to Arg, except the Lys residue in the CNP variant cyclic domain is not substituted with any other natural or unnatural amino acids.

In one embodiment, the CNP variants are cyclized via formation of a disulfide bond between $Cys^6$ and $Cys^{22}$, as designated in the wtCNP22 peptide. $Cys^6$ can be a cysteine analog such as, e.g., homocysteine or penicillamine. In a further embodiment, the CNP variants can be cyclized by a covalent bond formed head-to-tail, side chain-to-side chain, side chain-to-head, or side chain-to-tail. In an embodiment, the covalent bond is formed between an amino acid at or toward the N-terminus and an amino acid at or toward the C-terminus of the peptide (referred to as "terminal" amino acids in this context). In another embodiment, the covalent bond is formed between the side chains of the two terminal amino acids. In yet another embodiment, the covalent bond is formed between the side chain of one terminal amino acid and the terminal group of the other terminal amino acid, or between the terminal groups of the two terminal amino acids.

Head-to-tail cyclization of the terminal amine to the terminal carboxyl group can be carried out using a number of methods, e.g., using p-nitrophenyl ester, 2,4,5-trichlorophenyl ester, pentafluorophenyl ester, the azide method, the mixed anhydride method, HATU, a carbodimide (e.g., DIC, EDC or DCC) with a catalyst such as HOBt, HONSu or HOAt, or on-resin cyclization.

In addition, the cyclic structure can be formed via a bridging group involving the side chains of amino acid residues of the CNP variant and/or the terminal amino acid residues. A bridging group is a chemical moiety that allows cyclization of two portions of the peptide. Non-limiting examples of bridging groups include amides, thioethers, thioesters, disulfides, ureas, carbamates, sulfonamides, and the like. A variety of methods are known in the art for incorporation of units having such bridging groups. For example, a lactam bridge (i.e., a cyclic amide) can be formed between the N-terminal amino group or an amino group on a side chain and the C-terminal carboxylic acid or a carboxyl group on a side chain, e.g., the side chain of lysine or ornithine and the side chain of glutamic acid or aspartic acid. A thioester can be formed between the C-terminal carboxyl group or a carboxyl group on a side chain and the thiol group on the side chain of cysteine or a cysteine analog.

Alternatively, a cross link can be formed by incorporating a lanthionine (thio-dialanine) residue to link alanine residues that are covalently bonded together by a thioether bond. In another method, a cross-linking agent, such as a dicarboxylic acid (e.g., suberic acid (octanedioic acid)), can link the functional groups of amino acid side chains, such as free amino, hydroxyl, and thiol groups.

Enzyme-catalyzed cyclization can also be used. For example, it has been reported that the thioesterase domain of tyrocidine synthetase can be used to cyclize a thioester precursor, a subtilisin mutant can be utilized to cyclize peptide glycolate phenylalanylamide esters, and the antibody ligase 16G3 can be employed to cyclize a p-nitrophenylester. For a review of peptide cyclization, see Davies, J. Peptide Sci., 9: 471-501 (2003), incorporated herein by reference in its entirety.

In certain embodiments, the final product has a purity of at least about 70%, 75%, 80%, 85%, 90%, 95%, 96%, 97%, 98%, or at least about 99%.

Peptide Conjugates

Peptide therapeutics are attractive biological therapeutic agents, but are often disadvantaged by low stability and short half-life in solution (Tang et al., Eur J Pharm Sci. 102:63-70, 2017). Attempts to improve efficacy of peptide therapeutics, by enhancing stability and/or increasing the half-life, include attempts to encapsulate hydrophilic peptides into biodegradable particles such as liposomes or polymer particles. However, this has been difficult due to the cationic nature of these peptides and their ability to electrostatically interact with liposomes of negatively charged polymers (Griesser et al., Int J Pharmaceutics 520:267-274, 2017). Generation of peptide conjugates has been one means used to enable better encapsulation of hydrophilic polymers into microparticles or liposomes (Lu et al., Mol. Pharmaceutics 15:216-225, 2018).

Peptides can be a string of amino acids from 5 to 100 amino acids. The peptide can have positively charged amino acids, negatively charged amino acids, or a mixture of both, such that the peptide is capable of interacting with charged moieties, e.g., a cation, anion or a combination thereof having charged species opposite to those in the peptide.

It is contemplated that the peptide is complexed to a moiety, e.g., a conjugate moiety, that confers increased stability or half-life. In various embodiments, the conjugate moiety is complexed via a non-covalent bond or is attached by a covalent bond. The moiety may be non-covalently attached with the peptide via electrostatic interactions. Alternatively, the moiety may be covalently associated to the peptide via one or more linker moieties. Linkers can be cleavable and non-cleavable linkers. Cleavable linkers may be cleaved via enzymes, nucleophilic/basic reagents, reducing agents, photo-irradiation, electrophilic/acidic reagents, organometallic and metal reagents, or oxidizing reagents. Linkers may also be self-immolative linkers. Exemplary linkers include, but are not limited to, N-succinimidyl-3-(2-pyridyldithiol)propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene), beta alanine, 4-aminobutyric acid (GABA), 2-aminoethoxy acid (AEA), aminoethoxy-2-ethoxy acetic acid (AEEA), 5 aminovaleric acid (AVA), 6-aminocaproic acid (Abx), a vicinal diol cleavable linker, Trimethyl Lock Lactonization, p-alkoxyphenyl carbamate, bicin, peptoid or bicin-type linkers, and electronic linkers as described herein.

In various embodiments, the linker is attached to a residue of the CNP variant within the CNP cyclic domain or at a site other than the CNP cyclic domain. In various embodiments, the linker is attached to a lysine residue. In various embodiments, the linker is attached to a lysine residue in the CNP cyclic domain.

In various embodiments, the CNP variant is attached to the conjugate moiety via the linker. In various embodiments, the linker is attached to the conjugate moiety via the hydrophilic spacer of the conjugate moiety.

In various embodiments, the linker is a hydrolysable linker.

In various embodiments the linker is a peptoid or electronic linker. In various embodiments the linker is a peptoid linker. In various embodiments the linker is an electronic linker. In various embodiments, the linker comprises an $SO_2$ moiety. Exemplary linkers are illustrated in FIG. 1. It is further contemplated that linkers in FIG. 1 are modified by substitution on the R groups. For example, bicin-type linkers include the structures as set out below:

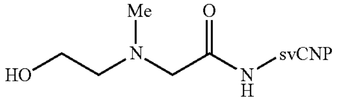

BCC-1

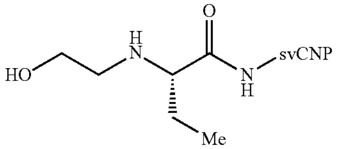

BCC-3

-continued

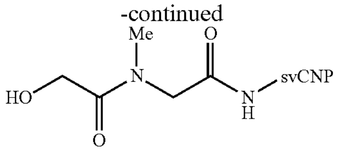

BCC-2

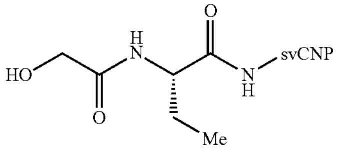

BCC-4

In various embodiments, the moiety conjugated to the peptide is a synthetic polymer such as polyethylene glycol, a linker, a lipid moiety or fatty acid, or a combination thereof. In various embodiments, the CNP variant is conjugated with a fatty acid, an amino acid, a spacer and a linker. In various embodiments, the CNP variant is conjugated with a fatty acid, an amino acid, a polyethylene glycol spacer or a polyethylene glycol derivative spacer, and a linker. In various embodiments, the CNP variant is conjugated with a fatty acid, an amino acid, a spacer, and a linker, wherein the spacer comprises a substituted C-6 to C-20 alkyl chain or any amino acid, or a combination of both, wherein the carbon atoms of the alkyl chain can be replaced by one or more of O, NH, N(C-1 to C-6 alkyl), or carbonyl groups.

In various embodiments, the CNP variant is conjugated with a fatty acid. It is hypothesized that the lipid technology increases the serum half-life of the CNP variant allowing for less frequent injections and/or improved oral delivery. In various embodiments, the fatty acid is a short chain, medium chain, long chain fatty acid, or a dicarboxylic fatty acid. In various embodiments, the fatty acid is saturated or unsaturated. In various embodiments, the fatty acid is a C-6 to C-20 fatty acid. In various embodiments, the fatty acid is a C-6, C-8, C-10, C-12, C-14, C-16, C-18 or C-20 fatty acid. In various embodiments, the fatty acid is decanoic acid, dodecanoic acid, myristic acid, palmitic acid, stearic acid, arachidic acid, or diacids of the same. In various embodiments, the fatty acid is conjugated to a lysine residue.

In various embodiments, it is contemplated that the CNP variants described herein comprise a conjugate moiety as described herein. It is contemplated that the conjugate moiety is on a residue of the CNP cyclic domain or at a site other than the CNP cyclic domain. In various embodiments, the conjugate moiety is on a lysine residue. In various embodiments, the conjugate moiety comprises one or more acid moieties. In various embodiments, the acid moiety is a fatty acid.

In various embodiments, the conjugate moiety comprises an acid moiety linked to a hydrophilic spacer. In various embodiments, the hydrophilic spacer is a substituted C-6 to C-20 alkyl chain or any amino acid, or a combination of both, wherein the carbon atoms of the alkyl chain can be replaced by one or more of O, NH, N(C-1 to C-6 alkyl), or carbonyl groups. In various embodiments, the hydrophilic spacer is any amino acid. In various embodiments, the hydrophilic spacer is gamma glutamic acid (γGlu). In various embodiments, the hydrophilic spacer is a substituted C-6 to C-20 alkyl chain. In various embodiments, the hydrophilic spacer is a substituted C-6, C-8, C-10, C-12, C-14, C-16, C-18 or C-20 alkyl chain. In various embodiments, the hydrophilic spacer is a substituted C-9 to C-18 alkyl chain. In various embodiments, the hydrophilic spacer is a substituted C-18 alkyl chain. In various embodiments, the hydrophilic spacer is a substituted C-9 alkyl chain. In various embodiments, the hydrophilic spacer is one or more OEG (8-amino-3,6-dioxaoctanoic acid) groups. In various embodiments, the hydrophilic spacer is one or two OEG (8-amino-3,6-dioxaoctanoic acid) groups. In various embodiments, the hydrophilic spacer is OEG (8-amino-3,6-dioxaoctanoic acid). In various embodiments, the spacer is OEG (8-amino-3,6-dioxaoctanoic acid) or γGlu. In various embodiments, the hydrophilic spacer is gamma glutamic acid (γGlu) linked to one or more OEG (8-amino-3,6-dioxaoctanoic acid) groups. In various embodiments, the hydrophilic spacer is gamma glutamic acid (γGlu) linked to one or two OEG (8-amino-3,6-dioxaoctanoic acid) groups (diEG). In various embodiments, the acid moiety and the hydrophilic spacer have the structure AEEA-AEEA-γGlu-C18DA.

In various embodiments, the CNP variant has the structure: PGQEHPQARRYRGAQRRGLSRGCFGLK(AEEA-AEEA-γGlu-C18DA)LDRIGSMSGLGC (SEQ ID NO: 5), or Ac-PGQEHPQARRYRGAQRRGLSRGCFGLK(AEEA-AEEA-γGlu-C18DA)LDRIGSMSGLGC-OH (SEQ ID NO: 8). In various embodiments, the CNP variant has the structure PGQEHPNARKYKGANKKGLSKGCFGLK(AEEA-AEEA-γGlu-C18DA)LDRIGSMSGLGC, Ac-PGQEHPNARKYKGANKKGLSKGCFGLK(AEEA-AEEA-γGlu-C18DA)LDRIGSMSGLGC-OH (SEQ ID NO: 1), or PGQEHPNARKYKGANKKGLSKGCFGLK (AEEA-AEEA-γGlu-C18DA)LDRIGSMSGLGC-OH (SEQ ID NO: 1). In various embodiments, the CNP variant comprises Asn to Glu variants of the above peptides.

In various embodiments, the disclosure contemplates use of hydrophilic or water soluble polymers (e.g., oxygenated alkyl chains, wherein the carbon atoms can be replaced with one or more oxygen atoms, such as polyethylene glycol (PEG) or polyethylene oxide (PEO) and the like). In various embodiments, the water soluble polymers can vary in type (e.g., homopolymer or copolymer; random, alternating or block copolymer; linear or branched; monodispersed or polydispersed), linkage (e.g., hydrolysable or stable linkage such as, e.g., amide, imine, aminal, alkylene, or ester bond), conjugation site (e.g., at the N-terminus, internal, and/or C-terminus), and length (e.g., from about 0.2, 0.4 or 0.6 kDa to about 2, 5, 10, 25, 50 or 100 kDa). The hydrophilic or water-soluble polymer can be conjugated to the CNP variant by means of N-hydroxy succinimide (NHS)- or aldehyde-based chemistry or other chemistry, as is known in the art. In various embodiments, negatively charged PEG-CNP variants can be designed for reduced renal clearance, including but not limited to use of carboxylated, sulfated and phosphorylated compounds (Caliceti, Adv. Drug Deliv. Rev., 55: 1261-77 (2003); Perlman, J. Clin. Endo. Metab., 88: 3227-35 (2003); Pitkin, Antimicrob. Ag. Chemo., 29: 440-444 (1986); Vehaskari, Kidney Intl, 22: 127-135 (1982)). In one embodiment, the PEG (or PEO) moiety contains carboxyl group(s), sulfate group(s), and/or phosphate group(s).

In another embodiment, the hydrophilic polymer (e.g., PEG or PEO) moieties conjugated to the N-terminus, C-terminus and/or internal site(s) of CNP variants described herein contain one or more functional groups that are positively charged under physiological conditions. Such moieties are designed, inter alia, to improve distribution of such conjugated CNP variants to cartilage tissues. In one embodiment, PEG moieties contain one or more primary, secondary or tertiary amino groups, quaternary ammonium groups, and/or other amine-containing (e.g., urea) groups.

Methods of Making

Contemplated herein is also a method of making a composition comprising a CNP variant and optionally a conjugate moiety as described herein.

In various embodiments, the CNP variant is made synthetically using standard protein synthesis chemistry. For example, peptides are synthesized step-wise using a solid-phase resin and standard Fmoc chemistry. Peptides are cleaved from the resin using tri-fluroacetic acid (TFA) and purified by reverse phase high-performance liquid chromatography (RP-HPLC).

In various embodiments, the method further comprises, acetylating the peptides by reacting the resin with NMP/$Ac_2O$/DIEA, optionally at 10:1:0.1, v/v/v.

Further provided is a method wherein the peptide is conjugated to a conjugate moiety, optionally on a lysine residue. The step comprising cleaving the protective amino group on the lysine, reacting the peptide with 2× Fmoc-amino PEG(2) followed by amino acid, followed by conjugation of the lipid or fatty acid moiety. In various embodiments, the conjugate moiety comprises one or more lipids or fatty acids and a hydrophobic spacer.

The method further provides a step of cleaving the peptide from the resin by contacting with tri-fluoroacetic acid, and a step of purifying the peptide by reverse phase-HPLC.

In certain embodiments, the CNP variants described herein are produced by a recombinant process that comprises culturing in a medium a host cell comprising a first polynucleotide encoding a CNP variant polypeptide, optionally linked to a second polynucleotide encoding a cleavable peptide or protein under conditions that result in expression of a fusion polypeptide encoded by the polynucleotides. In some embodiments, the host cell is transformed with an expression vector comprising the polynucleotide encoding the CNP variant polypeptide, optionally linked to the polynucleotide encoding the cleavable peptide or protein. In certain embodiments, the fusion polypeptide is expressed as a soluble protein or as an inclusion body. The expressed fusion polypeptide can be isolated from the host cell or culture medium, and the isolated fusion polypeptide can be contacted with a cleaving agent to release the CNP variant.

Methods of making CNP variant peptides, including use of host cells, expression vectors, cleavable peptides, and culture parameters, are disclosed in U.S. Pat. No. 8,198,242, hereby incorporated by reference.

Methods of Use

Achondroplasia is a result of an autosomal dominant mutation in the gene for fibroblast growth factor receptor 3 (FGFR-3), which causes an abnormality of cartilage formation. FGFR-3 normally has a negative regulatory effect on chondrocyte growth, and hence bone growth. In achondroplasia, the mutated form of FGFR-3 is constitutively active, which leads to severely shortened bones. In humans activating mutations of FGFR-3 are the primary cause of genetic dwarfism. Mice having activated FGFR-3 serve as a model of achondroplasia, the most common form of the skeletal dysplasias, and overexpression of CNP rescues these animals from dwarfism. Accordingly, functional variants of CNP are potential therapeutics for treatment of the various skeletal dysplasias By stimulating matrix production, proliferation and differentiation of chondrocytes and increasing long bone growth, the CNP variants of the disclosure are useful for treating mammals, including humans, suffering from a bone-related disorder, such as a skeletal dysplasia. Non-limiting examples of CNP-responsive bone-related disorders and skeletal dysplasias include achondroplasia, hypochondroplasia, short stature, dwarfism, osteochondrodysplasias, thanatophoric dysplasia, osteogenesis congenita, achondrogenesis, chondrodysplasia congenit, homozygous achondroplasia, chondrodysplasia congenit, camptomelic dysplasia, congenital lethal hypophosphatasia, perinatal lethal type of osteogenesis congenita, short-rib polydactyly syndromes, hypochondroplasia, rhizomelic type of chondrodysplasia congenit, Jansen-type metaphyseal dysplasia, spondyloepiphyseal dysplasia congenital, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, and spondyloepimetaphyseal dysplasia. Short stature, growth plate disorder, bone-related disorder or skeletal dysplasias contemplated herein include disorders related to NPR2 mutation, SHOX mutation (Turner's syndrome/Leri Weill), and PTPN11 mutations (Noonan's syndrome).

By stimulating matrix production, proliferation and differentiation of chondrocytes and increasing long bone growth, the CNP variants of the disclosure are useful for treating mammals, including humans, suffering from a bone-related disorder, such as a skeletal dysplasia. Non-limiting examples of CNP-responsive bone-related disorders and skeletal dysplasias include achondroplasia, hypochondroplasia, short stature, dwarfism, osteochondrodysplasias, thanatophoric dysplasia, osteogenesis congenita, achondrogenesis, chondrodysplasia congenit, homozygous achondroplasia, chondrodysplasia congenit, camptomelic dysplasia, congenital lethal hypophosphatasia, perinatal lethal type of osteogenesis congenita, short-rib polydactyly syndromes, hypochondroplasia, rhizomelic type of chondrodysplasia congenit, Jansen-type metaphyseal dysplasia, spondyloepiphyseal dysplasia congenital, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, and spondyloepimetaphyseal dysplasia. Short stature, growth plate disorder, bone-related disorder or skeletal dysplasias contemplated herein include disorders related to NPR2 mutation, SHOX mutation (Turner's syndrome/Leri Weill), PTPN11 mutations (Noonan's syndrome) and IGF1R mutation.

Additional short stature and growth plate disorders contemplated by the methods include disorders related to mutations in collagen (COL2A1, COL11A1, COL9A2, COL10), aggrecan (ACAN), indian hedgehog (IHH), PTPN11, NPR2, NPPC, or FGFR3.

Additional short stature and growth plate disorders contemplated by the methods include disorders related to mutations in collagen (COL2A1, COL11A1, COL9A2, COL10), aggrecan (ACAN), indian hedgehog (IHH), PTPN11, NPR2, NPPC, FGFR3, or IGF1R.

Further, the CNP variants are useful as an adjunct or alternative to growth hormone for treating idiopathic short stature and other skeletal dysplasias.

Growth plate disorders include disorders that result in short stature or abnormal bone growth and that may be the result of a genetic mutation in a gene involved in bone growth, including collagen (COL2A1, COL11A1, COL9A2, COL10), aggrecan (ACAN), indian hedgehog (IHH), PTPN11, NPR2, NPPC, or FGFR3. In various embodiments, growth plate disorders include disorders that result in short stature or abnormal bone growth and that may be the result of a genetic mutation in a gene involved in bone growth, including collagen (COL2A1, COL11A1, COL9A2, COL10), aggrecan (ACAN), indian hedgehog (IHH), PTPN11, NPR2, NPPC, FGFR3, or IGF1R. In various embodiments, the growth plate disorder or short stature is associated with one or more mutations in a gene associated with a RASopathy. In various embodiments, a subject with a growth plate disorder is heterozygous for a mutation in a growth plate gene. In various embodiments, the mutation is a loss-of-function mutation. In various embodiments, the mutation is a gain-of-function mutation. Growth plate disorders include, but are not limited to, familial short stature, dominant familial short stature which is also known as dominant inherited short stature, or idiopathic short stature. See, e.g., Plachy et al., J Clin Endocrinol Metab 104: 4273-4281, 2019.

Mutations in ACAN can give rise to familial osteochondritis dissecans and short stature and eventually osteoarthritis, characterized by areas of bone damage (or lesions) caused by the detachment of cartilage and sometimes bone from the end of the bone at a joint. It has been suggested that the disorganized cartilage network in growing bones impairs their growth, leading to short stature. A mutation associated with ACAN and short stature includes Val2303Met. See Stattin et al., Am J Hum Genet 86(2):126-37, 2010. It is contemplated that patients with a mutation in ACAN resulting in short stature would benefit from treatment with CNP as administration may be able to increase height in these patients by the known interaction of CNP with FGFR3.

The natriuretic peptide system, including receptor NPR2, has been shown to be involved in regulation of endochondral bone growth (Vasques et al., Horm Res Pediat 82:222-229, 2014). Studies have shown that homozygous or compound heterozygous loss-of-function mutations in NPR2 cause acromesomelic dysplasia type Maroteaux (AMDM), which is a skeletal dysplasia having extremely short stature (Vasquez et al., 2014, supra). There are reports implicating heterozygous loss-of-function (such as dominant negative) NPR2 mutations as a cause of short stature, whereas gain-of-function NPR2 heterozygous mutations have been found to be responsible for tall stature (Vasquez et al., 2014, supra). In view of CNP's interaction with NPR2 to stimulate cGMP generation, increasing cGMP levels is desirable in these conditions and would have therapeutic benefit in the management of the complications from these diseases and conditions.

Heterozygous mutations of NPR2 are believed to result in idiopathic short stature and other forms of short stature. Mutations in the NPR2 gene are set out below and described in Amano et al., J Clin Endocrinol Metab 99:E713-718, 2014, Hisado-Oliva et al., J Clin Endocrinol Metab 100: E1133-1142, 2015 and Vasques et al., J Clin Endocrinol Metab 98:E1636-1644, 2013, hereby incorporated by reference. It is contemplated that a subject having short stature to be treated with a CNP variant as described herein has a height SDS of less than −1.0, −1.5, −2.0, −2.5, or −3.0, and has at least one parent with a height SDS of less than −1.0, −1.5, −2.0 or −2.5, optionally wherein the second parent has height within the normal range. In various embodiments, the CNP variants are useful to treat a subject with short stature having a height SDS of between −2.0 to −3.0. In various embodiments, the CNP variants are useful to treat a subject with short stature having a height SDS of between −2.0 to −2.5. However, because de novo mutations in NPR2 can result in short stature as defined by a height SDS of less than −1.5, −2.0, −2.5, or −3.0, treatment of individuals who are heterozygous carriers of a deleterious mutation in NPR2 with neither parent having short stature is also contemplated. Further contemplated is treatment of individuals who are heterozygous for deleterious mutations in other growth plate genes with CNP to improve stature and/or enhance bone growth.

Exemplary NPR2 mutations in patients that may be treated with a CNP variant include:

| Disease | Nucleotide | Mutation | Amino acid change |
|---|---|---|---|
| Short stature | 1669C>T | missense | Arg557Cys |
| Short stature | 2794C>T | missense | Arg932Cys |
| Short stature | 2905G>C | missense | Val969Leu |
| Short stature | 3058C>T | missense | Arg1020Trp |
| Short stature | 2972A>G | missense | Glu991Gly |
| Short stature | 1262C>T | missense | Thr421Met |
| Short stature | 766G>T | missense | Asp256Tyr |
| Short stature | 1982C>A | missense | Thr661Lys |
| Short stature | 2449G>A | missense | Glu817Lys |
| Short stature | 1517G>A | missense | Arg506His |
| Short stature | 1802G>C | missense | Arg601Pro |
| Short stature | 1481T>G | missense | Ile494Ser |
| Short stature | 142G>T | missense | Ala48Ser |
| Short stature | 1167G>T | missense | Glu389Asp |
| Short stature | 1249C>G | missense | Gln417Glu |
| Short stature | 328C>T | missense | Arg110Cys |
| Short stature | 2455C>T | missense | Arg819Cys |
| Short stature | 788G>C | missense | Arg263Pro |
| Short stature | 226T>C | missense | Ser76Pro |
| Short stature | 2710A>T | nonsense | Lys904Term |
| 9:35809194:C:G | | | Leu1009Val |
| 9:35802761:G:C | | | Leu615Phe |
| 9:35799645:C:T | | | Pro301Ser |
| 9:35792928:C:T | | | Arg174Cys |
| 9:35801728:C:G | | | His508Asp |
| 9:35792713:T:C | | | Val102Ala |
| 9:35793980:T:A | | | Tyr250Ter |
| 9:35807085:C:T | | | Thr861Ile |
| 9:35793906:A:G | | | Ile226Val |
| 9:35808558:G:A | | | Arg921Gln |
| 9:35802741:G:A | | | Glu609Lys |
| 9:35802594:G:A | | | Arg601His |
| 9:35808663:T:A | | | Leu956Gln |
| 9:35808545:G:C | | | Gly917Arg |

NPPC's role in skeletal growth is well documented (Hisado-Oliva et al., Genetics Medicine 20:91-97, 2018). The NPPC knock out mouse showed severe disproportionate form of dwarfism including shortening of limbs and endochondral ossification (Hisado-Oliva et al., 2018, supra). Human genome wide studies have shown a link between NPPC and height (Hisado-Oliva et al., 2018, supra). Although CNP haploinsufficiency has been believed to be a cause of short stature in humans, a recent study identified heterozygous mutations in families with short stature and hands (Hisado-Oliva et al., 2018, supra). These studies observed significant reduction in cGMP production as measured in heterozygous state (Hisado-Oliva et al., 2018, supra). Mutations in NPPC include a 355G>T missense mutation causing a Gly119Cys change and a 349C>G missense mutation causing a Arg117Gly change. A CNP variant rescuing CGMP production may provide therapeutic benefit in the management of a disorder in patients having heterozygous loss-of-function NPPC mutations.

Leri-Weill dyschondrosteosis (LWD) is a rare genetic disorder characterized by shortening of the forearms and lower legs, abnormal misalignment of the wrist (Madelung deformity of the wrist), and associated short stature. LWD is caused by a heterozygous mutation in the short stature homeobox-containing (SHOX) gene or its regulatory elements located on the pseudoautosomal region 1 (PAR1) of the sex chromosomes. (See the Rare Disease Database and Carmona et al., Hum Mol Genet 20:1547-1559, 2011). The disorder Langer mesomelic dysplasia arises when there are two SHOX mutations, and may result from a mutation on each chromosome, either a homozygous or compound heterozygous mutations. A subset of SHOX mutations give rise to idiopathic short stature. Turner syndrome results due to a deletion on the X chromosome that can include the SHOX gene. SHOX has been identified as involved in the regulation of FGFR3 transcription and contributes to control of bone growth (Marchini et al., Endocr Rev. 37: 417-448, 2016). SHOX deficiency leads to increased FGFR3 signaling, and there is some evidence to support that SHOX has direct interactions with CNP/NPR2 as well (Marchini, supra). Given the association of SHOX with FGFR3 and bone growth, it is contemplated that a subject having a homozygous or heterozygous SHOX mutation would benefit from treatment with CNP variants as described herein.

RASopathies are a group of rare genetic conditions caused by mutations in genes of the Ras/mitogen-activated protein kinase (MAPK) pathway. RASopathies are a group of disorders characterized by increased signaling through RAS/MAPK pathway. This pathway leads to downstream activation of the RAF/MEK/ERK pathway. Short stature is a characteristic feature of certain RASopathies. For example, CNP signaling inhibits RAF and leads to decreased MEK and ERK activation.

Treatment of RASopathies are contemplated herein. RASopathies associated with short stature include Noonan syndrome, Costello syndrome, Cardiofaciocutaneous syndrome, Neurofibromatosis Type 1, and LEOPARD syndrome. Hereditary gingival fibromatosis type 1 is also a RASopathy contemplated herein. RASopathy patients (including Noonan syndrome, Costello syndrome, Cardiofaciocutaneous syndrome, Neurofibromatosis Type 1, LEOPARD syndrome, hereditary gingival fibromatosis type 1) include patients with heterozygous variants in one or more of the following genes: BRAF, CBL, HRAS, KRAS, LZTR1, MAP2K1, MAP2K2, MRAS, NF1, NRAS, PPP1CB, PTPN11, RAF1, RRAS, RIT1, SHOC2, SOS1, or SOS2 (Tajan et al. Endocr. Rev. 2018;39(5):676-700).

CFC is caused by mutations in several genes in the Ras/MAPK signaling pathway, including K-Ras, B-Raf, Mek1 and Mek2. Costello syndrome, also called faciocutaneoskeletal (FCS) syndrome is caused by activating mutations in the H-Ras gene. Hereditary gingival fibromatosis type I (HGF) is caused by dominant mutations in the SOS1 gene (Son of Sevenless homolog 1), which encodes a guanine nucleotide exchange factor (SOS) that acts on the Ras subfamily of small GTPases. Neurofibromatosis type I (NF1) is caused by mutations in the neurofibromin 1 gene, which encodes a negative regulator of the Ras/MAPK signaling pathway. Noonan syndrome (NS) is caused by mutations in one of several genes, including PTPN11, which encodes SHP2, and SOS1, as well as K-Ras and Raf-1.

CNP has been demonstrated to be an effective therapy in RASopathy models. Ono et al. generated mice deficient in Nf1 in type II collagen producing cells (Ono et al., Hum. Mol. Genet. 2013;22(15):3048-62). These mice demonstrated constitutive ERK1/2 activation, and decreased chondrocyte proliferation, and maturation. Daily injections of CNP in these mice led to decreased ERK phosphorylation and corrected the short stature. A mouse model of Cardiofaciocutaneous syndrome using a Braf mutation (p.Q241R) (Inoue et al. Hum. Mol. Genet. 2019; 28(1):74-83). exhibited decreased body length and reduced growth plate width with smaller proliferative and hypertrophic zones compared to wild type, and CNP administration led to increases in body length in these animals.

Mutations in multiple genes can cause Noonan syndrome, which is characterized by short stature, heart defects, bleeding problems, and skeletal malformations. Mutations in the PTPN11 gene cause about half of all cases of Noonan's syndrome. SOS1 gene mutations cause an additional 10 to 15 percent, and RAF1 and RIT1 genes each account for about 5 percent of cases. Mutations in other genes each account for a small number of cases. The cause of Noonan syndrome in 15 to 20 percent of people with this disorder is unknown.

The PTPN11, SOS1, RAF1, and RIT1 genes all encode for proteins that are important in the RAS/MAPK cell signaling pathway, which is needed for cell division and growth (proliferation), differentiation, and cell migration. Many of the mutations in the genes associated with Noonan syndrome cause the resulting protein to be turned on (active) and this prolonged activation alters normal RAS/MAPK signaling, which disrupts the regulation of cell growth and division, leading to the characteristic features of Noonan syndrome. See, e.g., Chen et al., Proc Natl Acad Sci U S A. 111(31):11473-8, 2014, Romano et al., Pediatrics. 126(4): 746-59, 2010, and Milosavljević et al., Am J Med Genet 170(7):1874-80, 2016. It is contemplated that a subject having mutations that activate the MAPK pathway would benefit from treatment with CNP variants as described herein to improve bone growth and short stature. It is also contemplated that a subject having mutations that activate the MAPK pathway would benefit from treatment with CNP variants as described herein to improve other comorbidities associated with an overactive MAPK pathway in other cells throughout the body where the NPR2 receptor is expressed on its surface.

Mutations in the PTPN11 gene, which encodes the non-receptor protein tyrosine phosphatase SHP-2, lead to disorders characterized by short stature such as Noonan's Syndrome (Musente et al., Eur J Hum Genet 11:201-206 (2003). Musente (supra) identifies numerous mutations in the PTPN11 gene that lead to short stature. Gain of function mutations lead to overactive signaling through SHP2 and inhibit Growth Hormone-induced IGF-1 release, thereby contributing to a decrease in bone growth (Rocca Serra-Nédélec, PNAS 109:4257-4262, 2012). It is contemplated that a subject having a homozygous or heterozygous PTPN11 mutation would benefit from treatment with CNP variants as described herein to improve bone growth and short stature.

Mutations in the Indian hedgehog (IHH) gene, which is related to regulation of endochondral ossification, have also been associated with short stature syndromes (Vasques et al., J Clin Endocrinol Metab. 103:604-614, 2018). Many IHH mutations identified segregate with short stature in a dominant inheritance pattern. Given the association of IHH with bone growth and ossification, it is contemplated that subjects having a homozygous or heterozygous IHH mutation will benefit from treatment with a CNP variant as described herein.

Mutations in FGFR3, including N540K and K650N, lead to short stature and hypochondroplasia.

Insulin-like growth factor 1 receptor (IGF1R) is a hetero-tetrameric ($\alpha 2\beta 2$) transmembrane glycoprotein with an intrinsic kinase activity. IGF1R has been shown to have a role in prenatal and postnatal growth. Heterozygous mutations in IGF1R have been identified in Small for gestational age children (SGA) and individuals with familial short stature (Kawashima et al., Endocrine J. 59:179-185, 2012). Mutations in IGF1R associated with short stature include R108Q/K115N, R59T, R709Q, G1050K, R481Q, V599E, and G1125A (Kawashima, supra).

Height is a highly heritable trait that can be influenced by the combined effect of hundreds or thousands genes (Wood et al, 2014, Nature Genetics, 46:1173-1189. Short stature in an individual can be the result of the combined effect of these genes, without a single gene being the primary contributor. It is contemplated that such individuals with short stature defined by a height SDS of less than −1.0, −1.5, −2.0, −2.5, or −3.0, can be beneficially treated with a CNP variant given the ability of CNP to increase the length of normal animals, for example, enhance bone growth and length of bones.

In various embodiments, the CNP variants are useful to treat a subject with short stature having a height SDS of less than −1.0, −1.5, −2.0, −2.5, or −3.0, and having at least one parent with a height SDS of less than −1.0, −1.5, −2.0 or −2.5, optionally wherein the second parent has height within the normal range. In various embodiments, the CNP variants are useful to treat a subject with short stature having a height SDS of between −2.0 to −3.0. In various embodiments, the CNP variants are useful to treat a subject with short stature having a height SDS of between −2.0 to −2.5. In various embodiments, the short stature is associated with one or more mutations in a gene associated with short stature, such as, collagen (COL2A1, COL11A1, COL9A2, COL10), aggrecan (ACAN), indian hedgehog (IHH), PTPN11, NPR2, NPPC, FGFR3, or insulin growth factor 1 receptor (IGF1R), or combinations thereof.

In various embodiments, the growth plate disorder or short stature is associated with one or more mutations in a gene associated with a RASopathy.

In various embodiments, the short stature is a result of mutations in multiple genes as determined by polygenic risk score (PRS). Polygenic risk scores (PRS) were calculated for height using the largest published GWAS meta-analysis for height that did not include any samples from the UK Biobank project as described in Example 4. The cohort was divided into five PRS quintiles (PRS 1 being the lowest height, PRS 5 the tallest height). In various embodiments, the subject has a mutation in NPR2 and a low PRS. In various embodiments, the subject has a mutation in FGFR3 and a low PRS. In various embodiments, the subject has a mutation in NPR2 and a low PRS. In various embodiments, the subject has a mutation in IGF1R and a low PRS. In various embodiments, the subject has a mutation in NPPC and a low PRS. In various embodiments, the subject has a mutation in SHOX and a low PRS. In various embodiments, the subject has one or more mutation in one or more of FGFR3, IGF1R, NPPC, NPR2 and SHOX, and a low PRS. In various embodiments, the PRS is 1 or 2. In various embodiments, the PRS is 1. In various embodiments, the PRS is 2.

In addition, the CNP variants are useful for treating other bone-related conditions and disorders, such as rickets, hypophosphatemic rickets [including X-linked hypophosphatemic rickets (also called vitamin D-resistant rickets) and autosomal dominant hypophosphatemic rickets], and osteomalacia [including tumor-induced osteomalacia (also called oncogenic osteomalacia or oncogenic hypophosphatemic osteomalacia)].

The CNP variants of the disclosure can also be used to treat osteoarthritis. Osteoarthritis is a degenerative disease of the articular cartilage and occurs frequently in the elderly. Osteoarthritis involves destruction of the cartilage and proliferative change in the bone and cartilage resulting from degeneration of articular components, with the change resulting in a secondary arthritis (e.g., synovitis). The extracellular matrix proteins, which are the functional entity of the cartilage, are reduced, and the number of chondrocytes decreases in osteoarthritis (Arth. Rheum. 46(8): 1986-1996 (2002)). By promoting the matrix production, growth and differentiation of chondrocytes, the CNP compositions are useful for countering the undesired effects of FGF-2 and increasing matrix synthesis in subjects suffering from arthritis, including osteoarthritis, thereby treating arthritis, including osteoarthritis.

In certain embodiments, the CNP variants and compositions and formulations comprising the same of the present disclosure are useful for improving one or more of the symptom(s) or physiological consequences of a skeletal dysplasia, wherein the improvement may be increased absolute growth, increased growth velocity, increased qualitative computed tomography (QCT) bone mineral density, improvement in growth plate morphology, increased long bone growth, improvement in spinal morphology, improved elbow joint range of motion and/or decreased sleep apnea. In this regard, it is noted that the terms “improved”, “improvement”, “increase”, “decrease” and grammatical equivalents thereof are all relative terms that when used in relation to a symptom or physiological consequence of a disease state, refer to the state of the symptom or physiological consequence of the disease after treatment with a CNP variant (or composition or formulation comprising the same) of the present invention as compared to the same symptom or physiological consequence of the disease before treatment with a CNP variant (or composition or formulation comprising the same) of the present invention (i.e., as compared to “baseline”). As described above, a “baseline” state can be determined either through measurement of the state in the subject prior to treatment (which can subsequently be compared to the state in the same subject after treatment), or through measurement of that state in a population of subjects suffering from the same affliction that share the same or similar characteristics (e.g., age, sex and/or disease state or progression).

Also provided is a method of overcoming cell growth arrest induced by a constitutively active mutant fibroblast growth factor receptor 3 (FGFR-3) comprising contacting a cell expressing the constitutively active FGFR-3 with a CNP variant or a composition as described herein.

Further provided is a method of stimulating cGMP production in a cell expressing natriuretic peptide receptor B (NPR-B) comprising contacting the cell expressing NPR-B with a CNP variant or a composition as described herein.

In yet another embodiment, the disclosure provides CNP variants that in vitro or in vivo stimulate the production of at least about 50%, 60%, 70%, 80%, 90%, 100%, 110%, 120%, 130%, 140% or 150% of the cGMP level produced under the same concentration of wtCNP22 (e.g., 1 uM). In a still further embodiment, the CNP variants of the disclosure in vitro or in vivo stimulate the production of at least about 50%, 60%, 70%, 80%, 90%, 100%, 110%, 120%, 130%, 140% or 150% of the cGMP level produced under the same concentration of wtCNP22 (e.g., 1 uM).

It is contemplated that any of the CNP variants described herein are useful in the methods.

In various embodiments, the CNP variant is

```
(Pro-Gly-CNP-37)
                                        (SEQ ID NO: 1)
PGQEHPNARKYKGANKKGLSKGCFGLKLDRIGSMSGLGC.
```

In various embodiments, the peptide further comprises an acetyl group. In various embodiments, the acetyl group is on the N-terminus of the peptide. In various embodiments, the peptide further comprises an OH or an $NH_2$ group at the C-terminus. In various embodiments, the variant comprises one or more linker groups as described herein. In various embodiments, the linker is a hydrolysable linker.

Efficacy of treatment is measured by various parameters. In various embodiments, efficacy is assessed as the change in annualized growth velocity from the baseline period to the intervention period. Efficacy will also be assessed as the change in height SDS from baseline to end of treatment as measured using the CDC growth curves, and growth velocity SDS will be based on the Bone Mineral Density in Childhood Study (Kelly et al., *J. Clin. Endocrinol. Metab.* 2014; 99(6):2104-2112).

QoLISSY, the Quality of Life in Short Stature Youth, is assessed as directed (Quality of Life in Short Stature Youth—The QoLISSY Questionnaire User's Manual. Lengerich: Pabst Science Publishers; 2013).

Pharmaceutical Compositions

The disclosure provides pharmaceutical compositions, including modified release compositions, comprising a CNP variant described herein, and one or more pharmaceutically acceptable excipients, carriers and/or diluents. In certain embodiments, the compositions further comprise one or more other biologically active agents (e.g., inhibitors of proteases, receptor tyrosine kinases, and/or the clearance receptor NPR-C).

The disclosure provides for modified release compositions comprising a conjugate moiety as described herein. Modified-release compositions include those that deliver a drug with a delay after its administration (delayed-release dosage) or for a prolonged period of time (extended-release dosage). Various embodiments of a CNP peptide conjugate provided herein include modified-release compositions, such as extended release, sustained or controlled release, and delayed release. The term "extended release composition" refers to a composition formulated in a manner in order to make the active ingredient/drug available over an extended period of time following administration (US Pharmacopeia). Extended-release dosage include sustained-release (SR) or controlled-release (CR) forms in which. Sustained release maintains drug release over a sustained period but not necessarily at a constant rate, while CR maintains drug release over a sustained period at a nearly constant rate (Pharmaceutics: Drug Delivery and Targeting, Yvonne Perrie, Thomas Rades, Pharmaceutical Press, 2009). Delayed-release compositions or products are modified to delay release of the drug substance for some period of time after initial administration.

In various embodiments, the modified release composition is an extended release composition.

In various embodiments, for the extended release composition, (i) less than about 20% of peptide is released by day 1; and (ii) about 90% of peptide is released weekly, or about 90% of peptide is released bi-weekly, or about 90% of peptide is released monthly, at pH 7 to 7.6.

In various embodiments, less than about 20% of peptide is released by day 1 at pH 7 to 7.6. In various embodiments, less than about 10% of peptide is released by day 1 at pH 7 to 7.6. It is further contemplated that (i) less than about 30%, or about 40%, or about 50% of peptide is released by day 1, at pH 7.0 to 7.6; and (ii) about 90% of peptide is released weekly, or about 90% of peptide is released bi-weekly, or about 90% of peptide is released monthly, at pH 7 to 7.6. It is further contemplated that (i) less than about 30%, or about 40%, or about 50%, or about 60% of peptide is released by day 1, at pH 7.0 to 7.6; and (ii) about 70%, about 80%, or about 90% of peptide is released weekly; or about 70%, about 80%, or about 90% of peptide is released bi-weekly; or about 70%, about 80%, or about 90% of peptide is released every three weeks; or about 70%, about 80%, or about 90% of peptide is released monthly, at pH 7 to 7.6. In various embodiments, about 90% of peptide is released weekly, at pH 7 to 7.6. In various embodiments, about 90% of peptide is released biweekly, at pH 7 to 7.6. In various embodiments, about 90% of peptide is released monthly at pH 7 to 7.6. It is further contemplated that the release can be at a pH between pH 7.0 to 7.6, between pH 7.1 to 7.5, between pH 7.2 to 7.4, between pH 7.2 to 7.6, or between pH 7.0 to 7.4.

In various embodiments, (i) less than about 25%, about 30%, about 35%, about 40%, about 45%, about 50%, about 55%, about 60%, about 65%, about 70%, or about 75% of peptide is released by day 1, at pH 7.0 to 7.6; and (ii) about 90% of peptide is released weekly, or about 90% of peptide is released bi-weekly, or about 90% of peptide is released monthly, at pH 7 to 7.6. It is further contemplated that (i) less than about 25%, about 30%, about 35%, about 40%, about 45%, about 50%, about 55%, about 60% about 65%, about 70%, or about 75% of peptide is released by day 1, at pH 7.0 to 7.6; and (ii) about 70%, about 80%, or about 90% of peptide is released weekly; or about 70%, about 80%, or about 90% of peptide is released bi-weekly; or about 70%, about 80%, or about 90% of peptide is released every three weeks; or about 70%, about 80%, or about 90% of peptide is released monthly, at pH 7 to 7.6; or alternatively ii) about 70%, about 75%, about 80%, about 85%, or about 90% of peptide is released weekly; or about 70%, about 75%, about 80%, about 85%, or about 90% of peptide is released bi-weekly; or about 70%, about 75%, about 80%, about 85%, or about 90% of peptide is released every three weeks; or about 70%, about 75%, about 80%, about 85%, or about 90% of peptide is released monthly, at pH 7 to 7.6

In various embodiments, the composition comprises an excipient, diluent or carrier. In various embodiments, the extended release composition comprises an excipient, diluent or carrier. In various embodiments, the excipient, diluent or carrier is a pharmaceutically acceptable excipient, diluent or carrier.

Non-limiting examples of excipients, carriers and diluents include vehicles, liquids, buffers, isotonicity agents, additives, stabilizers, preservatives, solubilizers, surfactants, emulsifiers, wetting agents, adjuvants, and so on. The compositions can contain liquids (e.g., water, ethanol); diluents of various buffer content (e.g., Tris-HCl, phosphate, acetate buffers, citrate buffers), pH and ionic strength; detergents and solubilizing agents (e.g., Polysorbate 20, Polysorbate 80); anti-oxidants (e.g., methionine, ascorbic acid, sodium metabisulfite); preservatives (e.g., Thimerosol, benzyl alcohol, m-cresol); and bulking substances (e.g., lactose, mannitol, sucrose). The use of excipients, diluents and carriers in the formulation of pharmaceutical compositions is known in the art; see, e.g., Remington's Pharmaceutical Sciences, $18^{th}$ Edition, pages 1435-1712, Mack Publishing Co. (Easton, Pennsylvania (1990)), which is incorporated herein by reference in its entirety.

For example, carriers include without limitation diluents, vehicles and adjuvants, as well as implant carriers, and inert, non-toxic solid or liquid fillers and encapsulating materials that do not react with the active ingredient(s). Non-limiting examples of carriers include phosphate buffered saline, physiological saline, water, and emulsions (e.g., oil/water emulsions). A carrier can be a solvent or dispersing medium containing, e.g., ethanol, a polyol (e.g., glycerol, propylene glycol, liquid polyethylene glycol, and the like), a vegetable oil, and mixtures thereof.

In some embodiments, the compositions are liquid formulations. In certain embodiments, the formulations comprise a CNP variant in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 0.5 to 5 mg/ml, or from about 0.5 to 3 mg/ml, or from about 1 mg/ml to about 10 mg/ml. In various embodiments, the CNP variant is in a concentration of 0.8 mg/mL to 2 mg/mL. In various embodiments, the CNP variant is at a concentration of 0.8 mg/mL. In various embodiments, the CNP variant is at a concentration of 2.0 mg/mL. In various embodiments, the CNP variant is reconstituted from a lyophilized powder.

In further embodiments, the compositions comprise a buffer solution or buffering agent to maintain the pH of a CNP-containing solution or suspension within a desired range. Non-limiting examples of buffer solutions include phosphate buffered saline, Tris buffered saline, and Hank's buffered saline. Buffering agents include without limitation sodium acetate, sodium phosphate, and sodium citrate. Mixtures of buffering agents can also be used. In certain embodiments, the buffering agent is acetic acid/acetate or citric acid/citrate. The amount of buffering agent suitable in a composition depends in part on the particular buffer used and the desired pH of the solution or suspension. In some embodiments, the buffering agent has a concentration of about 10 mM ±5 mM. In certain embodiments, the pH of a composition is from about pH 3 to about pH 9, or from about pH 3 to about pH 7.5, or from about pH 3.5 to about pH 7, or from about pH 3.5 to about pH 6.5, or from about pH 4 to about pH 6, or from about pH 4 to about pH 5, or is at about pH 5.0 ±1.0. In various embodiments, the pH is about 5.0, 5.1, 5.2, 5.3, 5.4, 5.5, 5.6, 5.7, 5.8, 5.9 or 6.0. In various embodiments, the pH is 5.5.

In other embodiments, the compositions contain an isotonicity-adjusting agent to render the solution or suspension isotonic and more compatible for administration. Non-limiting examples of isotonicity agents include NaCl, dextrose, glucose, glycerin, sorbitol, xylitol, and ethanol. In certain embodiments, the isotonicity agent is NaCl. In certain embodiments, NaCl is in a concentration of about 160±20 mM , or about 140 mM±20 mM, or about 120±20 mM , or about 100 mM±20 mM, or about 80 mM±20 mM, or about 60 mM±20 mM.

In yet other embodiments, the compositions comprise a preservative. Preservatives include, but are not limited to, m-cresol and benzyl alcohol. In certain embodiments, the preservative is in a concentration of about 0.4%±0.2%, or about 1%±0.5%, or about 1.5%±0.5%, or about 2.0%±0.5%.

In still other embodiments, the compositions contain an anti-adsorbent (e.g., to mitigate adsorption of a CNP variant to glass or plastic). Anti-adsorbents include without limitation benzyl alcohol, Polysorbate 20, and Polysorbate 80. In certain embodiments, the anti-adsorbent is in a concentration from about 0.001% to about 0.5%, or from about 0.01% to about 0.5%, or from about 0.1% to about 1%, or from about 0.5% to about 1%, or from about 0.5% to about 1.5%, or from about 0.5% to about 2%, or from about 1% to about 2%.

In additional embodiments, the compositions comprise a stabilizer. Non-limiting examples of stabilizers include glycerin, glycerol, thioglycerol, methionine, and ascorbic acid and salts thereof. In some embodiments, when the stabilizer is thioglycerol or ascorbic acid or a salt thereof, the stabilizer is in a concentration from about 0.1% to about 1%. In other embodiments, when the stabilizer is methionine, the stabilizer is in a concentration from about 0.01% to about 0.5%, or from about 0.01% to about 0.2%. In still other embodiments, when the stabilizer is glycerin, the stabilizer is in a concentration from about 5% to about 100% (neat).

In further embodiments, the compositions contain an antioxidant. Exemplary anti-oxidants include without limitation methionine and ascorbic acid. In certain embodiments, the molar ratio of antioxidant to CNP is from about 0.1:1 to about 15:1, or from about 1:1 to about 15:1, or from about 0.5:1 to about 10:1, or from about 1:1 to about 10:1 or from about 3:1 to about 10:1.

Pharmaceutically acceptable salts can be used in the compositions, including without limitation mineral acid salts (e.g., hydrochloride, hydrobromide, phosphate, sulfate), salts of organic acids (e.g., acetate, propionate, malonate, benzoate, mesylate, tosylate), and salts of amines (e.g., isopropylamine, trimethylamine, dicyclohexylamine, diethanolamine). A thorough discussion of pharmaceutically acceptable salts is found in Remington's Pharmaceutical Sciences, $18^{th}$ Edition, Mack Publishing Company, (Easton, Pennsylvania (1990)).

The pharmaceutical compositions can be administered in various forms, such as tablets, capsules, granules, powders, solutions, suspensions, emulsions, ointments, and transdermal patches. The dosage forms of the compositions can be tailored to the desired mode of administration of the compositions. For oral administration, the compositions can take the form of, e.g., a tablet or capsule (including softgel capsule), or can be, e.g., an aqueous or nonaqueous solution, suspension or syrup. Tablets and capsules for oral administration can include one or more commonly used excipients, diluents and carriers, such as mannitol, lactose, glucose, sucrose, starch, corn starch, sodium saccharin, talc, cellulose, magnesium carbonate, and lubricating agents (e.g., magnesium stearate, sodium stearyl fumarate). If desired, flavoring, coloring and/or sweetening agents can be added to the solid and liquid formulations. Other optional ingredients for oral formulations include without limitation preservatives, suspending agents, and thickening agents. Oral formulations can also have an enteric coating to protect the CNP variant from the acidic environment of the stomach. Methods of preparing solid and liquid dosage forms are known, or will be apparent, to those skilled in this art (see, e.g., Remington's Pharmaceutical Sciences, referenced above).

Formulations for parenteral administration can be prepared, e.g., as liquid solutions or suspensions, as solid forms suitable for solubilization or suspension in a liquid medium prior to injection, or as emulsions. For example, sterile injectable solutions and suspensions can be formulated according to techniques known in the art using suitable diluents, carriers, solvents (e.g., buffered aqueous solution, Ringer's solution, isotonic sodium chloride solution), dispersing agents, wetting agents, emulsifying agents, suspending agents, and the like. In addition, sterile fixed oils, fatty esters, polyols and/or other inactive ingredients can be used. As further examples, formulations for parenteral administration include aqueous sterile injectable solutions, which can contain antioxidants, buffers, bacteriostats, and solutes that render the formulation isotonic with the blood of the intended recipient; and aqueous and nonaqueous sterile suspensions, which can contain suspending agents and thickening agents.

Compositions comprising a CNP variant can also be lyophilized formulations. In certain embodiments, the lyophilized formulations comprise a buffer and bulking agent, and optionally an antioxidant. Exemplary buffers include without limitation acetate buffers and citrate buffers. Exemplary bulking agents include without limitation mannitol, sucrose, dexran, lactose, trehalose, and povidone (PVP K24). In certain embodiments, mannitol is in an amount from about 3% to about 10%, or from about 4% to about 8%, or from about 4% to about 6%. In certain embodiments, sucrose is in an amount from about 6% to about 20%, or from about 6% to about 15%, or from about 8% to about 12%. Exemplary anti-oxidants include, but are not limited to, methionine and ascorbic acid.

In various embodiments, the formulation comprises citric acid, sodium citrate, trehalose, mannitol, methionine, polysorbate 80, and optionally sterile water for injection (WFI).

The disclosure also provides kits containing, e.g., bottles, vials, ampoules, tubes, cartridges and/or syringes that comprise a liquid (e.g., sterile injectable) formulation or a solid (e.g., lyophilized) formulation. The kits can also contain pharmaceutically acceptable vehicles or carriers (e.g., solvents, solutions and/or buffers) for reconstituting a solid (e.g., lyophilized) formulation into a solution or suspension for administration (e.g., by injection), including without limitation reconstituting a lyophilized formulation in a syringe for injection or for diluting concentrate to a lower concentration. Furthermore, extemporaneous injection solutions and suspensions can be prepared from, e.g., sterile powder, granules, or tablets comprising a CNP-containing composition. The kits can also include dispensing devices, such as aerosol or injection dispensing devices, pen injectors, autoinjectors, needleless injectors, syringes, and/or needles.

As a non-limiting example, a kit can include syringes having a single chamber or dual chambers. For single-chamber syringes, the single chamber can contain a liquid CNP formulation ready for injection, or a solid (e.g., lyophilized) CNP formulation or a liquid formulation of a CNP variant in a relatively small amount of a suitable solvent system (e.g., glycerin) that can be reconstituted into a solution or suspension for injection. For dual-chamber syringes, one chamber can contain a pharmaceutically acceptable vehicle or carrier (e.g., solvent system, solution or buffer), and the other chamber can contain a solid (e.g., lyophilized) CNP formulation or a liquid formulation of a CNP variant in a relatively small amount of a suitable solvent system (e.g., glycerin) which can be reconstituted into a solution or suspension, using the vehicle or carrier from the first chamber, for injection.

As a further example, a kit can include one or more pen injector or autoinjector devices, and dual-chamber cartridges. One chamber of a cartridge can contain a pharmaceutically acceptable vehicle or carrier (e.g., solvent system, solution or buffer), and the other chamber can contain a solid (e.g., lyophilized) CNP formulation or a liquid formulation of a CNP variant in a relatively small amount of a suitable solvent system (e.g., glycerin) which can be reconstituted into a solution or suspension, using the vehicle or carrier from the first chamber, for injection. A cartridge can comprise an amount of the CNP variant that is sufficient for dosing over a desired time period (e.g., 2 days, 3 days, 1 week, 2 weeks, 3 weeks, 4 weeks, etc.). The pen injector or autoinjector can be adjusted to administer a desired amount of the CNP formulation from a cartridge.

Administration and Dosing

The CNP variants, or pharmaceutical compositions or formulations comprising them, can be administered to subjects in various ways such as, e.g., subcutaneously, intraarticularly, intraperitoneally, intramuscularly, intradermally or orally. In one embodiment, the CNP variant composition is administered once daily, once weekly, once every two weeks, once every three weeks, once every 4 weeks, once every 6 weeks, once every two months, once every three months or once every six months.

The CNP variants or compositions thereof can also be administered by implantation of a depot at the target site of action (e.g., an abnormal or degenerated joint or cartilage area). Alternatively, the CNP variant can be administered sublingually under the tongue (e.g., sublingual tablet) by transdermal delivery (e.g., by means of a patch on the skin) or orally in the form of microspheres, microcapsules, liposomes (uncharged or charged (e.g., cationic)), polymeric microparticles (e.g., polyamides, polylactide, polyglycolide, poly(lactide-glycolide)), microemulsions, and the like.

The CNP variant compositions described herein can be administered to patients in need thereof at therapeutically effective doses to treat, ameliorate or prevent bone-related disorders (e.g., skeletal dysplasias, including achondroplasia). The safety and therapeutic efficacy of the CNP variant can be determined by standard pharmacological procedures in cell cultures or experimental animals, such as, for example, by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Active agents exhibiting a large therapeutic index are normally preferred.

In certain embodiments, the CNP variant compositions described herein are administered at a dose in the range from about 3, 4, 5, 6, 7, 8, 9 or 10 nmol/kg to about 300 nmol/kg, or from about 20 nmol/kg to about 200 nmol/kg. In some embodiments, the CNP compositions are administered at a dose of about 3, 4, 5, 6, 7, 8, 9, 10, 15, 20, 25, 30, 35, 40, 45, 50, 55, 60, 65, 70, 75, 80, 85, 90, 95, 100, 110, 120, 125, 130, 140, 150, 160, 170, 175, 180, 190, 200, 210, 220, 230, 240, 250, 260, 270, 280, 290, 300, 350, 400, 450, 500, 750, 1000, 1250, 1500, 1750 or 2000 nmol/kg or other dose deemed appropriate by the treating physician. In other embodiments, the CNP variant compositions are administered at a dose of about 3, 4, 5, 6, 7, 8, 9, 10, 15, 20, 25, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950 or 1000 pg/kg, or about 0.5, 0.8, 1.0, 1.25, 1.5, 2, 2.5, 3, 3.5, 4, 4.5, 5, 5.5, 6, 6.5, 7, 7.5, 8, 8.5, 9, 9.5 or 10 mg/kg, or other dose deemed appropriate by the treating physician. The doses of CNP or CNP variant described herein can be administered according to the dosing frequency/frequency of administration described herein, including without limitation daily, 2 or 3 times per week, weekly, every 2 weeks, every 3 weeks, monthly, etc. In various embodiments, the CNP or CNP variant is administered daily subcutaneously. In various embodiments, the CNP or CNP variant is administered weekly subcutaneously. In various embodiments, the CNP variant is administered at a dose of 2.5 μg/kg/day to 60 μg/kg/day, 10 μg/kg/day to 45 μg/kg/day, or 15 μg/kg/day to 30 μg/kg/day. In various embodiments, the CNP variant is administered at a dose of 15 μg/kg/day. In various embodiments, the CNP variant is administered at a dose of 30 μg/kg/day.

The frequency of dosing/administration of a CNP variant for a particular subject may vary depending upon various factors, including the disorder being treated and the condition and response of the subject to the therapy. The CNP variant can be administered in a single dose or in multiple doses per dosing. In certain embodiments, the CNP variant composition is administered, in a single dose or in multiple doses, once daily, once weekly, once every two weeks, once every three weeks, once every 4 weeks, once every 6 weeks, once every two months, once every three months or once every six months, or as deemed appropriate by the treating physician. In various embodiments, the CNP variant is administered for 3 month, 6 months, 12 months or more.

In some embodiments, a CNP variant composition is administered so as to allow for periods of growth (e.g., chondrogenesis), followed by a recovery period (e.g., osteogenesis). For example, the CNP composition may be administered subcutaneously or by another mode daily or multiple times per week for a period of time, followed by a period of no treatment, then the cycle is repeated. In some embodiments, the initial period of treatment (e.g., administration of the CNP variant composition daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the CNP variant compositions is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

Biomarkers

For treatment of bone-related disorders, indicators of growth can be measured, such as long bone growth measurements in utero and neonatal and measurements of bone growth biomarkers such as CNP, cGMP, Collagen II, Collagen X, osteocalcin, and Proliferating Cell Nuclear Antigen (PCNA).

One CNP signaling marker is cGMP (guanosine 3',5' cyclic monophosphate). The level of this intracellular signaling molecule increases after CNP binds to and activates its cognate receptor NPR-B. Elevated levels of cGMP can be measured from cell culture extracts (in vitro) after CNP exposure, conditioned media from bone ex-plant studies (ex vivo) after CNP exposure, and in the plasma (in vivo) within minutes of CNP administration subcutaneously, intravenously, or via other routes of administration known in the art.

Cartilage and bone-specific analytes (or cartilage- and bone-associated markers) can also be measured to assess CNP efficacy. For example, fragments of cleaved collagen type II are a cartilage-specific marker for cartilage turnover. Type II collagen is the major organic constituent of cartilage and fragments of type II collagen (cleaved collagen) are released into circulation, and subsequently secreted into the urine, following cartilage turnover. Cartilage turnover precedes new bone formation.

A bone-specific biomarker for bone formation which can be measured is N-terminal propeptides of type I procollagen (PINP). The synthesis of type I collagen is an important step in bone formation, as type I collagen is the major organic component in bone matrix. During collagen synthesis, propeptides are released from the procollagen molecule and can be detected in serum. In addition, fragments of collagen type I can be measured as a marker for bone resorption.

Other potential biomarkers for cartilage and bone formation and growth include aggrecan chondroitin sulfate (cartilage-specific marker for cartilage turnover), propeptides of type II collagen (cartilage-specific marker for cartilage formation), collagen type I C-telopeptide (CTx), alkaline phosphatase (bone-specific) and osteocalcin (bone-specific marker for bone formation). Cartilage- and bone-associated biomarkers can be measured, e.g., in serum from efficacy/pharmacodynamic in vivo studies and from the conditioned media of ex vivo studies, using commercially available kits.

In one embodiment, the level of at least one bone- or cartilage-associated biomarker is assayed or measured in a subject that has been administered a CNP variant or composition described herein in order to monitor the effects of the CNP composition on bone and cartilage formation and growth in vivo. For example, an increase in the level of at least one bone- or cartilage-associated biomarker may indicate that administration of a CNP variant or composition has a positive effect on bone growth and is a useful treatment for skeletal dysplasias and other bone- or cartilage-related diseases or disorders associated with decreased CNP activity. Exemplary bone- or cartilage-associated biomarkers include, but are not limited to, CNP (e.g., endogenous levels of CNP), cGMP, propeptides of collagen type II and fragments thereof, collagen type II and fragments thereof, collagen type I C-telopeptide (CTx), osteocalcin, proliferating cell nuclear antigen (PCNA), propeptides of type I procollagen (PINP) and fragments thereof, collagen type I and fragments thereof, collagen X, aggrecan chondroitin sulfate, and alkaline phosphatase.

In various embodiments, biomarkers are measured by obtaining a biological sample from a subject who will be administered, is being administered or has been administered a CNP variant. Biomarkers can be measured using techniques known in the art, including, but not limited to, Western Blot, enzyme linked immunosorbant assay (ELISA), and enzymatic activity assay. The biological sample can be blood, serum, urine, or other biological fluids.

Additional aspects and details of the disclosure will be apparent from the following examples, which are intended to be illustrative rather than limiting.

EXAMPLES

Example 1: Synthesis of CNP Variants

CNP variant peptides were synthesized on solid-phase using a resin that would leave a C-terminal COOH on a Symphony/Prelude (Protein Technologies Inc., USA), Voyager (CEM GmbH, Germany), or Syroll (MultiSyntech, Germany) synthesizer.

All Fmoc-amino acids were purchased from Biosolve (Netherlands) or Bachem GmbH (Germany) with side-chain functional groups protected with N-t-Boc (KW), O-t-Bu (DESTY), N-Trt (HNQ), S-Trt (C), or N-Pbf (R) groups. A 5-fold excess of HBTU/HOBt/amino acid/DIPEA (1:1:1:2) in NMP with a 20 minute activation time using double couplings was employed for every amino acid coupling step.

Acetylation (Ac) of the peptide was performed by reacting the resin with NMP/$Ac_2O$/DIEA (10:1:0.1, v/v/v) for 30 min at room temperature.

For conjugation of a moiety, the protective amino group on lysine was cleaved to create a reactive group. Standard Fmoc synthesis was used to react 2× Fmoc-amino PEG(2) followed by glutamic acid, followed by C18-diacid.

The completed peptide was cleaved from the resin by reaction with a TFA (40 mL/mmol resin) for 2 hours at room temperature. Crude peptide was filtered, precipitated with ice-cold $Et_2O$ followed by lyophilization and ultimately purification by preparative reverse phase-high-performance liquid chromatography (RP-HPLC). Final products and purity were confirmed by mass spectrometry.

CNP variants were generated based on the sequence of Pro-Gly CNP-37 (PGQEHPNARKYKGANKKGLSKGCFGLKLDRIGSMSGLGC(SEQ ID NO: 1)), optionally having changes in different amino acid residues, and/or acetylation at the N-terminus, and/or other modifications, and include (amino acid changes underlined):

CNP-8:
(SEQ ID NO: 8)
Ac-PGQEHPQARRYRGAQRRGLSRGCFGLKLDRIGSMSGLGC-OH,

CNP-5:
(SEQ ID NO: 9)
Ac-PGQEHPNARKYKGANKKGLSKGCFGLKLDRIGSMSGLGC-NH2,

CNP-6:
(SEQ ID NO: 10)
Ac-PGQEHPNARRYRGANRRGLSRGCFGLKLDRIGSMSGLGC-OH,

CNP-7:
(SEQ ID NO: 11)
Ac-PGQEHPNARRYRGANRRGLSRGCFGLKLDRIGSMSGLGC-NH2,

CNP-9:
(SEQ ID NO: 12)
Ac-PGQEHPQARRYRGAQRRGLSRGCFGLKLDRIGSMSGLGC-NH2, (SEQ ID NO: 8)
Ac-PGQEHPQARRYRGAQRRGLSRGCFGLK(AEEA-AEEA-γGlu-C18DA)LDRIGSMSGLGC-OH,
and (SEQ ID NO: 7)
PGQEHPQARKYKGAQKKGLSKGCFGLKLDRIGSMSGLGC-OH.

Fully reduced peptides were dissolved in 0.1 M Tris-buffer (pH 8.0) with or without guanidine HCl, containing 1 mM cysteine (SS-form) and 8 mM cysteine (SH-form) in a final concentration of 0.1 mg/mL and stirred at room temperature. Disuflide formation was monitored by HPLC-analysis until no further peak changes were observed. Mixtures were loaded on preparative RP-HPLC for purification.

Example 2: Characterization of Synthesized CNP Variants

CNP variants synthesized as in Example 1 were analyzed by mass spectrometry and UV spectroscopy to determine purity and stability after 10 days.

Stability was measured using RP-HPLC analysis of purity over time T0 to T10. Briefly, the CNP variants were diluted 1:5 in buffer: 5 mM citrate, 6% sucrose, 1.5% mannitol, 0.7 mg/ml methionine and 0.005% tween80, pH 5.6 An injection volume of 10 μL was injected onto a Phenomenex Aeris XB-C18 RP column (2 μm, 100A, 2.1×250 mm; p/n 00G-4505-AN) HPLC conditions were: Mobile Phase A: $H_2O$/0.05% TFA, pH 3 w/$NH_4OH$ (~3 mM final), Mobile Phase B: 70% $CH_3CN$ in $H_2O$/0.05% TFA, pH 3 w/$NH_4OH$ (~3 mM final) and a flow rate of 0.25 mL/min. Measurement was carried out with a column temperature of 55° C. and UV: 214 nm (bw 4 nm); ref 360 nm (bw 20 nm), UV: 280 nm (bw 4 nm); ref 360 nm (bw 20 nm). CNP variants were held 10 days in PBS, pH 7.4, at 37° C. and stability measurements obtained. Results of stability measurements are shown in Table 1 below as % variant detected at T0 (0 days) or T10 (10 days).

TABLE 1

| Peptide | T0, % | T10, % | EC50, T0, nm |
|---|---|---|---|
| Pro-Gly CNP37 | 76.7 | 39.5 | 1.7 |
| CNP-5 | 83 | 47 | 3 |
| CNP-6 | 90 | 58 | 0.4 |
| CNP-7 | 77 | 53 | 2.1 |
| CNP-8 | 91 | 88 | 0.2 |
| CNP-9 | 92 | 77 | 0.9 |

CNP variants were tested for activity by a cGMP stimulation assay using a CatchPoint Cyclic-GMP Fluorescent Assay Bulk kit (Molecular Devices, R8075). Briefly, NIH3T3 cells (ATCC, CRL-1658) and HEK293 cells were seeded at 60,000 cells/well in a 96-well plate (96-well black imaging plates, Grenier, #655090). Culture media was as follows: NIH3T3 culture media: DMEM high glucose, pyruvate (Thermo, 11995-073)+10% FBS+1× Pen Strep (abbrev P/S, Thermo, cat# 15140122). NIH3T3 was the control system for the cGMP assay HEK293 culture media: EMEM+10% FBS+1×P/S+1×GMAX. Serum free NIH3T3 media: DMEM+1×P/S for treatment of cells with IBMX (CAS 28822-58-4); Serum free NIH3T3 media with BSA: DMEM+1×P/S+0.5 mg/mL BSA (Thermo, A9418-100G) for treatment of cells with CNP.

Cells were incubated for 24 hours at 37° C., 5% $CO_2$. For cells to be treated with CNP variants, plates were pre-treated with IBMX (Enzo life sciences, 89161-340, 1 g) 15 minutes prior to use. IBMX is a potent, non-specific inhibitor of phosphodiesterases. An 800 mM stock solution of IBMX is diluted in IBMX dilution media (serum-free media (DMEM+1× PBS mixed 1:1 with 1× PBS) to a 0.75 mM working stock.

CNP variants were prepared as follows: Dilute 10 mg/ml CNP solution 1:1000 in CNP dilution media (DMEM+1× P/S+0.5 mg/mL BSA). This solution is further diluted to obtain a CNP starting solution plated at 100 nM CNP/well. This 100 nM CNP solution is further serially diluted 1:5 for six dilutions to obtain a lower end concentration of 0.0064 nM CNP /well. This provides a 7-point dose curve for analysis.

For cell treatment, cells were removed from the incubator, growth media was removed from cells and cells treated with IBMX. 80 μL 0.75 mM IBMX was added to each well and cells returned to 37° C. incubator for 15 minutes. After 15 minutes CNP (40 μL/well) was added to each test well and cells returned to 37° C. incubator for 15 minutes. The plate was mixed by gentle tapping. The plate was imaged on a Solentim cell metric to visualize cells and determine if there is any cell lifting and then placed back into 37° C. incubator.

The reaction was stopped and cells lysed by adding 40 μL lysis buffer (from cGMP kit). Plate was placed on a shaker for 5 minutes to complete lysis. The cell lysate was used in the cGMP assay.

The cGMP assay was carried out using a cGMP calibrator, rabbit anti-cGMP antibody and HRP-cGMP prepared as according to manufacturer's protocol. 40 μL of calibrator was added to wells of an anti-cGMP antibody coated plate, and 40 μL of lysate to be analyzed added to the appropriate wells. 40 μL of reconstituted rabbit anti-cGMP antibody was added to all wells and plates placed on shaker five minutes for mixing. 40 μL of reconstituted HRP-cGMP was added to each well and incubated for 2 hours at room temperature. Plates were manually aspirated and washed 4× with 300 μL wash buffer. 100 μL of stoplight red substrate was added to each well, the plate covered and left at room temperature for at least 10 mins, protected from light. The plate was read for fluorescence intensity on a Spectramax M, or similar instrument, at excitation 530 nm and emission at 590 nm.

Table 1 shows that the CNP variants stimulate cGMP production, suggesting that the stable variants described herein are useful as therapeutics to treat bone-related disorders.

Example 2A: Stability of CNP Variants or Conjugates in Plasma

Stability of different CNP variants or CNP conjugates were tested for stability in human plasma over a 24 hour period. Briefly, a C18 fatty acid was fused to gamma glutamic acid using 2 OEG spacers (see e.g., Lau et al., J. Med. Chem 58:7370-7380, 2015). For the chromatography, Waters UPLC H-Class connected with BEH C18 1.7 um, 2.1×150 mm; Mobile Phase A: 1% DMSO 0.1% Formic Acid in Water; Mobile Phase B: 1% DMSO 0.1% Formic Acid in CAN. Mass Spectrometry was carried out using an AB Sciex QTRAP.

each CNP variant was prepared at 200 nM in Human Plasma Li Heparin and samples Incubated at 37° C. 5% $CO_2$. The reaction was quenched at 0, 1, 2, 4, 8, 24 hours with 0.5M Sodium Citrate pH 4. Plasma proteins were precipitated with 0.2% Formic Acid in MeOH and samples prepared using WCX 96-well uElution plate and analyzed by LC-MS/MS 6500.

Variants CNP-R refers to CNP37 variants in which the K residues not in the ring portion are changed to R residues, and CNP Q/R refers to CNP37 variants in which N residues are changed to Q and K residues not in the ring portion are changed to R.

Figure 2B:
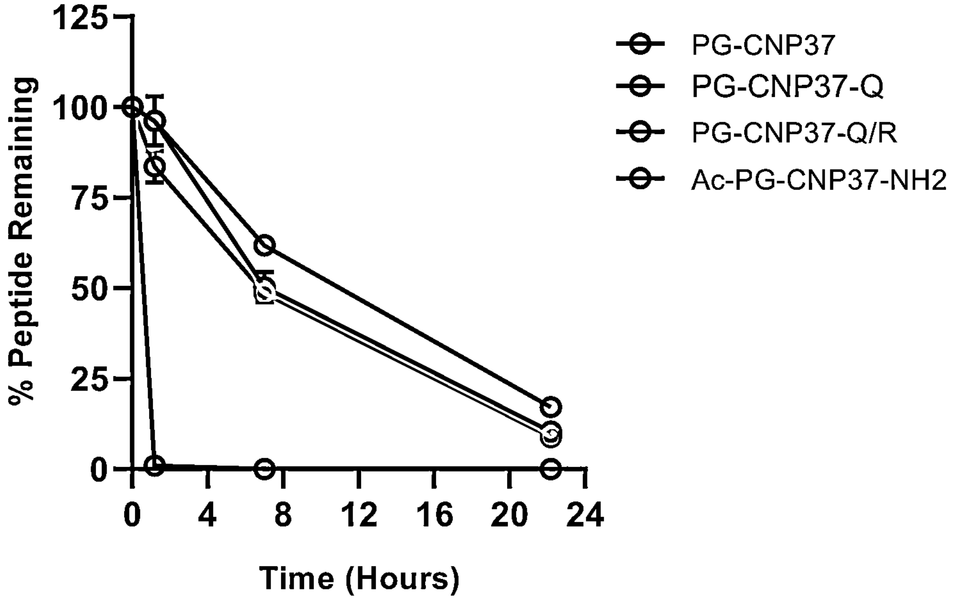

FIG. 1 illustrates CNP conjugates having different linker structures. FIG. 2 shows that lipidated conjugate has improved stability in plasma compared to PEGylated or non-conjugated peptides in plasma.

Figure 3:
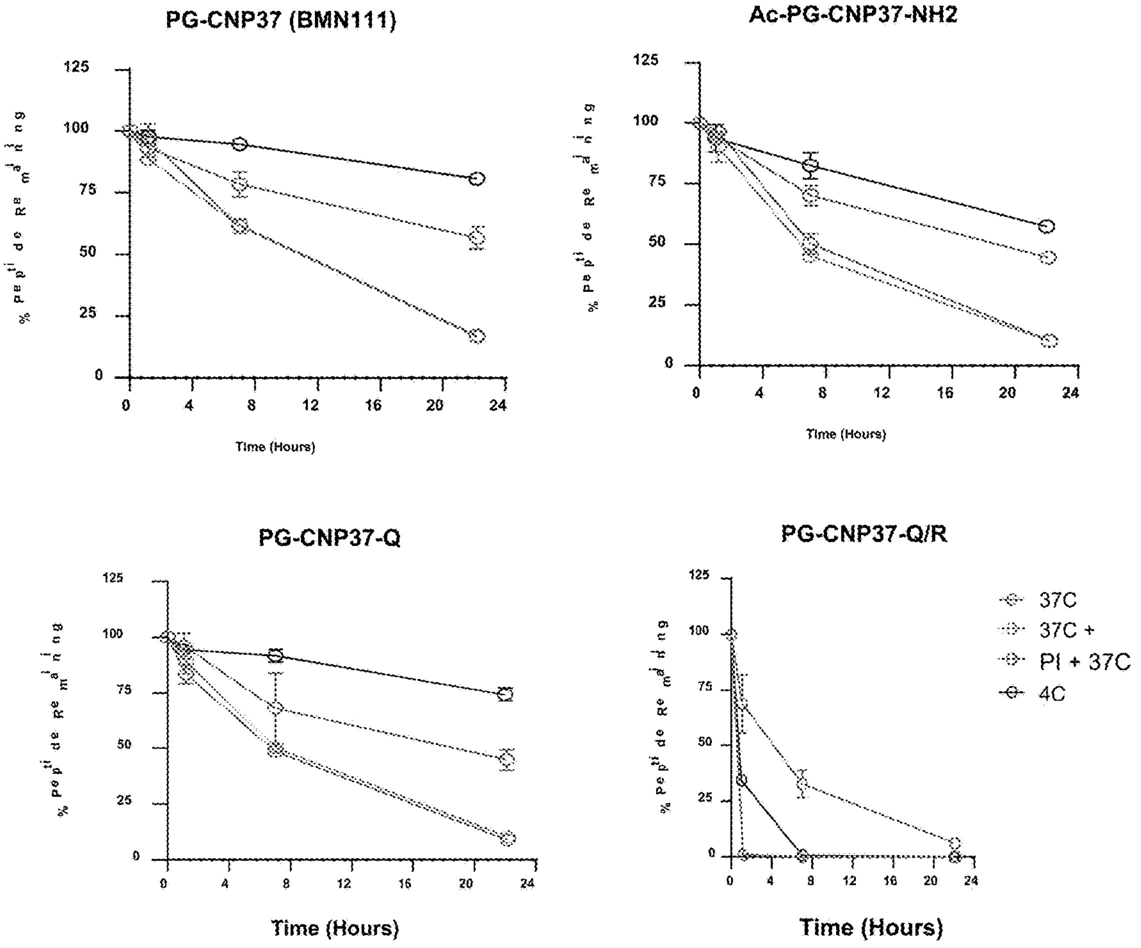
FIG. 3 shows the stability of CNP variants under different culture conditions.

Stability of different conjugates was also analyzed at varying conditions. Briefly, the same protocol as above was used at 37° C. (control), 37° C.+0.5M NaCl, 37° C.+protease inhibitors or 4° C. FIG. 3 shows that PG-CNP37 and variants are prone to proteolysis in human plasma and PG-CNP37 shows greater stability compared to other variants.

Example 3: Heterozygous NPR2 Mutations Are Responsive to CNP Treatment

To determine the effects of CNP on subjects with short stature resulting from NPR2 mutations, cellular models of NPR2 mutations were developed. Exemplary NPR2 mutations analyzed are set out in FIG. 6. Rat chondrosarcoma (RCS) cells having either a knockout of, or heterozygous loss of function mutations in, the NPR2 gene were made by RNP transfection into RCS cells using 125 ng NPR2 variants or wild-type NPR2 plasmid DNA transfected into RCS or HEK293 cells. Single cell clones were seeded and genotyped by Sanger sequencing. Cell models are able to reproduce published cGMP phenotypes of the different mutations.

Figure 4:
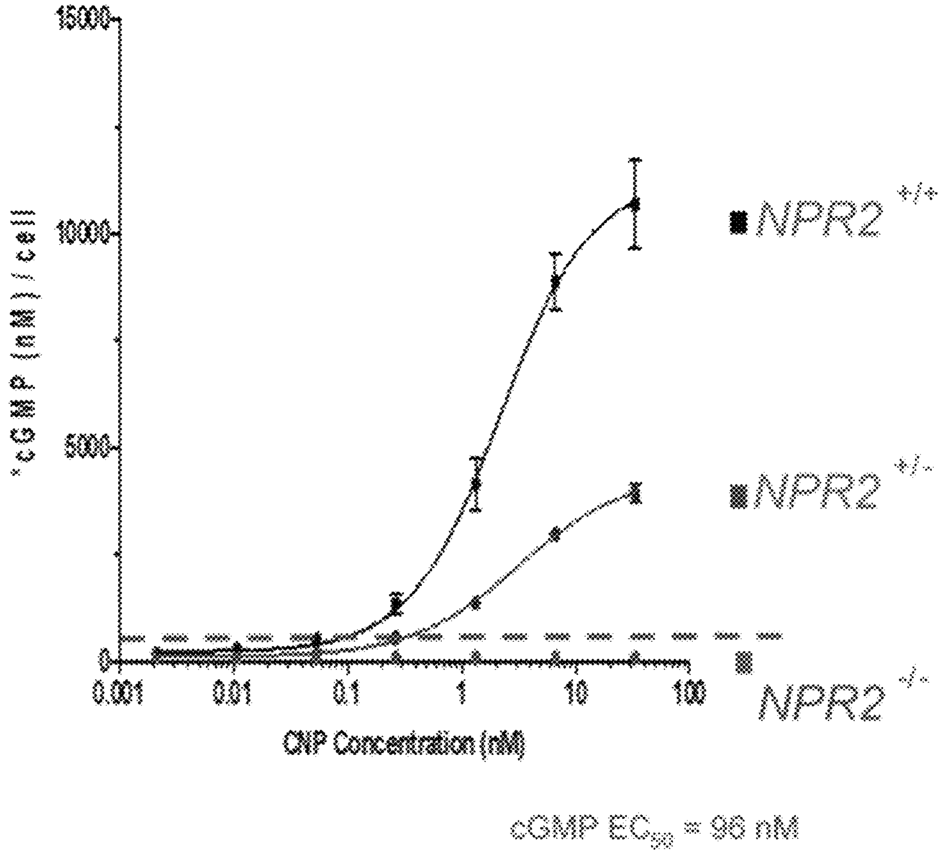
FIG. 4 shows the effects of a CNP variant (Pro-Gly-CNP) on cells carrying either NPR2 homozygous or heterozygous mutations, as measured by cGMP stimulation.

The NPR2 clones were created by creating insertions and deletions in the first exon of NPR2 in RCS cells. The sequence of the first exon in NPR2 was confirmed by next-generation sequencing and is set out in FIG. 5. NPR2 mutant cells were tested for activity in response to CNP administration by a cGMP stimulation assay using a Catch Point Cyclic-GMP Fluorescent Assay after treatment with 6 nM of Pro-Gly CNP37. RCS (rat chondrosarcoma) cells were seeded at 40,000 cells/well in RCS culture media: DMEM+10% FBS+1× Pen Strep. FIG. 4 shows that adding exogenous Pro-Gly-CNP37 variant rescues cGMP readout in a NPR2+/−rat chondrosarcoma cell model.

Previous activation data reports cGMP EC50 in the range of 40 to 360 nM for activation of PRKG2 (Campbell et al., ACS Chem Biol 12, 2388-2398, 2017); Vaandrager et al., J Biol Chem 272, 11816-23, 1997); Pohler et al., FEBS Lett 374, 419-25, 1995). In the heterozygous NPR2 knockout cells, a CNP dose >0.163 nM is able to achieve an intracellular concentration exceeding the EC50 range for PRKG2 activation cGMP (FIG. 4). Whereas, in wild-type cells a CNP dose of 0.040 nM is able to achieve the same cGMP concentration. These results demonstrate that CNP supplementation can achieve the cGMP levels necessary for PRKG2 activation and growth in cells with loss-of-function mutations of NPR2.

These results also suggest that administration of CNP variants is useful to restore bone growth in subjects with short stature that have reduced activity of NPR2. It is further contemplated that treatment with CNP variants will be beneficial in subjects having mutations in other growth plate genes in which cGMP signaling may be impaired.

Example 4: Identification of Mutations Associated With Short Stature

It is hypothesized that genes showing clear evidence of genetically-driven bi-directional effects are more likely to represent therapeutic targets that can be effectively modulated in a broad patient population. To identify genes that are core regulators of growth, the intersections of five gene lists were analyzed including, the list of genes from genome-wide association study (GWAS). Core growth regulators would be the most likely to contain rare coding mutations with bidirectional effects (i.e. short stature or skeletal dysplasia AND tall stature or overgrowth).

Databases queried include: GWAS 2,067 non-repeating closest genes for each of the 3,290 independent genetic variants reported by a large GWAS meta-analysis of height using ~700,000 individuals were extracted; HGMD The "allmut" table from HGMD version v2019_2 was queried looking for all pathogenic variants labelled as "DM" having either "short stature" and "tall stature or overgrowth" in the same genes; OMIM The list of OMIM genes related to growth disorders was previously described and was created using the keywords: short stature, overgrowth, skeletal dysplasia, brachydactyly.

First, the Human Gene Mutation Database (HGMD version v2019_2) was queried for genes associated with short or tall stature (Stenson et al., Hum Genet 136:665-677, 2017). There were 47 genes annotated with at least one pathogenic variant reported in the literature to cause "short stature". Only 20 genes were annotated as tall stature or overgrowth genes. Secondly, a manually curated list of 258 OMIM genes was used (248 short, 20 tall) which was created using the keywords: short stature, overgrowth, skeletal dysplasia, brachydactyly (Wood et al., Nat Genet 46:1173-86, 2014). Third, the intersection of these lists was compared with the list of genes from GWAS. At the intersection of these list there were three genes known to be associated with height (IGF1R, NPPC, NPR2) and two additional genes were identified (FGFR3, SHOX).

Additional analysis led to generation of a new group of five Core genes that showed significantly decreased height (β=−0.20, 95% Cl [−0.26 to −0.14], p=4.04×10−11) and significantly increased risk for Idiopathic Short Stature (ISS) (OR=2.75, 95% Cl [1.92-3.96]. Each of the core five genes (FGFR3, IGF1R, NPPC, NPR2 and SHOX) were associated with height when considered individually, and also were associated with short stature when taken in combination with other mutations. Exemplary mutations in FGFR3, IGF1R, NPPC, NPR2 and SHOX are set out in FIG. 7.

Combined LoF (loss of function) and Missense variants in NPR2 and IGF1R were also associated with increased risk for ISS (OR=3.31, P=0.001, OR=2.85, P=0.002, respectively). Entire gene deletions and/or mutations causing loss of protein function in SHOX, IGF1R, NPPC, NPR2 have been reported in familial short stature with various degrees of severity.

Analysis shows that carriers of variants in any of the five core genes are at approximately a 3-fold increased risk for ISS and account for 6.7% of the total ISS population. Furthermore, a dose-dependent rescue of NPR2 signaling in a cell model of NPR2 haploinsufficiency after adding exogenous CNP was demonstrated.

Figures 8A, 8B, 8C, 8D, 8E, 8F:
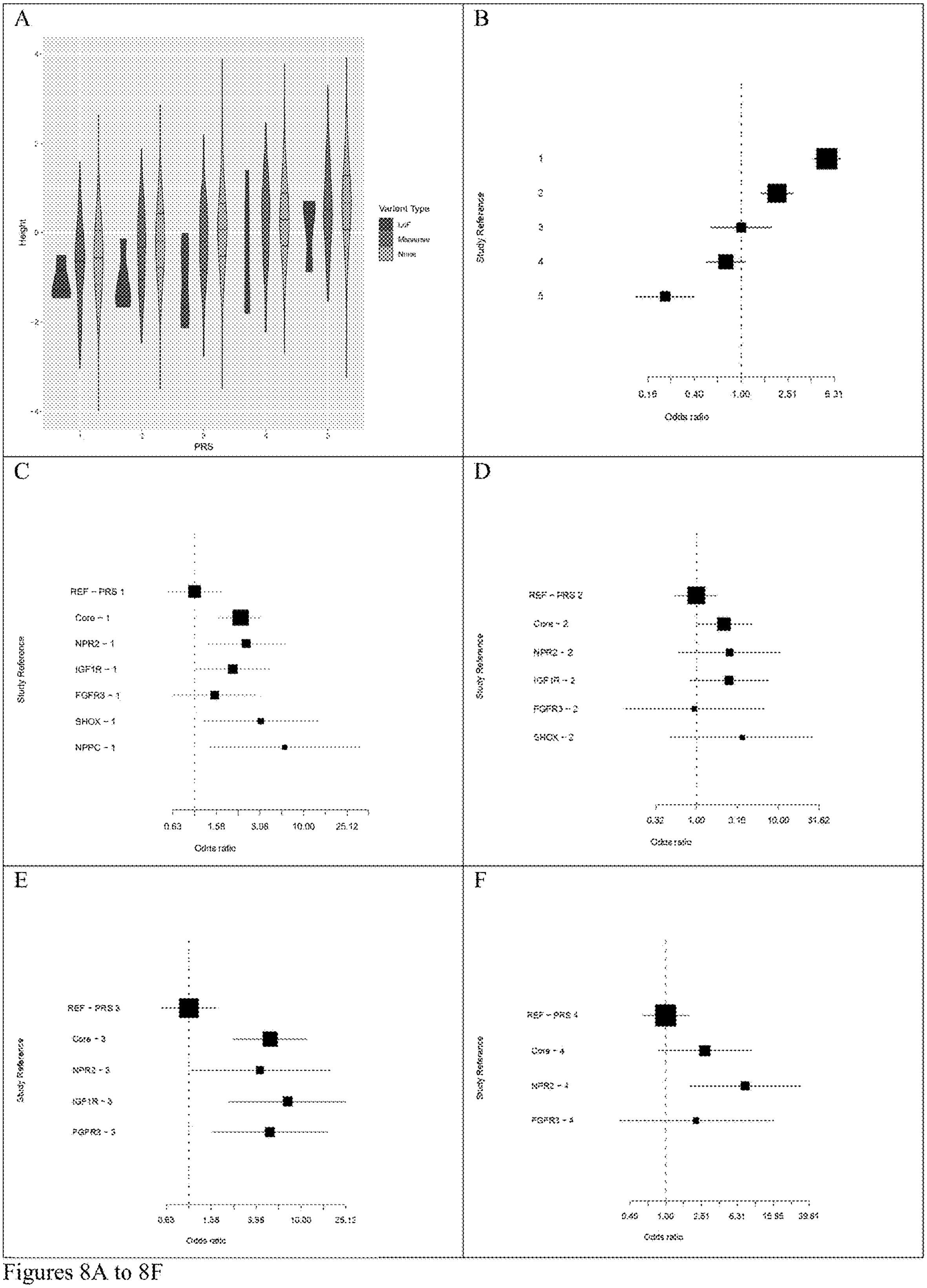
FIG. 8A. Effects on height as a quantitative trait, samples were divided in five groups based on their PRS, violin-plots with horizontal lines representing the 25%, 50% and 75% percentile of height. Samples were grouped by carrying status of missense, loss of function or None in any of the five core genes.
FIG. 8B. Effect reflected on Odds ratios for "Idiopathic Short Stature" or ISS. Odds for ISS using PRS=3 as reference vs the other PRS groups.
FIG. 8C. Odds for ISS using PRS=1 as reference vs having missense and/or loss of function variants in core genes.
FIG. 8D. Odds for ISS using PRS=1 non-carriers as reference vs having missense and/or loss of function variants in core genes.
FIG. 8E. Odds for ISS using PRS=2 non-carriers as reference vs having missense and/or loss of function variants in core genes.
FIG. 8F. Odds for ISS using PRS=3 non-carriers as reference vs having missense and/or loss of function variants in core genes. G. Odds for ISS using PRS=4 non-carriers as reference vs having missense and/or loss of function variants in core genes.

According to the omnigenic model (Liu, et al., Cell 177:1022-1034 e6 (2019); Boyle et al., Cell 169:1177-1186 (2017)) if these genes are core human growth genes, then their effects should be modulated by multiple weaker common genetic variants driving regulatory networks. To indirectly test this hypothesis, polygenic risk scores (PRS) were calculated for height using the largest published GWAS meta-analysis for height that did not include any samples from the UK Biobank project. The cohort was divided into five equally-sized (n=6,824) PRS quintiles (PRS 1 being the lowest height, PRS 5 the tallest height). There was a dose-dependent relationship between increasing PRS score and mean height (β=0.30 per each PRS quintile increase) (FIG. 8A). Carriers of LoF variants in the five core genes were consistently shorter than non-carriers across the five different PRS backgrounds. See FIG. 8. The data suggest that the combined effect of PRS and rare protein variants is consistent with an additive model: polygenic effects modulated height in both carriers and non-carriers.

The risk for ISS across PRS groups was calculated using PRS=3 as a reference. The lowest PRS group was associated with increased risk for ISS and the highest PRS group with a decreased risk (OR=5.43, P=8.58×10−34; OR=0.22, P=4.49×10−7 for PRS 1 and PRS 5 respectively). The effect of rare coding variants of the five core genes was evaluated for ISS stratified by PRS group. Carriers of any of the five core genes were at increased risk for ISS in the first three quintiles (OR=2.64, P=3.09×10−5; OR=2.17, P=0.04; OR=5.29, P=1.58×10−5; OR=2.72, P=0.09 FIGS. 8C-F). Consistent directions of effect were observed for carriers of each individual core gene on ISS risk stratified by PRS (FIGS. 8C-F).

Further, additive effects of PRS, mostly coming from multiple common genetic variation with individual small effects, predicted 20.1% of the variance in height in the dataset. These additive effects of PRS appeared to have similar magnitude on carriers of rare coding variation of core genes as well as in non-carriers. This observation indicates that PRS may be a strong contributor in the differences in penetrance of rare pathogenic variants (especially in models of haploinsufficiency such as the ones described here). Supporting this idea, it was observed that two of eight NPR2 variant carriers with low NPR2 activity had a low-normal height. This data suggests that most ISS individuals possessing mutations in NPR2 may also have a polygenic background that made them more susceptible to the pathogenic effect of losing NPR2 activity.

These results support the idea that CNP-based treatments could be effective in NPR2 haploinsufficient patient populations. Further, results showing a significant bi-directional (LoF and GoF) correlation of cGMP levels and height in NPR2 carriers of the general population suggest that targeting this receptor with CNP analogs could be an effective therapy for all ISS individuals.

It is understood that every embodiment of the disclosure described herein may optionally be combined with any one or more of the other embodiments described herein. Every patent literature and every non-patent literature cited herein are incorporated herein by reference in their entirety.

It is understood, therefore, that this invention is not limited to the particular embodiments disclosed, but is intended to cover all modifications which are within the spirit and scope of the invention as defined by the appended claims; the above description, and/or shown in the attached drawings. Consequently only such limitations as appear in the appended claims should be placed on the disclosure.

What is claimed:

1. A peptide consisting of the amino acid sequence PGQEHPNARKYKGANKKGLSKGCFGLKLDRI-GSMSGLGC (SEQ ID NO: 1); and an AEEA-AEEA-γGlu-C18DA structure complexed via a linker to the lysine residue (K) at position 27, wherein the AEEA-AEEA-γGlu-C18DA structure and linker together has the structure:

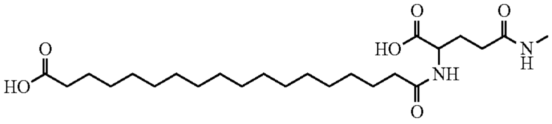

-continued

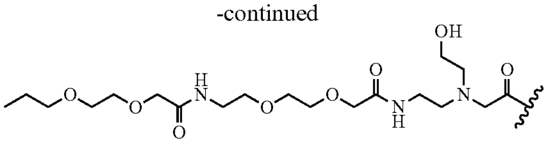, and “” represents a point of attachment to the lysine residue.

2. A pharmaceutical composition comprising a peptide according to claim 1, and a pharmaceutically acceptable excipient, carrier or diluent.

* * * * *